US010888599B2

(12) United States Patent
Alamdari et al.

(10) Patent No.: US 10,888,599 B2
(45) Date of Patent: Jan. 12, 2021

(54) COMPOSITIONS AND METHODS TO IMPROVE EXERCISE PERFORMANCE AND RECOVERY

(71) Applicant: Beachbody, LLC, El Segundo, CA (US)

(72) Inventors: Nima Alamdari, Los Angeles, CA (US); Michael Wilson, Rossmoor, CA (US); May Lam, Torrance, CA (US)

(73) Assignee: Beachbody, LLC, Santa Monica, CA (US)

( * ) Notice: Subject to any disclaimer, the term of this patent is extended or adjusted under 35 U.S.C. 154(b) by 336 days.

(21) Appl. No.: 15/735,090

(22) PCT Filed: Jun. 13, 2016

(86) PCT No.: PCT/US2016/037280
§ 371 (c)(1),
(2) Date: Dec. 8, 2017

(87) PCT Pub. No.: WO2016/201449
PCT Pub. Date: Dec. 15, 2016

(65) Prior Publication Data
US 2018/0185432 A1 Jul. 5, 2018

Related U.S. Application Data

(60) Provisional application No. 62/174,407, filed on Jun. 11, 2015, provisional application No. 62/174,419, filed on Jun. 11, 2015, provisional application No. 62/174,421, filed on Jun. 11, 2015, provisional application No. 62/174,405, filed on Jun. 11, 2015.

(51) Int. Cl.
| | | |
|---|---|---|
| *A61K 36/82* | (2006.01) |
| *A61K 36/28* | (2006.01) |
| *C07C 59/265* | (2006.01) |
| *A23L 33/105* | (2016.01) |
| *A23L 33/175* | (2016.01) |
| *A23L 33/16* | (2016.01) |
| *A23L 2/52* | (2006.01) |
| *A23L 33/125* | (2016.01) |
| *A61P 3/02* | (2006.01) |
| *A61P 21/00* | (2006.01) |
| *A61P 29/00* | (2006.01) |
| *A61P 3/12* | (2006.01) |
| *A61K 31/194* | (2006.01) |
| *A61K 31/197* | (2006.01) |
| *A61K 31/352* | (2006.01) |
| *A61K 31/522* | (2006.01) |
| *A61K 36/185* | (2006.01) |
| *A61K 36/736* | (2006.01) |
| *A61K 38/16* | (2006.01) |
| *A61K 38/17* | (2006.01) |

(52) U.S. Cl.
CPC .............. *A61K 36/82* (2013.01); *A23L 2/52* (2013.01); *A23L 33/105* (2016.08); *A23L 33/125* (2016.08); *A23L 33/16* (2016.08); *A23L 33/175* (2016.08); *A61K 31/194* (2013.01); *A61K 31/197* (2013.01); *A61K 31/352* (2013.01); *A61K 31/522* (2013.01); *A61K 36/185* (2013.01); *A61K 36/28* (2013.01); *A61K 36/736* (2013.01); *A61K 38/168* (2013.01); *A61K 38/1709* (2013.01); *A61P 3/02* (2018.01); *A61P 3/12* (2018.01); *A61P 21/00* (2018.01); *A61P 29/00* (2018.01); *C07C 59/265* (2013.01); *A23V 2002/00* (2013.01)

(58) Field of Classification Search
CPC .... A61K 2300/00; A61K 36/28; A61K 36/82; A61K 31/194; A61K 31/197; A61K 31/352; A61K 31/522; A61K 36/185; A61K 36/736; A61K 38/168; A61K 38/1709; A23V 2002/00; A23V 2200/33; A23V 2200/332; A23L 2/52; A23L 33/105; A23L 33/125; A23L 33/16; A23L 33/175; A61P 21/00; A61P 29/00; A61P 3/02; A61P 3/12; C07C 59/265
See application file for complete search history.

(56) References Cited

U.S. PATENT DOCUMENTS

| | | | |
|---|---|---|---|
| 5,480,657 A | 1/1996 | Allen | |
| 5,626,849 A | 5/1997 | Hastings et al. | |
| 6,039,989 A | 3/2000 | Bangs et al. | |
| 6,413,545 B1 | 7/2002 | Alviar et al. | |
| 6,706,697 B1 | 3/2004 | MacDonald | |
| 7,001,618 B1 | 2/2006 | Sunvold et al. | |
| 7,538,262 B2 * | 5/2009 | Hammer ................. | C12N 9/88 435/252.3 |
| 8,257,694 B2 | 9/2012 | Daikeler et al. | |
| 2005/0106218 A1 | 5/2005 | Ward et al. | |
| 2006/0159724 A1 | 7/2006 | Bell | |

(Continued)

FOREIGN PATENT DOCUMENTS

| | | |
|---|---|---|
| CA | 2989153 A1 | 12/2016 |
| CN | 102405969 A * | 4/2012 |

(Continued)

OTHER PUBLICATIONS

EP 16808534.8 Partial Search Report dated Jan. 3, 2019.
(Continued)

*Primary Examiner* — Aaron J Kosar
(74) *Attorney, Agent, or Firm* — Nixon Peabody LLP

(57) ABSTRACT

The invention relates to various compositions for improving exercise performance and/or recovery. The invention also relates to methods of using these compositions and kits including these compositions to improve exercise performance and/or recovery.

26 Claims, 14 Drawing Sheets

(56) References Cited

U.S. PATENT DOCUMENTS

| | | | |
|---|---|---|---|
| 2007/0292542 A1 | 12/2007 | Astrup et al. | |
| 2009/0018072 A1 | 1/2009 | Scheele | |
| 2009/0061016 A1 | 3/2009 | Selzer et al. | |
| 2009/0123380 A1 | 5/2009 | Hirsch | |
| 2009/0241219 A1* | 9/2009 | Hammer | C12N 9/88 |
| | | | 800/278 |
| 2010/0074969 A1 | 3/2010 | Hughes et al. | |
| 2010/0119498 A1 | 5/2010 | Hastings | |
| 2010/0316753 A1 | 12/2010 | Amagase | |
| 2012/0052151 A1 | 3/2012 | Sannino | |
| 2013/0053307 A1 | 2/2013 | Emma | |
| 2013/0261183 A1 | 10/2013 | Bhagat | |
| 2013/0344177 A1 | 12/2013 | Young et al. | |
| 2015/0342237 A1 | 12/2015 | Daikeler et al. | |
| 2018/0338518 A1 | 11/2018 | Daikeler et al. | |

FOREIGN PATENT DOCUMENTS

| | | | |
|---|---|---|---|
| DE | 202013005568 U1 | 5/2014 | |
| EP | 3307083 A1 | 4/2018 | |
| WO | 2001/05356 A2 | 1/2001 | |
| WO | WO-2009085928 A2 * | 7/2009 | A23L 2/52 |
| WO | 2014/028122 A1 | 2/2014 | |
| WO | 2015/184401 A1 | 12/2015 | |
| WO | 2016/201449 A1 | 12/2016 | |

OTHER PUBLICATIONS

Baur, J., The Truth About Sugar for Athletes retrieved from: https://www.stack.co m/a/the-truth-about-suga r-for-athletes on Nov. 8, 2018, 2011, 16 pages.

Anonymous, Sudzucker Feinzucker RF, 10er Pack (10x 1kg) retrieved from:https://www.amazon.de/Sudzucker-Feinzu cker-10er-Pack-10x/dp/B00XJMH4UK/ref=sr 1 5?s=grocery&ie=UTF8&qid=I541688972&sr=1-5&keywords=zucker on Nov. 8, 2018, 2014, 6 pages.

Hitti, M., Dextrose May Boost Sports Performance retrieved from: https://www.webmd.com/fitness-exercise /news/20060113/dextrose-may-boost-sports-performance on Nov. 8, 2018, 2006, 5 pages.

Anonymous, Wai ki ki Bai Bubbles Coconut retrieved from: http://web.archive.org/web/20150426100 650/http://www.drinkbai.com:80/bubbles/wai kiki-coconut on Nov. 12, 2018, 2015, 6 pages.

16808534.8 Extended Search Report dated Apr. 23, 2019, 32 pages.

Campbell et al., International Society of Sports Nutrition Position Stand: Energy Drinks, Journal of Internation Society of Sports Nutrition, 2013, vol. 10(1), pp. 1-16.

Lewis, A., StrongGirl Pre Workout Review: Pretty Face, Crappy Performance, 2015, retrieved from https://bestpreworkoutforwomen.com/StrongGirl-Pre-Workout-Review.html on Apr. 9, 2019, 7 pages.

Mintel, Tropical Punch Premium Energy Shot, 2013, retrieved from www.gnpd.com, 3 pages.

Mintel, Strawberry Mojito Flavored Beverage, 2015, retrieved from www.gnpd.com, 4 pages.

Oat Grass, http://web.archive.org/web/20131110232349/https://jonbarron.org/herbal-library/nutraceuticals/oat-grass Sep. 16, 2013, 2013, pp. 1-2.

Sharafi et al., Effect of High-Protein, High-Fiber Beverage Preload on Subjective Appetite Ratings and Subsequent Ad Libitum Energy Intake in Overweight Men and Women: A Randomized Double-Blind Placebo-Controlled, Crossover Study, Current Developments in Nutrition, 2018, vol. 2, pp. 1-8.

What's in Shakeology and How it Works, http://web.archive.org/web/20121224004028/http://images.beachbody.com/shakeology/science/SHK_Chart.pdf Dec. 24, 2012, 2012, pp. 1.

International Search Report and Written Opinion for PCT/US2015/33398 dated Aug. 19, 2015, 8 pages.

International Preliminary Report on Patentability for PCT/US2015/33398 dated Dec. 6, 2016, 6 pages.

International Search Report and Written Opinion for PCT/US2016/37280 dated Sep. 2, 2016, 9 pages.

International Report on Patentability for PCT/US2016/37280 dated Dec. 12, 2017, 8 pages.

Holly Kicks Fitness, What do the new additions in Shakeology even mean?, an article posted on, http://www.hollykicks.com/posts/what-do-the-new-additions-in-shakeology-even-mean/ Jul. 6, 2012.

Chocolate Shakeology Ingredients, a Shakeology product disclosed on te internet, http://fitdadchris.com/wp-content/uploads/2013/12/chocolate-shakeology-nutrition-facts.pdf Sep. 30, 2012.

Pure Advantage, MRP, Meal Replacement Shake, Chocolate, a product sold and advertised on the internet, http://www.iherb.com/pure-advantage-MRP-Meal-Replacement-Shake-Chocolate-3-lbs-1380-g/45475 May 21, 2013.

Green Chocolate Shakeology, a recipe post on the internet, http://www.web.archibe.org/web/20120224162957/http://happyhealthyfamily.com/healthy-smoothie-recipes-for-kids/green-chocolate-shakeology/ Feb. 24, 2012.

Vega One All Shake—Chocolate, a product sold and advertised on the internet, http://www.vitaminshoppe.com/p/vega-vega-one-all-in-one-shake-chocolate-30-9-oz-powder/eq-1031, Oct. 23, 2013.

Orgain—Organic Ready to Drink Meal Replacement Creamy Chocolate Fudge, a product sold and advertised on the internet, http://www.luckyvitamin.com/p-171744-orgain-organic-ready-to-drink-meal-replacement-creamy-chocolate-fudge-12-pack Nov. 4, 2011.

Kamo, 31 Super Foods That'll Super Charge Your Weight Loss, http://www.nutritionsecrets.com/31-super-foods-super-charge-weight-loss/ Jun. 16, 2015, pp. 1-21.

* cited by examiner

FIG. 1A

Mechanism of action
- ↓ Muscle acid/lactic acid (beta-alanine)
- ↑ Central nervous system (CNS) activity (green tea/natural low-dose caffeine)
- ↑ Muscle mitochondrial biogenesis (quercetin)
- ↓ Muscle inflammation (quercetin)
- ↑ Fuel (carbohydrate/fat) efficiency (quercetin)

Benefit
- ↑ Exercise performance
- ↑ Power output
- ↑ Focus/cognitive performance
- ↓ Muscle fatigue
- ↑ Energy (and perception of energy)
- ↑ Muscle recovery

FIG. 1B

Mechanism of action
- ↑ Fluid absorption (osmolality, hypotonic composition)
- → Maintain fluid balance (osmolality, hypotonic composition)
- ↑ Electrolyte replacement (sodium citrate, potassium citrate, calcium citrate, magnesium citrate)
- → Maintain electrolyte balance (sodium citrate, potassium citrate, calcium citrate, magnesium citrate)
- ↑ Blood acid buffering (citrate forms)
- ↑ Muscle mitochondrial biogenesis (quercetin)
- ↓ Muscle inflammation (quercetin)

Benefit
- ↑ Hydration
- ↑ Exercise performance/endurance
- ↑ Power output
- ↓ Fatigue
- ↑ Energy
- ↓ Muscle cramping
- ↓ Muscle soreness

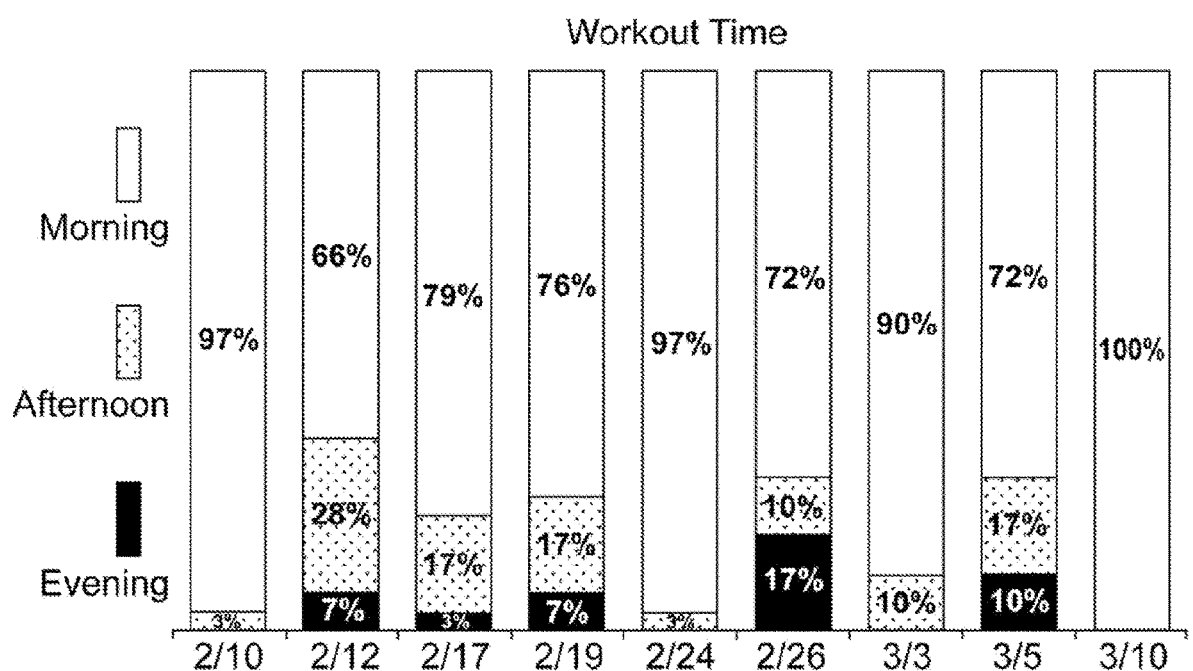

Energy Level
(Very Energized – Selected 4 or 5 on a 5-point scale)

Hydration
(Very Hydrated – Selected 4 or 5 on a 5-point scale)

Strength
(Very Strong – Selected 4 or 5 on a 5-point scale)

Motivation
(Ready and Motivated – Selected 4 or 5 on a 5-point scale)

Workout Performance
(Excellent– Selected 4 or 5 on a 5-point scale)

Pushing Self
(A Lot– Selected 4 or 5 on a 5-point scale)

Energy Level
(Very Energized – Selected 4 or 5 on a 5-point scale)

Hydration
(Very Hydrated – Selected 4 or 5 on a 5-point scale)

Focus
(Very Focused– Selected 4 or 5 on a 5-point scale)

Cramping
(Not at All – Selected 1 or 2 on a 5-point scale)

Feeling
(Great – Selected 4 or 5 on a 5-point scale)

Replenishment
(Very Replenished – Selected 4 or 5 on a 5-point scale)

Energy Level
*(Very Energized – Selected 4 or 5 on a 5-point scale)*

Recovery
*(Very Quickly – Selected 4 or 5 on a 5-point scale)*

Saw/Felt Difference in Muscle Definition*

Hunger
(Not Hungry at All – Selected 1 or 2 on a 5-point scale)

Replenishment
(Very Replenished – Selected 4 or 5 on a 5-point scale)

Muscle Soreness
(Not Sore at All – Selected 1 or 2 on a 5-point scale)

Hunger
(Not Hungry at All– Selected 1 or 2 on a 5-point scale)

Replenishment
(Very Replenished – Selected 4 or 5 on a 5-point scale)

Energy Level
(Very Energized – Selected 4 or 5 on a 5-point scale)

Refreshed
(Very Refreshed – Selected 4 or 5 on a 5-point scale)

Muscle Soreness After 1-2 Days
(Not Sore at All – Selected 1 or 2 on a 5-point scale)

Muscle Stiffness
(Not Stiff at All – Selected 1 or 2 on a 5-point scale)

COMPOSITIONS AND METHODS TO IMPROVE EXERCISE PERFORMANCE AND RECOVERY

CROSS-REFERENCE TO RELATED APPLICATIONS

This application is a National Phase of International Application No. PCT/US2016/037280, filed Jun. 13, 2016, which designated the U.S. and that International Application was published under PCT Article 21(2) in English. This application claims priority under 35 U.S.C. § 119(e) to U.S. provisional patent applications No. 62/174,405, No. 62/174,407, No. 62/174,419, and No. 62/174,421, all of which were filed on Jun. 11, 2015. The contents of all the related applications cross-referenced herein are herein incorporated by reference in their entirety as though fully set forth.

FIELD OF THE INVENTION

The invention relates to compositions, methods and kits for improving exercise performance and recovery.

BACKGROUND

All publications cited herein are incorporated by reference in their entirety to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Some problems or issues associated with exercise include: (1) muscle acid building up, ensuing muscle fatigue, and decline in exercise performance and power output; (2) reduced energy production by mitochondria and energy producing pathways (e.g., carbohydrate and fat oxidation and regulation); (3) increased muscle inflammation and damage, reduced adaptation to exercise, and increase in muscle recovery time; (4) reduced perception of energy, and increased perception of fatigue; (5) dehydration, reduced hydration status, and compromised exercise performance, and (6) jitters, nervousness, anxiety, the inability to sleep, or gastrointestinal distress from typical pre-exercise or energy drinks and powders.

Other problems or issues associated with exercise include: (1) drop in blood volume; (2) changes in fluid balance; (3) loss of electrolytes through sweat; (4) reduced endurance and performance; (5) reduced power output; (6) dehydration and reduced hydration status through exercise and/or high ambient temperatures resulting in compromised exercise performance; (7) gastrointestinal discomfort often associated with sports drinks; and (8) glycogen depletion and impaired performance during and/or after exercise.

Still other problems or issues associated with exercise include: (1) access and portability to effective level and form of protein to improve rapid and sustained recovery during post-exercise window; (2) balance of muscle protein synthesis (MPS) and muscle protein breakdown (MPB) directed towards net MPS enabling muscle recovery/synthesis vs. net MPB resulting in limited adaptations to exercise/or promoting muscle breakdown; (3) muscle inflammation from exercise and ensuing muscle soreness/delayed onset muscle soreness (DOMS) resulting in decline in exercise performance, strength recovery, and overall muscle recovery, and related psychological discomfort; and (4) alternative measure to reduce muscle soreness without the side effects of NSAIDS provided.

More problems or issues associated with exercise include: (1) access and portability to effective level and form of protein to improve post-exercise overnight recovery; (2) balance of muscle protein synthesis (MPS) and muscle protein breakdown (MPB) directed towards net MPS enabling muscle recovery/synthesis vs. net MPB resulting in limited adaptations to exercise/or promoting muscle breakdown; (3) muscle inflammation from exercise and ensuing muscle soreness/delayed onset muscle soreness (DOMS) resulting in decline in exercise performance, strength recovery, and overall muscle recovery, and related psychological discomfort; and (4) alternative measure to reduce muscle soreness without the side effects of NSAIDS provided.

To address these problems or issues, the present invention provides various compositions, methods and kits for improving exercise performance and recovery.

SUMMARY OF THE INVENTION

Various embodiments of the present invention provide a composition. The composition may consist of or may comprise or may consist essentially of one or more (e.g., at least 1, 2, 3, 4, 5, 6, 7, 8, 9, 10, 11, 12, 13, 14, or 15) or all of: sugar (e.g., glucose, fructose, galactose, maltose, lactose, and sucrose (for example, cane sugar and beet sugar)), citric acid, beta alanine, quercetin, sodium citrate, stevia and/or stevia leaf extract, fruit flavor (e.g., lemonade, lemon, orange, mandarin orange, pineapple, pearl, apple, grape, cherry, citrus and other fruit flavors), green tea extract and/or natural caffeine, sodium chloride, magnesium citrate, silicon dioxide, potassium citrate, calcium citrate, and dextrose. In various embodiments, the sugar (e.g., glucose, fructose, galactose, maltose, lactose, and sucrose (for example, cane sugar and beet sugar)) is granulated sugar. In various embodiments, the citric acid is citric acid granular. In various embodiments, the beta alanine is beta alanine compound solution. In various embodiments, the quercetin is quercetin anhydrous, quercetin 95%, quercetin 99.5%, or quercetin dehydrate. In various embodiments, the sodium citrate is sodium citrate (23% Na). In various embodiments, the fruit flavor is lemonade flavor. In various embodiments, the green tea extract and/or natural caffeine is green tea extract 50% natural caffeine. In various embodiments, the magnesium citrate is magnesium citrate 16% Mg. In various embodiments, the potassium citrate is potassium citrate 36% K or potassium citrate (35.6% K). In various embodiments, the calcium citrate is calcium citrate tetrahydrate.

Various embodiments of the present invention provide a composition. The composition may consist of or may comprise or may consist essentially of one or more (e.g., at least 1, 2, 3, 4, 5, 6, 7, 8, 9, 10, 11, 12, 13, 14, or 15) or all of: calcium, magnesium, sodium, potassium, beta-alanine, quercetin and caffeine. In various embodiments, the composition may further comprise one or more (e.g., at least 1, 2, 3, 4, 5, 6, 7, 8, 9, 10, 11, 12, 13, 14, or 15) or all of: sugar (e.g., glucose, fructose, galactose, maltose, lactose, and sucrose (for example, cane sugar and beet sugar)), citric acid, stevia leaf extract, fruit flavor (e.g., lemonade, lemon, orange, mandarin orange, pineapple, pearl, apple, grape, cherry, citrus and other fruit flavors) and silica. In various embodiments, the calcium is in the form of calcium citrate, and/or calcium chloride, and/or any other suitable calcium salts or calcium sources. In various embodiments, the magnesium is in the form of magnesium citrate, and/or magnesium chloride, and/or any other suitable magnesium salts or magnesium sources. In various embodiments, the sodium is in the form of sodium citrate, and/or sodium chloride, and/or any other suitable sodium salts or sodium sources. In various embodiments, the potassium is in the form of potassium citrate, and/or chloride, and/or any other suitable potassium salts or potassium sources. In various embodiments, the quercetin is quercetin anhydrous. In various embodiments, the natural caffeine is in the form of green tea extract and/or natural caffeine. In exemplary embodiments, per serving, the composition may consist of or may comprise or may consist essentially of one or more (e.g., at least 1, 2, 3, 4, 5, 6, 7, 8, 9, 10, 11, 12, 13, 14, or 15) or all of: about 5 mg calcium, about 20 mg magnesium, about 115 mg sodium, about 40 mg potassium, about 800 mg beta-alanine, about 500 mg quercetin, and about 200 mg green tea extract or about 100 mg natural caffeine. In exemplary embodiments, the composition may be used to improve exercise performance and/or recovery. In some embodiments, the effective amount of the composition to improve exercise performance and/or recovery is about 6 grams in a subject that weighs less than 160 lbs and about 12 grams in a subject that weighs 160 lbs or more. In some embodiments, the effective amount of the composition is dissolved in water. For example, in a subject that weighs less than 160 lbs, about 6 grams of the composition is dissolved in 8 ounces of water; or in a subject that weighs 160 lbs or more, about 12 grams of the composition is dissolved in 16 ounces of water. In some embodiments, the composition is consumed within 30 minutes prior to exercise.

Various embodiments of the present invention provide a composition. The composition may consist of or may comprise or may consist essentially of one or more (e.g., at least 1, 2, 3, 4, 5, 6, 7, 8, 9, 10, 11, 12, 13, 14, or 15) or all of: sugar (e.g., glucose, fructose, galactose, maltose, lactose, and sucrose (for example, cane sugar and beet sugar)), dextrose, sodium citrate, citric acid, quercetin, magnesium citrate, silicon dioxide, potassium citrate, calcium citrate, fruit flavor (e.g., lemonade, lemon, orange, mandarin orange, pineapple, pearl, apple, grape, cherry, citrus and other fruit flavors), and stevia and/or stevia leaf extract. In various embodiments, the sugar (e.g., glucose, fructose, galactose, maltose, lactose, and sucrose (for example, cane sugar and beet sugar)) is granulated sugar. In various embodiments, the citric acid is citric acid granular. In various embodiments, the quercetin is quercetin anhydrous, quercetin 95%, quercetin 99.5%, or quercetin dehydrate. In various embodiments, the magnesium citrate is magnesium citrate 16% Mg. In various embodiments, the potassium citrate is potassium citrate 36% K. In various embodiments, the calcium citrate is calcium citrate tetrahydrate. In various embodiments, the fruit flavor is natural orange or mandarin orange flavor.

Various embodiments of the present invention provide a composition. The composition may consist of or may comprise or may consist essentially of one or more (e.g., at least 1, 2, 3, 4, 5, 6, 7, 8, 9, 10, 11, 12, 13, 14, or 15) or all of: calcium, magnesium, sodium, potassium, and quercetin. The composition may further comprise one or more (e.g., at least 1, 2, 3, 4, 5, 6, 7, 8, 9, 10, 11, 12, 13, 14, or 15) or all of: sugar (e.g., glucose, fructose, galactose, maltose, lactose, and sucrose (for example, cane sugar and beet sugar)), dextrose, citric acid, silica, fruit flavor (e.g., lemonade, lemon, orange, mandarin orange, pineapple, pearl, apple, grape, cherry, citrus and other fruit flavors) and stevia leaf extract. In various embodiments, the fruit flavor is natural orange or mandarin orange flavor. In various embodiments, the calcium is in the form of calcium citrate, and/or calcium chloride, and/or any other suitable calcium salts or calcium sources. In various embodiments, the magnesium is in the form of magnesium citrate, and/or magnesium chloride, and/or any other suitable magnesium salts or magnesium sources. In various embodiments, the sodium is in the form of sodium citrate, and/or sodium chloride, and/or any other suitable sodium salts or sodium sources. In various embodiments, the potassium is in the form of potassium citrate, and/or chloride, and/or any other suitable potassium salts or potassium sources. In various embodiments, the quercetin is quercetin anhydrous. In exemplary embodiments, per serving, the composition may consist of or may comprise or may consist essentially of one or more (e.g., at least 1, 2, 3, 4, 5, 6, 7, 8, 9, 10, 11, 12, 13, 14, or 15) or all of: about 10 mg calcium, about 40 mg magnesium, about 230 mg sodium, about 80 mg potassium, and about 250 mg quercetin. In exemplary embodiments, the composition may be used to improve exercise performance and/or recovery. In some embodiments, the effective amount of the composition to improve exercise performance and/or recovery for exercise duration of 30 minutes is about 11.5 grams. In some embodiments, the effective amount of the composition to improve exercise performance and/or recovery for exercise duration of 60 minutes is about 23 grams. In some embodiments, the effective amount of the composition to improve exercise performance and/or recovery for exercise duration of 90 minutes is about 34.5 grams. In some embodiments, the effective amount of the composition is dissolved in water. For example, 11.5, 23, and 34.5 grams of the composition may respectively be dissolved in 8, 16, and 24 ounces of water. In some embodiments, the composition is consumed during exercise.

Various embodiments of the present invention provide a composition. The composition may consist of or may comprise or may consist essentially of one or more (e.g., at least 1, 2, 3, 4, 5, 6, 7, 8, 9, 10, 11, 12, 13, 14, or 15) or all of: whey protein, pea protein, sugar (e.g., glucose, fructose, galactose, maltose, lactose, and sucrose (for example, cane sugar and beet sugar)), casein, cocoa powder, potassium citrate, pomegranate extract, sodium chloride, chocolate flavor, xanthan gum, stevia and/or stevia leaf extract, L-glutamine, and branched-chain amino acids (BCAAs). In various embodiments, the whey protein is whey protein isolate 90%. In various embodiments, the pea protein is pea protein 80%—micronized. In various embodiments, the sugar (e.g., glucose, fructose, galactose, maltose, lactose, and sucrose (for example, cane sugar and beet sugar)) is granulated sugar. In various embodiments, the casein is micellar casein. In various embodiments, the cocoa powder is cocoa powder alkalized or cocoa powder (23% protein). In various embodiments, the potassium citrate is potassium citrate 36% K or potassium citrate (35.6% K). In various embodiments, the pomegranate extract is a high polyphenol pomegranate extract (e.g., POMx pomegranate extract and PomX pomegranate (75% polyphenols)). In various embodiments, the sodium chloride is sodium chloride (39% Na). In various embodiments, the chocolate flavor is natural chocolate flavor. In various embodiments, the L-glutamine is L-glutamine FCC. In various embodiments, the BCAA is BCAA 2:1:1.

Various embodiments of the present invention provide a composition. The composition may consist of or may comprise or may consist essentially of one or more (e.g., at least 1, 2, 3, 4, 5, 6, 7, 8, 9, 10, 11, 12, 13, 14, or 15) or all of: calcium, magnesium, sodium, potassium, pomegranate extract and a combination of whey protein isolate, pea protein isolate, micellar casein, branched chain amino acids (BCAAs), L-leucine, valine, isoleucine and L-glutamine. The composition may further comprise one or more (e.g., at least 1, 2, 3, 4, 5, 6, 7, 8, 9, 10, 11, 12, 13, 14, or 15) or all of: sugar (e.g., glucose, fructose, galactose, maltose, lactose, and sucrose (for example, cane sugar and beet sugar)), cocoa powder, chocolate flavor, xanthan gum and stevia leaf extract. In various embodiments, the calcium is in the form of calcium citrate, and/or calcium chloride, and/or any other suitable calcium salts or calcium sources. In various embodiments, the magnesium is in the form of magnesium citrate, and/or magnesium chloride, and/or any other suitable magnesium salts or magnesium sources. In various embodiments, the sodium is in the form of sodium citrate, and/or sodium chloride, and/or any other suitable sodium salts or sodium sources. In various embodiments, the potassium is in the form of potassium citrate, and/or chloride, and/or any other suitable potassium salts or potassium sources. In some embodiments, L-leucine, valine and isoleucine are at a ratio of 2:1:1. In exemplary embodiments, per serving, the composition may consist of or may comprise or may consist essentially of one or more (e.g., at least 1, 2, 3, 4, 5, 6, 7, 8, 9, 10, 11, 12, 13, 14, or 15) or all of: about 140 mg calcium, about 40 mg magnesium, about 300 mg sodium, about 420 mg potassium, about 650 mg pomegranate extract, and about 23 g of the combination of whey protein isolate, pea protein isolate, micellar casein, branched chain amino acids (BCAAs), L-leucine, valine, isoleucine and L-glutamine. In exemplar embodiments, the composition may be used to improve exercise recovery. In some embodiments, the effective amount of the composition to improve exercise recovery is about 35.5 grams. In some embodiments, the effective amount of the composition is dissolved in water. For example, 35.5 grams of the composition may be dissolved in 8 ounces of water. In some embodiments, the composition is consumed after exercise, for example, within 30 minutes after exercise.

Various embodiments of the present invention provide a composition. The composition may consist of or may comprise or may consist essentially of one or more (e.g., at least 1, 2, 3, 4, 5, 6, 7, 8, 9, 10, 11, 12, 13, 14, or 15) or all of: casein, sugar (e.g., glucose, fructose, galactose, maltose, lactose, and sucrose (for example, cane sugar and beet sugar)), vanilla flavor, tart cherry extract, sodium chloride, branched-chain amino acids (BCAAs), L-glutamine, stevia and/or stevia leaf extract, and xanthan gum. In various embodiments, the casein is micellar casein. In various embodiments, the sugar (e.g., glucose, fructose, galactose, maltose, lactose, and sucrose (for example, cane sugar and beet sugar)) is granulated sugar. In various embodiments, the vanilla flavor is natural vanilla flavor, natural vanilla chamomile flavor or vanilla chamomile wild flavor. In various embodiments, the BCAA is BCAA 2:1:1.

Various embodiments of the present invention provide a composition. The composition may consist of or may comprise or may consist essentially of one or more (e.g., at least 1, 2, 3, 4, 5, 6, 7, 8, 9, 10, 11, 12, 13, 14, or 15) or all of: calcium, magnesium, sodium, potassium, tart cherry powder and a combination of micellar casein, branched chain amino acids (BCAAs), L-leucine, valine, isoleucine and L-glutamine. The composition may further comprise one or more (e.g., at least 1, 2, 3, 4, 5, 6, 7, 8, 9, 10, 11, 12, 13, 14, or 15) or all of: sugar (e.g., glucose, fructose, galactose, maltose, lactose, and sucrose (for example, cane sugar and beet sugar)), vanilla flavor, stevia leaf extract and xanthan gum. In various embodiments, the calcium is in the form of calcium citrate, and/or calcium chloride, and/or any other suitable calcium salts or calcium sources. In various embodiments, the magnesium is in the form of magnesium citrate, and/or magnesium chloride, and/or any other suitable magnesium salts or magnesium sources. In various embodiments, the sodium is in the form of sodium citrate, and/or sodium chloride, and/or any other suitable sodium salts or sodium sources. In various embodiments, the potassium is in the form of potassium citrate, and/or chloride, and/or any other suitable potassium salts or potassium sources. In some embodiments, L-leucine, valine and isoleucine are at a ratio of 2:1:1. In exemplary embodiments, per serving, the composition may consist of or may comprise or may consist essentially of one or more (e.g., at least 1, 2, 3, 4, 5, 6, 7, 8, 9, 10, 11, 12, 13, 14, or 15) or all of: about 420 mg calcium, about 15 mg magnesium, about 80 mg sodium, about 50 mg potassium, about 480 mg tart cherry powder, and about 23 g of the combination of micellar casein, branched chain amino acids (BCAAs), L-leucine, valine, isoleucine and L-glutamine. In exemplar embodiments, the composition may be used to improve exercise recovery. In some embodiments, the effective amount of the composition to improve exercise recovery is about 28.5 grams. In some embodiments, the effective amount of the composition is dissolved in water. For example, 28.5 grams of the composition may be dissolved in 8 ounces of water. In some embodiments, the composition is consumed before sleep, for example, within 1 hour before sleep.

Various embodiments of the present invention provide a method for improving exercise performance and/or recovery in a subject. The method may consist of or may comprise or may consist essentially of: providing a composition as disclosed herein; and administering an effective amount of the composition to the subject, thereby improving exercise performance and/or recovery in the subject. In various embodiments, the composition is administered to the subject before exercise. In various embodiments, the composition is administered to the subject during exercise. In various embodiments, the composition is administered to the subject after exercise. In various embodiments, the composition is administered to the subject before sleep. In various embodiments, the composition is administered to the subject after exercise and before sleep.

Various embodiments of the present invention provide a kit for improving exercise performance and/or recovery in a subject. The kit may consist of or may comprise or may consist essentially of: a composition as disclosed herein; and instructions for using the composition to improve exercise performance and/or recovery in the subject.

Various embodiments of the present invention provide a method for controlling body weight and/or for promoting weight loss in a subject. The method may consist of or may comprise or may consist essentially of: providing a composition as disclosed herein;
administering an effective amount of the composition to the subject, and subjecting the subject to an exercise after administering the effective amount of the composition, thereby controlling body weight and/or for promoting weight loss in the subject.

Various embodiments of the present invention provide a method for controlling body weight and/or for promoting weight loss in a subject. The method may consist of or may comprise or may consist essentially of: providing a composition as disclosed herein; subjecting the subject to an exercise; and administering an effective amount of the composition to the subject during the exercise, thereby controlling body weight and/or for promoting weight loss in the subject.

Various embodiments of the present invention provide a method for controlling body weight and/or for promoting lean muscle growth in a subject. The method may consist of or may comprise or may consist essentially of: providing a composition as disclosed herein; subjecting the subject to an exercise; and administering an effective amount of the composition to the subject after the exercise, thereby controlling body weight and/or for promoting lean muscle growth in the subject.

Various embodiments of the present invention provide a method for controlling body weight and/or for promoting lean muscle growth in a subject. The method may consist of or may comprise or may consist essentially of: providing a composition as disclosed herein; subjecting the subject to an exercise; and administering an effective amount of the composition to the subject after the exercise and before sleep, thereby controlling body weight and/or for promoting lean muscle growth in the subject.

Various embodiments of the present invention provide a kit for controlling body weight and/or for promoting weight loss in a subject. The kit may consist of or may comprise or may consist essentially of: a composition as disclosed herein; and instructions for using the composition and an exercise to control body weight and/or promote weight loss in the subject.

Various embodiments of the present invention provide a kit for controlling body weight and/or for promoting lean muscle growth in a subject. The kit may consist of or may comprise or may consist essentially of: a composition as disclosed herein; and instructions for using the composition and an exercise to control body weight and/or promote lean muscle growth in the subject.

BRIEF DESCRIPTION OF THE DRAWINGS

Exemplary embodiments are illustrated in referenced figures. It is intended that the embodiments and figures disclosed herein are to be considered illustrative rather than restrictive.

FIGS. 1A-1D illustrate, in accordance with various embodiments of the invention, while not wishing to be bound by any particular theory, various mechanisms of action.

FIGS. 2-33 illustrate, in accordance with various embodiments of the invention, a test group survey data and analysis including survey feedback and/or changes in weight loss and/or body composition. An asterisk "*" indicates that a question was not asked in baseline survey.

DETAILED DESCRIPTION OF THE INVENTION

Figure 1C:
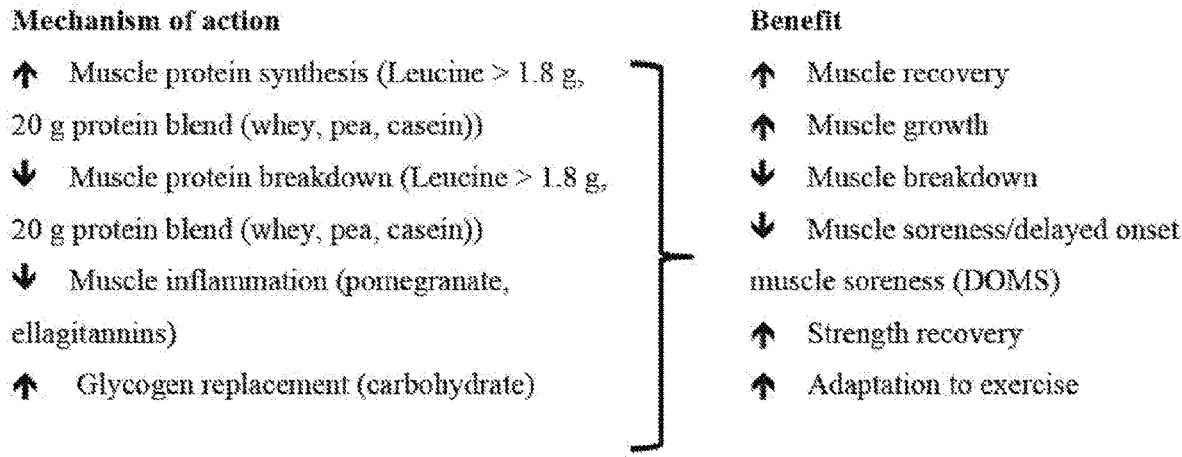

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* $22^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* $3^{rd}$ ed., revised ed., J. Wiley & Sons (New York, N.Y. 2006); Smith, *March's Advanced Organic Chemistry Reactions, Mechanisms and Structure* $7^{th}$ ed., J. Wiley & Sons (New York, N.Y. 2013); Singleton, *Dictionary of DNA and Genome Technology* $3^{rd}$ ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, N.Y. 2012), provide one skilled in the art with a general guide to many of the terms used in the present application. For references on how to prepare antibodies, see Greenfield, *Antibodies A Laboratory Manual* $2^{nd}$ ed., Cold Spring Harbor Press (Cold Spring Harbor N.Y., 2013); Köhler and Milstein, *Derivation of specific antibody-producing tissue culture and tumor lines by cell fusion*, Eur. J. Immunol. 1976 July, 6(7):511-9; Queen and Selick, Humanized immunoglobulins, U.S. Pat. No. 5,585,089 (1996 December); and Riechmann et al., *Reshaping human antibodies for therapy*, Nature 1988 Mar. 24, 332(6162):323-7.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

As used herein, a "subject" means a human or animal. The terms "individual" and "subject" are used interchangeably herein. In an embodiment, the subject is a mammal, and in another embodiment, is human.

The term "statistically significant" or "significantly" refers to statistical evidence that there is a difference. It is defined as the probability of making a decision to reject the null hypothesis when the null hypothesis is actually true. The decision is often made using the p-value.

As used herein, the term "administering" refers to the placement of a composition as disclosed herein into a subject by a method or route which results in at least partial localization of the composition at a desired site. "Route of administration" may refer to any administration pathway known in the art, including but not limited to aerosol, nasal, oral, transmucosal, transdermal, parenteral, enteral, topical or local. Via the enteral route, the compositions can be in the form of tablets, gel capsules, sugar-coated tablets, syrups, suspensions, solutions, powders, granules, emulsions, microspheres or nanospheres or lipid vesicles or polymer vesicles allowing controlled release. In an embodiment, the compositions are provided in a powder form and mixed with a liquid, such as water, to form a beverage. In accordance with the present invention, "administering" can be self-administering. For example, it is considered as "administering" that a subject consumes a composition as disclosed herein.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

The present invention provides various compositions (i.e., the formulas described herein) for improving exercise performance and/or recovery. The compositions may include one or more types of ingredients, including but not limited to plant products, algae, vitamins, minerals, protein sources, sulfur sources, and other nutrients.

Examples of plant products include but are not limited to Barley grass, Kamut grass, Hydrilla, Spinach, Whole flax seed meal, Chia seed, Grape seed extract, Pea fiber, Wheat grass, Oat grass, Sprouted amaranth, Sprouted quinoa, Green tea extract, Yacon root, Sacha inchi, and Apple fiber. Other plant products which provide beneficial phytochemicals and nutrients that the body needs may be used as well. The compositions described herein may include one or more plant products. The plant products may be provided in powdered form. The plant products may be provided as a blend or mixture.

Examples of algae include but are not limited to Blue green algae, *Chlorella*, and *Spirulina*. Other algae species which have similar beneficial effects as the ones listed here may be used as well. The compositions described herein may include one or more algae species. The algae may be provided in powdered form. The algae may be provided as a blend or mixture.

Example of vitamins and minerals include but are not limited to Vitamin A (as beta carotene and palmitate), Vitamin C (as ascorbic acid), Vitamin D (as cholecalciferol), Vitamin E (as d-alpha tocopheryl succinate), Vitamin K1 (as phytonadione), Vitamin B1 (as thiamin HCl and mononitrate), Calcium (as dicalcium phosphate), Phosphorus (as dicalcium phosphate), Magnesium (as oxide), Copper (as copper oxide and AA chelate), Chromium (as chromium amino acid chelate and picolinate), Vitamin B2 (as riboflavin), Vitamin B3 (as riacin), Vitamin B6 (as pyridoxine HCl), Vitamin B12, Biotin, Pantothenic acid (as d-calcium pantothenate), Iodine (as kelp and potassium iodine), Zinc (as zinc oxide and sulfate), Manganese (as manganese amino acid chelate), and Molybdenum (as sodium molybdenate). The compositions described herein may include one or more vitamins and minerals. The vitamins and minerals may be provided in powdered form. The vitamins and minerals may be provided as a blend or mixture.

Example of protein sources include but are not limited to pea protein, casein, and whey protein (isolate). One non-limiting example of sulfur sources is methylsulfonylmethane (MSM).

Various flavor ingredients may be added to enhance the flavor of the composition, such as fruit powders. In one embodiment, a fruity or berry flavor may be imparted on the composition by adding any one or a combination of banana, carrot, orange, pineapple, raspberry, and strawberry powders. In another embodiment, a chocolate flavor may be imparted by adding any one or a combination of chocolate, cocoa, and cinnamon powders. The relative concentration the flavor ingredients in the formulation may be altered based on the desired taste. It is understood that additional ingredients may be added as flavor ingredients, so long as they do not interfere with composition's effect of improving exercise performance and/or recovery.

In various embodiments, the quercetin ingredient used in a composition as described herein has a potency or purity of about 70-75%, 75-80%, 80-85%, 85-90%, 90-95%, or 95-100% for quercetin. In certain embodiments, the quercetin ingredient used in a composition as described herein is quercetin 95%. In certain embodiments, the quercetin ingredient used in a composition as described herein is quercetin 99.5%.

In various embodiments, the pomegranate extract/powder ingredient used in a composition as described herein has a potency or purity of about 50-55%, 55-60%, 60-65%, 65-70%, 70-75%, 75-80%, 80-85%, 85-90%, 90-95%, or 95-100% for polyphenols. In certain embodiments, the pomegranate extract/powder ingredient used in a composition as described herein is pomegranate extract/extract 75% polyphenols.

In various embodiments, the tart cherry extract/powder ingredient used in a composition as described herein has a potency or purity of about 70-75%, 75-80%, 80-85%, 85-90%, 90-95%, or 95-100% for anthocyanins. In certain embodiments, the tart cherry extract/powder ingredient used in a composition as described herein is tart cherry extract/powder 85% anthocyanins.

In various embodiments, the green tea extract/powder (or natural caffeine) ingredient used in a composition as described herein has a potency or purity of about 25-30%, 30-35%, 35-40%, 40-45%, 45-50%, 50-55%, 55-60%, 60-65%, 65-70%, or 70-75% for caffeine. In certain embodiments, the green tea extract/powder (or natural caffeine) ingredient used in a composition as described herein is green tea extract 50% natural caffeine.

In various embodiments, the whey protein (or whey protein isolate) ingredient used in a composition as described herein has a potency or purity of about 70-75%, 75-80%, 80-85%, 85-90%, 90-95%, or 95-100% for protein. In certain embodiments, the whey protein (or whey protein isolate) ingredient used in a composition as described herein is whey protein isolate 90%.

In various embodiments, the pea protein (or pea protein isolate) ingredient used in a composition as described herein has a potency or purity of about 60-65%, 65-70%, 70-75%, 75-80%, 80-85%, 85-90%, 90-95%, or 95-100% for protein. In some embodiments, the pea protein (or pea protein isolate) ingredient used in a composition as described herein is pea protein 80%. In some embodiments, the pea protein ingredient used in a composition as described herein is micronized. In some embodiments, the pea protein (or pea protein isolate) ingredient used in a composition as described herein is pea protein 80%—micronized.

In various embodiments, the cocoa powder ingredient used in a composition as described herein has a potency or purity of about 5-10%, 10-15%, 15-20%, 20-23%, 23-25%, 25-30%, 30-35%, or 35-40% for protein. In certain embodiments, the cocoa powder ingredient used in a composition as described herein is cocoa powder 23% protein.

In various embodiments, the magnesium citrate ingredient used in a composition as described herein has a potency or purity of about 5-10%, 10-15%, 15-16%, 16-20%, 20-25%, or 25-30%, for Mg. In certain embodiments, the magnesium citrate ingredient used in a composition as described herein is magnesium citrate 16% Mg.

In various embodiments, the sodium citrate ingredient used in a composition as described herein has a potency or purity of about 5-10%, 10-15%, 15-20%, 20-23%, 23-25%, 25-30%, 30-35%, or 35-40% for Na. In certain embodiments, the sodium citrate ingredient used in a composition as described herein is sodium citrate 23% Na.

In various embodiments, the sodium chloride ingredient used in a composition as described herein has a potency or purity of about 20-25%, 25-30%, 30-35%, 35-39%, 39-40%, 40-45%, 45-50%, or 50-55% for Na. In certain embodiments, the sodium chloride ingredient used in a composition as described herein is sodium chloride 39% Na.

In various embodiments, the potassium citrate ingredient used in a composition as described herein has a potency or purity of about 20-25%, 25-30%, 30-35%, 35-36%, 36-40%, 40-45%, 45-50% or 50-55% for K. In certain embodiments, the potassium citrate ingredient used in a composition as described herein is potassium citrate 36% K.

Compositions of the Invention
Before Exercise

In various embodiments, the present invention provides a composition for improving exercise performance and/or recovery. Ingredients of the composition may include but are not limited to sugar (e.g., glucose, fructose, galactose, maltose, lactose, and sucrose (for example, cane sugar and beet sugar)), citric acid, beta alanine, quercetin, sodium citrate, stevia and/or stevia leaf extract, fruit flavor (e.g., lemonade, lemon, orange, mandarin orange, pineapple, pearl, apple, grape, cherry, citrus and other fruit flavors), green tea extract and/or natural caffeine, sodium chloride, magnesium citrate, silicon dioxide, potassium citrate, calcium citrate, and dextrose.

In various embodiments, the present invention provides a composition for improving exercise performance and/or recovery. The composition may consist of or may comprise or may consist essentially of one or more or all of: sugar (e.g., glucose, fructose, galactose, maltose, lactose, and sucrose (for example, cane sugar and beet sugar)), citric acid, beta alanine, quercetin, sodium citrate, stevia and/or stevia leaf extract, fruit flavor (e.g., lemonade, lemon, orange, mandarin orange, pineapple, pearl, apple, grape, cherry, citrus and other fruit flavors), green tea extract and/or natural caffeine, sodium chloride, magnesium citrate, silicon dioxide, potassium citrate, calcium citrate, and dextrose.

In various embodiments, the present invention provides a composition for improving exercise performance and/or recovery. The composition may consist of or may comprise or may consist essentially of one or more or all of: sugar (e.g., glucose, fructose, galactose, maltose, lactose, and sucrose (for example, cane sugar and beet sugar)), citric acid, beta alanine, quercetin, sodium citrate, stevia and/or stevia leaf extract, fruit flavor (e.g., lemonade, lemon, orange, mandarin orange, pineapple, pearl, apple, grape, cherry, citrus and other fruit flavors), green tea extract and/or natural caffeine, sodium chloride, magnesium citrate, silicon dioxide, potassium citrate, and calcium citrate.

In various embodiments, the present invention provides a composition for improving exercise performance and/or recovery. The composition may consist of or may comprise or may consist essentially of one or more or all of: citric acid, beta alanine, quercetin, sodium citrate, stevia and/or stevia leaf extract, fruit flavor (e.g., lemonade, lemon, orange, mandarin orange, pineapple, pearl, apple, grape, cherry, citrus and other fruit flavors), green tea extract and/or natural caffeine, potassium citrate, and dextrose.

In various embodiments, the sugar (e.g., glucose, fructose, galactose, maltose, lactose, and sucrose (for example, cane sugar and beet sugar)) is granulated sugar. In various embodiments, the citric acid is citric acid granular. In various embodiments, the beta alanine is beta alanine compound solution. In various embodiments, the quercetin is quercetin anhydrous, quercetin 95%, quercetin 99.5%, or quercetin dehydrate. In various embodiments, the sodium citrate is sodium citrate (23% Na). In various embodiments, the fruit flavor is lemonade flavor. In various embodiments, the green tea extract and/or natural caffeine is green tea extract 50% natural caffeine. In various embodiments, the magnesium citrate is magnesium citrate 16% Mg. In various embodiments, the potassium citrate is potassium citrate 36% K or potassium citrate (35.6% K). In various embodiments, the calcium citrate is calcium citrate tetrahydrate.

In various embodiments, the present invention provides a composition for improving exercise performance and/or recovery. The composition may consist of or may comprise or may consist essentially of one or more or all of: granulated sugar (e.g., glucose, fructose, galactose, maltose, lactose, and sucrose (for example, cane sugar and beet sugar)), citric acid granular, beta alanine, quercetin anhydrous, sodium citrate, stevia, fruit flavor (e.g., lemonade, lemon, orange, mandarin orange, pineapple, pearl, apple, grape, cherry, citrus and other fruit flavors), green tea extract, sodium chloride, magnesium citrate, silicon dioxide, potassium citrate, and calcium citrate tetrahydrate.

In various embodiments, the present invention provides a composition for improving exercise performance and/or recovery. The composition may consist of or may comprise or may consist essentially of one or more or all of: citric acid, beta alanine compound solution, quercetin, sodium citrate, stevia, fruit flavor (e.g., lemonade, lemon, orange, mandarin orange, pineapple, pearl, apple, grape, cherry, citrus and other fruit flavors), green tea extract, potassium citrate, and dextrose.

In various embodiments, the composition may comprise, or may consist essentially of, or may consist of sugar (e.g., glucose, fructose, galactose, maltose, lactose, and sucrose (for example, cane sugar and beet sugar)) at about 30.3-31.9%, 31.9-33.4%, 33.4-34.9%, 34.9-36.4%, 36.4-37.9%, 37.9-39.4%, 39.4-41.0%, 41.0-42.5%, 42.5-44.0%, or 44.0-45.5%, or about 37.9% by weight or volume. In various embodiments, the composition may comprise, or may consist essentially of, or may consist of citric acid at about 13.3-14.0%, 14.0-14.7%, 14.7-15.3%, 15.3-16.0%, 16.0-16.7%, 16.7-17.3%, 17.3-18.0%, 18.0-18.7%, 18.7-19.3%, or 19.3-20.0%, or about 16.7% by weight or volume. In various embodiments, the composition may comprise, or may consist essentially of, or may consist of beta alanine at about 10.7-11.2%, 11.2-11.7%, 11.7-12.3%, 12.3-12.8%, 12.8-13.3%, 13.3-13.9%, 13.9-14.4%, 14.4-14.9%, 14.9-15.5%, or 15.5-16.0%, or about 13.3% by weight or volume. In various embodiments, the composition may comprise, or may consist essentially of, or may consist of quercetin at about 6.70-7.04%, 7.04-7.37%, 7.37-7.71%, 7.71-8.04%, 8.04-8.38%, 8.38-8.71%, 8.71-9.05%, 9.05-9.38%, 9.38-9.72%, or 9.72-10.05%, or about 8.38% by weight or volume. In various embodiments, the composition may comprise, or may consist essentially of, or may consist of sodium citrate at about 3.77-3.96%, 3.96-4.14%, 4.14-4.33%, 4.33-4.52%, 4.52-4.71%, 4.71-4.90%, 4.90-5.09%, 5.09-5.28%, 5.28-5.46%, or 5.46-5.65%, or about 4.71% by weight or volume. In various embodiments, the composition may comprise, or may consist essentially of, or may consist of stevia and/or stevia extract at about 3.07-3.22%, 3.22-3.37%, 3.37-3.53%, 3.53-3.68%, 3.68-3.83%, 3.83-3.99%, 3.99-4.14%, 4.14-4.29%, 4.29-4.45%, or 4.45-4.60%, or about 3.83% by weight or volume. In various embodiments, the composition may comprise, or may consist essentially of, or may consist of fruit flavor (e.g., lemonade, lemon, orange, mandarin orange, pineapple, pearl, apple, grape, cherry, citrus and other fruit flavors) at about 2.67-2.80%, 2.80-2.93%, 2.93-3.07%, 3.07-3.20%, 3.20-3.33%, 3.33-3.47%, 3.47-3.60%, 3.60-3.73%, 3.73-3.87%, or 3.87-4.00%, or about 3.33% by weight or volume. In various embodiments, the composition may comprise, or may consist essentially of, or may consist of green tea extract and/or natural caffeine at about 2.67-2.80%, 2.80-2.93%, 2.93-3.07%, 3.07-3.20%, 3.20-3.33%, 3.33-3.47%, 3.47-3.60%, 3.60-3.73%, 3.73-3.87%, or 3.87-4.00%, or about 3.33% by weight or volume. In various embodiments, the composition may comprise, or may consist essentially of, or may consist of sodium chloride at about 1.71-1.79%, 1.79-1.88%, 1.88-1.97%, 1.97-2.05%, 2.05-2.14%, 2.14-2.22%, 2.22-2.31%, 2.31-2.39%, 2.39-2.48%, or 2.48-2.56%, or about 2.14% by weight or volume. In various embodiments, the composition may comprise, or may consist essentially of, or may consist of magnesium citrate at about 1.67-1.75%, 1.75-1.83%, 1.83-1.92%, 1.92-2.00%, 2.00-2.08%, 2.08-2.17%, 2.17-2.25%, 2.25-2.33%, 2.33-2.42%, or 2.42-2.50%, or about 2.08% by weight or volume. In various embodiments, the composition may comprise, or may consist essentially of, or may consist of silicon dioxide at about 1.60-1.68%, 1.68-1.76%, 1.76-1.84%, 1.84-1.92%, 1.92-2.00%, 2.00-2.08%, 2.08-2.16%, 2.16-2.24%, 2.24-2.32%, or 2.32-2.40%, or about 2.00% by weight or volume. In various embodiments, the composition may comprise, or may consist essentially of, or may consist of potassium citrate at about 1.50-1.57%, 1.57-1.65%, 1.65-1.72%, 1.72-1.80%, 1.80-1.87%, 1.87-1.95%, 1.95-2.02%, 2.02-2.10%, 2.10-2.17%, or 2.17-2.25%, or about 1.87% by weight or volume. In various embodiments, the composition may comprise, or may consist essentially of, or may consist of calcium citrate at about 0.317-0.333%, 0.333-0.349%, 0.349-0.365%, 0.365-0.381%, 0.381-0.397%, 0.397-0.413%, 0.413-0.429%, 0.429-0.444%, 0.444-0.460%, or 0.460-0.476%, or about 0.397% by weight or volume. In some embodiments, the composition may consist of or may comprise or may consist essentially of one or more or all of these ingredients. In other embodiments, the composition may consist of or may comprise or may consist essentially of all of these ingredients.

In various embodiments, one serving of a composition described herein may consist of or may comprise or may consist essentially of one or more or all of: sugar (e.g., glucose, fructose, galactose, maltose, lactose, and sucrose (for example, cane sugar and beet sugar)) at about 30.3-31.9%, 31.9-33.4%, 33.4-34.9%, 34.9-36.4%, 36.4-37.9%, 37.9-39.4%, 39.4-41.0%, 41.0-42.5%, 42.5-44.0%, or 44.0-45.5%, or about 37.9% by weight or volume; citric acid at about 13.3-14.0%, 14.0-14.7%, 14.7-15.3%, 15.3-16.0%, 16.0-16.7%, 16.7-17.3%, 17.3-18.0%, 18.0-18.7%, 18.7-19.3%, or 19.3-20.0%, or about 16.7% by weight or volume; beta alanine at about 10.7-11.2%, 11.2-11.7%, 11.7-12.3%, 12.3-12.8%, 12.8-13.3%, 13.3-13.9%, 13.9-14.4%, 14.4-14.9%, 14.9-15.5%, or 15.5-16.0%, or about 13.3% by weight or volume; quercetin at about 6.70-7.04%, 7.04-7.37%, 7.37-7.71%, 7.71-8.04%, 8.04-8.38%, 8.38-8.71%, 8.71-9.05%, 9.05-9.38%, 9.38-9.72%, or 9.72-10.05%, or about 8.38% by weight or volume; sodium citrate at about 3.77-3.96%, 3.96-4.14%, 4.14-4.33%, 4.33-4.52%, 4.52-4.71%, 4.71-4.90%, 4.90-5.09%, 5.09-5.28%, 5.28-5.46%, or 5.46-5.65%, or about 4.71% by weight or volume; stevia and/or stevia extract at about 3.07-3.22%, 3.22-3.37%, 3.37-3.53%, 3.53-3.68%, 3.68-3.83%, 3.83-3.99%, 3.99-4.14%, 4.14-4.29%, 4.29-4.45%, or 4.45-4.60%, or about 3.83% by weight or volume; fruit flavor (e.g., lemonade, lemon, orange, mandarin orange, pineapple, pearl, apple, grape, cherry, citrus and other fruit flavors) at about 2.67-2.80%, 2.80-2.93%, 2.93-3.07%, 3.07-3.20%, 3.20-3.33%, 3.33-3.47%, 3.47-3.60%, 3.60-3.73%, 3.73-3.87%, or 3.87-4.00%, or about 3.33% by weight or volume; green tea extract and/or natural caffeine at about 2.67-2.80%, 2.80-2.93%, 2.93-3.07%, 3.07-3.20%, 3.20-3.33%, 3.33-3.47%, 3.47-3.60%, 3.60-3.73%, 3.73-3.87%, or 3.87-4.00%, or about 3.33% by weight or volume; sodium chloride at about 1.71-1.79%, 1.79-1.88%, 1.88-1.97%, 1.97-2.05%, 2.05-2.14%, 2.14-2.22%, 2.22-2.31%, 2.31-2.39%, 2.39-2.48%, or 2.48-2.56%, or about 2.14% by weight or volume; magnesium citrate at about 1.67-1.75%, 1.75-1.83%, 1.83-1.92%, 1.92-2.00%, 2.00-2.08%, 2.08-2.17%, 2.17-2.25%, 2.25-2.33%, 2.33-2.42%, or 2.42-2.50%, or about 2.08% by weight or volume; silicon dioxide at about 1.60-1.68%, 1.68-1.76%, 1.76-1.84%, 1.84-1.92%, 1.92-2.00%, 2.00-2.08%, 2.08-2.16%, 2.16-2.24%, 2.24-2.32%, or 2.32-2.40%, or about 2.00% by weight or volume; potassium citrate at about 1.50-1.57%, 1.57-1.65%, 1.65-1.72%, 1.72-1.80%, 1.80-1.87%, 1.87-1.95%, 1.95-2.02%, 2.02-2.10%, 2.10-2.17%, or 2.17-2.25%, or about 1.87% by weight or volume; and calcium citrate at about 0.317-0.333%, 0.333-0.349%, 0.349-0.365%, 0.365-0.381%, 0.381-0.397%, 0.397-0.413%, 0.413-0.429%, 0.429-0.444%, 0.444-0.460%, or 0.460-0.476%, or about 0.397% by weight or volume. In some embodiments, the composition may consist of or may comprise or may consist essentially of one or more or all of these ingredients. In other embodiments, the composition may consist of or may comprise or may consist essentially of all of these ingredients.

In various embodiments, the composition may comprise, or may consist essentially of, or may consist of citric acid at about 8.4-8.8%, 8.8-9.3%, 9.3-9.7%, 9.7-10.1%, 10.1-10.5%, 10.5-10.9%, 10.9-11.4%, 11.4-11.8%, 11.8-12.2%, or 12.2-12.6%, or about 10.5% by weight or volume. In various embodiments, the composition may comprise, or may consist essentially of, or may consist of beta alanine at about 13.5-14.1%, 14.1-14.8%, 14.8-15.5%, 15.5-16.2%, 16.2-16.8%, 16.8-17.5%, 17.5-18.2%, 18.2-18.9%, 18.9-19.5%, or 19.5-20.2%, or about 16.8% by weight or volume. In various embodiments, the composition may comprise, or may consist essentially of, or may consist of quercetin at about 4.43-4.65%, 4.65-4.88%, 4.88-5.10%, 5.10-5.32%, 5.32-5.54%, 5.54-5.76%, 5.76-5.98%, 5.98-6.21%, 6.21-6.43%, or 6.43-6.65%, or about 5.54% by weight or volume. In various embodiments, the composition may comprise, or may consist essentially of, or may consist of sodium citrate at about 8.4-8.8%, 8.8-9.3%, 9.3-9.7%, 9.7-10.1%, 10.1-10.5%, 10.5-10.9%, 10.9-11.4%, 11.4-11.8%, 11.8-12.2%, or 12.2-12.6%, or about 10.5% by weight or volume. In various embodiments, the composition may comprise, or may consist essentially of, or may consist of stevia and/or stevia extract at about 1.94-2.03%, 2.03-2.13%, 2.13-2.23%, 2.23-2.32%, 2.32-2.42%, 2.42-2.52%, 2.52-2.61%, 2.61-2.71%, 2.71-2.81%, or 2.81-2.91%, or about 2.42% by weight or volume. In various embodiments, the composition may comprise, or may consist essentially of, or may consist of fruit flavor (e.g., lemonade, lemon, orange, mandarin orange, pineapple, pearl, apple, grape, cherry, citrus and other fruit flavors) at about 1.68-1.77%, 1.77-1.85%, 1.85-1.94%, 1.94-2.02%, 2.02-2.11%, 2.11-2.19%, 2.19-2.27%, 2.27-2.36%, 2.36-2.44%, or 2.44-2.53%, or about 2.11% by weight or volume. In various embodiments, the composition may comprise, or may consist essentially of, or may consist of green tea extract and/or natural caffeine at about 1.68-1.77%, 1.77-1.85%, 1.85-1.94%, 1.94-2.02%, 2.02-2.11%, 2.11-2.19%, 2.19-2.27%, 2.27-2.36%, 2.36-2.44%, or 2.44-2.53%, or about 2.11% by weight or volume. In various embodiments, the composition may comprise, or may consist essentially of, or may consist of potassium citrate at about 8.4-8.8%, 8.8-9.3%, 9.3-9.7%, 9.7-10.1%, 10.1-10.5%, 10.5-10.9%, 10.9-11.4%, 11.4-11.8%, 11.8-12.2%, or 12.2-12.6%, or about 10.5% by weight or volume. In various embodiments, the composition may comprise, or may consist essentially of, or may consist of dextrose at about 19.0-19.9%, 19.9-20.9%, 20.9-21.8%, 21.8-22.7%, 22.7-23.7%, 23.7-24.6%, 24.6-25.6%, 25.6-26.5%, 26.5-27.5%, or 27.5-28.4%, or about 23.7% by weight or volume. In some embodiments, the composition may consist of or may comprise or may consist essentially of one or more or all of these ingredients. In other embodiments, the composition may consist of or may comprise or may consist essentially of all of these ingredients.

In various embodiments, one serving of a composition described herein may consist of or may comprise or may consist essentially of one or more or all of: citric acid at about 8.4-8.8%, 8.8-9.3%, 9.3-9.7%, 9.7-10.1%, 10.1-10.5%, 10.5-10.9%, 10.9-11.4%, 11.4-11.8%, 11.8-12.2%, or 12.2-12.6%, or about 10.5% by weight or volume; beta alanine at about 13.5-14.1%, 14.1-14.8%, 14.8-15.5%, 15.5-16.2%, 16.2-16.8%, 16.8-17.5%, 17.5-18.2%, 18.2-18.9%, 18.9-19.5%, or 19.5-20.2%, or about 16.8% by weight or volume; quercetin at about 4.43-4.65%, 4.65-4.88%, 4.88-5.10%, 5.10-5.32%, 5.32-5.54%, 5.54-5.76%, 5.76-5.98%, 5.98-6.21%, 6.21-6.43%, or 6.43-6.65%, or about 5.54% by weight or volume; sodium citrate at about 8.4-8.8%, 8.8-9.3%, 9.3-9.7%, 9.7-10.1%, 10.1-10.5%, 10.5-10.9%, 10.9-11.4%, 11.4-11.8%, 11.8-12.2%, or 12.2-12.6%, or about 10.5% by weight or volume; stevia and/or stevia extract at about 1.94-2.03%, 2.03-2.13%, 2.13-2.23%, 2.23-2.32%, 2.32-2.42%, 2.42-2.52%, 2.52-2.61%, 2.61-2.71%, 2.71-2.81%, or 2.81-2.91%, or about 2.42% by weight or volume; fruit flavor (e.g., lemonade, lemon, orange, mandarin orange, pineapple, pearl, apple, grape, cherry, citrus and other fruit flavors) at about 1.68-1.77%, 1.77-1.85%, 1.85-1.94%, 1.94-2.02%, 2.02-2.11%, 2.11-2.19%, 2.19-2.27%, 2.27-2.36%, 2.36-2.44%, or 2.44-2.53%, or about 2.11% by weight or volume; green tea extract and/or natural caffeine at about 1.68-1.77%, 1.77-1.85%, 1.85-1.94%, 1.94-2.02%, 2.02-2.11%, 2.11-2.19%, 2.19-2.27%, 2.27-2.36%, 2.36-2.44%, or 2.44-2.53%, or about 2.11% by weight or volume; potassium citrate at about 8.4-8.8%, 8.8-9.3%, 9.3-9.7%, 9.7-10.1%, 10.1-10.5%, 10.5-10.9%, 10.9-11.4%, 11.4-11.8%, 11.8-12.2%, or 12.2-12.6%, or about 10.5% by weight or volume; and dextrose at about 19.0-19.9%, 19.9-20.9%, 20.9-21.8%, 21.8-22.7%, 22.7-23.7%, 23.7-24.6%, 24.6-25.6%, 25.6-26.5%, 26.5-27.5%, or 27.5-28.4%, or about 23.7% by weight or volume. In some embodiments, the composition may consist of or may comprise or may consist essentially of one or more or all of these ingredients. In other embodiments, the composition may consist of or may comprise or may consist essentially of all of these ingredients.

In various embodiments, the composition may comprise, or may consist essentially of, or may consist of sugar (e.g., glucose, fructose, galactose, maltose, lactose, and sucrose (for example, cane sugar and beet sugar)) at about 1.82-1.91, 1.91-2.00, 2.00-2.09, 2.09-2.18, 2.18-2.28, 2.28-2.37, 2.37-2.46, 2.46-2.55, 2.55-2.64, or 2.64-2.73 g, or about 2.28 g. In various embodiments, the composition may comprise, or may consist essentially of, or may consist of citric acid at about 0.80-0.84, 0.84-0.88, 0.88-0.92, 0.92-0.96, 0.96-1.00, 1.00-1.04, 1.04-1.08, 1.08-1.12, 1.12-1.16, or 1.16-1.20 g, or about 1.00 g. In various embodiments, the composition may comprise, or may consist essentially of, or may consist of beta alanine at about 0.640-0.672, 0.672-0.704, 0.704-0.736, 0.736-0.768, 0.768-0.800, 0.800-0.832, 0.832-0.864, 0.864-0.896, 0.896-0.928, or 0.928-0.960 g, or about 0.800 g. In various embodiments, the composition may comprise, or may consist essentially of, or may consist of quercetin at about 0.402-0.422, 0.422-0.442, 0.442-0.462, 0.462-0.482, 0.482-0.503, 0.503-0.523, 0.523-0.543, 0.543-0.563, 0.563-0.583, or 0.583-0.603 g, or about 0.503 g. In various embodiments, the composition may comprise, or may consist essentially of, or may consist of sodium citrate at about 0.226-0.237, 0.237-0.249, 0.249-0.260, 0.260-0.271, 0.271-0.283, 0.283-0.294, 0.294-0.305, 0.305-0.317, 0.317-0.328, or 0.328-0.339 g, or about 0.283 g. In various embodiments, the composition may comprise, or may consist essentially of, or may consist of stevia and/or stevia extract at about 0.184-0.193, 0.193-0.202, 0.202-0.212, 0.212-0.221, 0.221-0.230, 0.230-0.239, 0.239-0.248, 0.248-0.258, 0.258-0.267, or 0.267-0.276 g, or about 0.230 g. In various embodiments, the composition may comprise, or may consist essentially of, or may consist of fruit flavor (e.g., lemonade, lemon, orange, mandarin orange, pineapple, pearl, apple, grape, cherry, citrus and other fruit flavors) at about 0.160-0.168, 0.168-0.176, 0.176-0.184, 0.184-0.192, 0.192-0.200, 0.200-0.208, 0.208-0.216, 0.216-0.224, 0.224-0.232, or 0.232-0.240 g, or about 0.200 g. In various embodiments, the composition may comprise, or may consist essentially of, or may consist of green tea extract and/or natural caffeine at about 0.160-0.168, 0.168-0.176, 0.176-0.184, 0.184-0.192, 0.192-0.200, 0.200-0.208, 0.208-0.216, 0.216-0.224, 0.224-0.232, or 0.232-0.240 g, or about 0.200 g. In various embodiments, the composition may comprise, or may consist essentially of, or may consist of sodium chloride at about 0.103-0.108, 0.108-0.113, 0.113-0.118, 0.118-0.123, 0.123-

0.128, 0.128-0.133, 0.133-0.138, 0.138-0.144, 0.144-0.149, or 0.149-0.154 g, or about 0.128 g. In various embodiments, the composition may comprise, or may consist essentially of, or may consist of magnesium citrate at about 0.100-0.105, 0.105-0.110, 0.110-0.115, 0.115-0.120, 0.120-0.125, 0.125-0.130, 0.130-0.135, 0.135-0.140, 0.140-0.145, or 0.145-0.150 g, or about 0.125 g. In various embodiments, the composition may comprise, or may consist essentially of, or may consist of silicon dioxide at about 0.096-0.101, 0.101-0.106, 0.106-0.110, 0.110-0.115, 0.115-0.120, 0.120-0.125, 0.125-0.130, 0.130-0.134, 0.134-0.139, or 0.139-0.144 g, or about 0.120 g. In various embodiments, the composition may comprise, or may consist essentially of, or may consist of potassium citrate at about 0.090-0.094, 0.094-0.099, 0.099-0.103, 0.103-0.108, 0.108-0.112, 0.112-0.117, 0.117-0.121, 0.121-0.126, 0.126-0.130, or 0.130-0.135 g, or about 0.112 g. In various embodiments, the composition may comprise, or may consist essentially of, or may consist of calcium citrate at about 0.0190-0.0200, 0.0200-0.0210, 0.0210-0.0219, 0.0219-0.0229, 0.0229-0.0238, 0.0238-0.0248, 0.0248-0.0257, 0.0257-0.0267, 0.0267-0.0276, or 0.0276-0.0286 g, or about 0.02381 g. In some embodiments, the composition may consist of or may comprise or may consist essentially of one or more or all of these ingredients. In other embodiments, the composition may consist of or may comprise or may consist essentially of all of these ingredients.

In various embodiments, one serving of a composition described herein may consist of or may comprise or may consist essentially of one or more or all of: sugar (e.g., glucose, fructose, galactose, maltose, lactose, and sucrose (for example, cane sugar and beet sugar)) at about 1.82-1.91, 1.91-2.00, 2.00-2.09, 2.09-2.18, 2.18-2.28, 2.28-2.37, 2.37-2.46, 2.46-2.55, 2.55-2.64, or 2.64-2.73 g, or about 2.28 g; citric acid at about 0.80-0.84, 0.84-0.88, 0.88-0.92, 0.92-0.96, 0.96-1.00, 1.00-1.04, 1.04-1.08, 1.08-1.12, 1.12-1.16, or 1.16-1.20 g, or about 1.00 g; beta alanine at about 0.640-0.672, 0.672-0.704, 0.704-0.736, 0.736-0.768, 0.768-0.800, 0.800-0.832, 0.832-0.864, 0.864-0.896, 0.896-0.928, or 0.928-0.960 g, or about 0.800 g; quercetin at about 0.402-0.422, 0.422-0.442, 0.442-0.462, 0.462-0.482, 0.482-0.503, 0.503-0.523, 0.523-0.543, 0.543-0.563, 0.563-0.583, or 0.583-0.603 g, or about 0.503 g; sodium citrate at about 0.226-0.237, 0.237-0.249, 0.249-0.260, 0.260-0.271, 0.271-0.283, 0.283-0.294, 0.294-0.305, 0.305-0.317, 0.317-0.328, or 0.328-0.339 g, or about 0.283 g; stevia and/or stevia extract at about 0.184-0.193, 0.193-0.202, 0.202-0.212, 0.212-0.221, 0.221-0.230, 0.230-0.239, 0.239-0.248, 0.248-0.258, 0.258-0.267, or 0.267-0.276 g, or about 0.230 g; fruit flavor (e.g., lemonade, lemon, orange, mandarin orange, pineapple, pearl, apple, grape, cherry, citrus and other fruit flavors) at about 0.160-0.168, 0.168-0.176, 0.176-0.184, 0.184-0.192, 0.192-0.200, 0.200-0.208, 0.208-0.216, 0.216-0.224, 0.224-0.232, or 0.232-0.240 g, or about 0.200 g; green tea extract and/or natural caffeine at about 0.160-0.168, 0.168-0.176, 0.176-0.184, 0.184-0.192, 0.192-0.200, 0.200-0.208, 0.208-0.216, 0.216-0.224, 0.224-0.232, or 0.232-0.240 g, or about 0.200 g; sodium chloride at about 0.103-0.108, 0.108-0.113, 0.113-0.118, 0.118-0.123, 0.123-0.128, 0.128-0.133, 0.133-0.138, 0.138-0.144, 0.144-0.149, or 0.149-0.154 g, or about 0.128 g; magnesium citrate at about 0.100-0.105, 0.105-0.110, 0.110-0.115, 0.115-0.120, 0.120-0.125, 0.125-0.130, 0.130-0.135, 0.135-0.140, 0.140-0.145, or 0.145-0.150 g, or about 0.125 g; silicon dioxide at about 0.096-0.101, 0.101-0.106, 0.106-0.110, 0.110-0.115, 0.115-0.120, 0.120-0.125, 0.125-0.130, 0.130-0.134, 0.134-0.139, or 0.139-0.144 g, or about 0.120 g; potassium citrate at about 0.090-0.094, 0.094-0.099, 0.099-0.103, 0.103-0.108, 0.108-0.112, 0.112-0.117, 0.117-0.121, 0.121-0.126, 0.126-0.130, or 0.130-0.135 g, or about 0.112 g; and calcium citrate at about 0.0190-0.0200, 0.0200-0.0210, 0.0210-0.0219, 0.0219-0.0229, 0.0229-0.0238, 0.0238-0.0248, 0.0248-0.0257, 0.0257-0.0267, 0.0267-0.0276, or 0.0276-0.0286 g, or about 0.02381 g. In some embodiments, the composition may consist of or may comprise or may consist essentially of one or more or all of these ingredients. In other embodiments, the composition may consist of or may comprise or may consist essentially of all of these ingredients.

In various embodiments, the composition may comprise, or may consist essentially of, or may consist of citric acid at about 0.80-0.84, 0.84-0.88, 0.88-0.92, 0.92-0.96, 0.96-1.00, 1.00-1.04, 1.04-1.08, 1.08-1.12, 1.12-1.16, or 1.16-1.20 g, or about 1.00 g. In various embodiments, the composition may comprise, or may consist essentially of, or may consist of beta alanine at about 1.28-1.34, 1.34-1.41, 1.41-1.47, 1.47-1.54, 1.54-1.60, 1.60-1.66, 1.66-1.73, 1.73-1.79, 1.79-1.86, or 1.86-1.92 g, or about 1.60 g. In various embodiments, the composition may comprise, or may consist essentially of, or may consist of quercetin at about 0.421-0.442, 0.442-0.463, 0.463-0.484, 0.484-0.505, 0.505-0.526, 0.526-0.547, 0.547-0.568, 0.568-0.589, 0.589-0.611, or 0.611-0.632 g, or about 0.526 g. In various embodiments, the composition may comprise, or may consist essentially of, or may consist of sodium citrate at about 0.80-0.84, 0.84-0.88, 0.88-0.92, 0.92-0.96, 0.96-1.00, 1.00-1.04, 1.04-1.08, 1.08-1.12, 1.12-1.16, or 1.16-1.20 g, or about 1.00 g. In various embodiments, the composition may comprise, or may consist essentially of, or may consist of stevia and/or stevia extract at about 0.184-0.193, 0.193-0.202, 0.202-0.212, 0.212-0.221, 0.221-0.230, 0.230-0.239, 0.239-0.248, 0.248-0.258, 0.258-0.267, or 0.267-0.276 g, or about 0.230 g. In various embodiments, the composition may comprise, or may consist essentially of, or may consist of fruit flavor (e.g., lemonade, lemon, orange, mandarin orange, pineapple, pearl, apple, grape, cherry, citrus and other fruit flavors) at about 0.160-0.168, 0.168-0.176, 0.176-0.184, 0.184-0.192, 0.192-0.200, 0.200-0.208, 0.208-0.216, 0.216-0.224, 0.224-0.232, or 0.232-0.240 g, or about 0.200 g. In various embodiments, the composition may comprise, or may consist essentially of, or may consist of green tea extract and/or natural caffeine at about 0.160-0.168, 0.168-0.176, 0.176-0.184, 0.184-0.192, 0.192-0.200, 0.200-0.208, 0.208-0.216, 0.216-0.224, 0.224-0.232, or 0.232-0.240 g, or about 0.200 g. In various embodiments, the composition may comprise, or may consist essentially of, or may consist of potassium citrate at about 0.80-0.84, 0.84-0.88, 0.88-0.92, 0.92-0.96, 0.96-1.00, 1.00-1.04, 1.04-1.08, 1.08-1.12, 1.12-1.16, or 1.16-1.20 g, or about 1.00 g. In various embodiments, the composition may comprise, or may consist essentially of, or may consist of dextrose at about 1.80-1.89, 1.89-1.98, 1.98-2.07, 2.07-2.16, 2.16-2.25, 2.25-2.34, 2.34-2.43, 2.43-2.52, 2.52-2.61, or 2.61-2.70 g, or about 2.25 g. In some embodiments, the composition may consist of or may comprise or may consist essentially of one or more or all of these ingredients. In other embodiments, the composition may consist of or may comprise or may consist essentially of all of these ingredients.

In various embodiments, one serving of a composition described herein may consist of or may comprise or may consist essentially of one or more or all of: citric acid at about 0.80-0.84, 0.84-0.88, 0.88-0.92, 0.92-0.96, 0.96-1.00, 1.00-1.04, 1.04-1.08, 1.08-1.12, 1.12-1.16, or 1.16-1.20 g, or about 1.00 g; beta alanine at about 1.28-1.34, 1.34-1.41, 1.41-1.47, 1.47-1.54, 1.54-1.60, 1.60-1.66, 1.66-1.73, 1.73-

1.79, 1.79-1.86, or 1.86-1.92 g, or about 1.60 g; quercetin at about 0.421-0.442, 0.442-0.463, 0.463-0.484, 0.484-0.505, 0.505-0.526, 0.526-0.547, 0.547-0.568, 0.568-0.589, 0.589-0.611, or 0.611-0.632 g, or about 0.526 g; sodium citrate at about 0.80-0.84, 0.84-0.88, 0.88-0.92, 0.92-0.96, 0.96-1.00, 1.00-1.04, 1.04-1.08, 1.08-1.12, 1.12-1.16, or 1.16-1.20 g, or about 1.00 g; stevia and/or stevia extract at about 0.184-0.193, 0.193-0.202, 0.202-0.212, 0.212-0.221, 0.221-0.230, 0.230-0.239, 0.239-0.248, 0.248-0.258, 0.258-0.267, or 0.267-0.276 g, or about 0.230 g; fruit flavor (e.g., lemonade, lemon, orange, mandarin orange, pineapple, pearl, apple, grape, cherry, citrus and other fruit flavors) at about 0.160-0.168, 0.168-0.176, 0.176-0.184, 0.184-0.192, 0.192-0.200, 0.200-0.208, 0.208-0.216, 0.216-0.224, 0.224-0.232, or 0.232-0.240 g, or about 0.200 g; green tea extract and/or natural caffeine at about 0.160-0.168, 0.168-0.176, 0.176-0.184, 0.184-0.192, 0.192-0.200, 0.200-0.208, 0.208-0.216, 0.216-0.224, 0.224-0.232, or 0.232-0.240 g, or about 0.200 g; potassium citrate at about 0.80-0.84, 0.84-0.88, 0.88-0.92, 0.92-0.96, 0.96-1.00, 1.00-1.04, 1.04-1.08, 1.08-1.12, 1.12-1.16, or 1.16-1.20 g, or about 1.00 g; and dextrose at about 1.80-1.89, 1.89-1.98, 1.98-2.07, 2.07-2.16, 2.16-2.25, 2.25-2.34, 2.34-2.43, 2.43-2.52, 2.52-2.61, or 2.61-2.70 g, or about 2.25 g. In some embodiments, the composition may consist of or may comprise or may consist essentially of one or more or all of these ingredients. In other embodiments, the composition may consist of or may comprise or may consist essentially of all of these ingredients.

In various embodiments, one serving of a composition as disclosed herein comprise about 1-2, 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, 20-21, 21-22, 22-23, 23-24, 24-25, 25-26, 26-27, 27-28, 28-29, 29-30, 30-31, 31-32, 32-33, 33-34, 34-35, 35-36, 36-37, 37-38, 38-39, 39-40, 40-41, 41-42, 42-43, 43-44, 44-45, 45-46, 46-47, 47-48, 48-49, 49-50, 50-51, 51-52, 52-53, 53-54, 54-55, 55-56, 56-57, 57-58, 58-59, 59-60, 60-61, 61-62, 62-63, 63-64, 64-65, 65-66, 66-67, 67-68, 68-69, 69-70, 70-71, 71-72, 72-73, 73-74, 74-75, 75-76, 76-77, 77-78, 78-79, 79-80, 80-81, 81-82, 82-83, 83-84, 84-85, 85-86, 86-87, 87-88, 88-89, 89-90, 90-91, 91-92, 92-93, 93-94, 94-95, 95-96, 96-97, 97-98, 98-99, or 99-100 g of the composition. In one embodiment, one serving of a composition as disclosed herein comprises about 6 g of the composition. In another embodiment, one serving of a composition as disclosed herein comprises about 9.5 g of the composition.

In one embodiment, one spoon/level scoop of a composition described herein is one serving of the composition. In another embodiment, two spoons/level scoops of a composition described herein are one serving of the composition. In still another embodiment, three or more spoons/level scoops of a composition described herein are one serving of the composition. In various embodiments, one serving of a composition as disclosed herein is packaged as one packet, tube, vial, pouch, or bag. In various embodiments, two servings of a composition as disclosed herein are packaged as one packet, tube, vial, pouch, or bag. In various embodiments, three or more servings of a composition as disclosed herein are packaged as one packet, tube, vial, pouch, or bag.

In various embodiments, one serving of a composition as disclosed is combined with about 1-2, 2-3, 3-4, 4-5, 5-6, 6-7, 7-8, 8-9, 9-10, 10-11, 11-12, 12-13, 13-14, 14-15, or 15-16 fl. oz. water or any other suitable drinking liquid before being administrated to a subject.

In some embodiments, 1 serving of a composition described herein may be administered to a subject, for example, if the subject's body weight is below about 130, 140, 150, 160, 170, 180, or 190 pounds. In one embodiment, 1 serving of a composition described herein may be administered to a subject having a body weight below 160 pounds. In other embodiments, 2 servings of a composition described herein may be administered to a subject at one time, for example, if the subject's body weight is at or above about 130, 140, 150, 160, 170, 180, or 190 pounds. In one embodiment, 2 servings of a composition described herein may be administered to a subject having a body weight at or above 160 pounds.

In various embodiments, a subject consumes a composition described herein before exercise. In various embodiments, the subject consumes a composition described herein daily. As a non-limiting example, one, two or three servings of a composition described herein (for example, about 6, 12 or 18 g of the composition powder) is mixed with about 8, 16, or 24 fl. oz. water or any other suitable drinking liquid; allowed to sit for about one minute; mixed again if necessary; and consumed by a subject. In one embodiment, the composition is consumed by a subject within a few minutes after preparation.

Various embodiments of the present invention provide a composition. The composition may consist of or may comprise or may consist essentially of one or more or all of: calcium, magnesium, sodium, potassium, beta-alanine, quercetin and caffeine. In various embodiments, the composition may further comprise one or more or all of: sugar (e.g., glucose, fructose, galactose, maltose, lactose, and sucrose (for example, cane sugar and beet sugar)), citric acid, stevia leaf extract, fruit flavor (e.g., lemonade, lemon, orange, mandarin orange, pineapple, pearl, apple, grape, cherry, citrus and other fruit flavors) and silica. In various embodiments, the calcium is in the form of calcium citrate, and/or calcium chloride, and/or any other suitable calcium salts or calcium sources. In various embodiments, the magnesium is in the form of magnesium citrate, and/or magnesium chloride, and/or any other suitable magnesium salts or magnesium sources. In various embodiments, the sodium is in the form of sodium citrate, and/or sodium chloride, and/or any other suitable sodium salts or sodium sources. In various embodiments, the potassium is in the form of potassium citrate, and/or chloride, and/or any other suitable potassium salts or potassium sources. In various embodiments, the quercetin is quercetin anhydrous. In various embodiments, the natural caffeine is in the form of green tea extract and/or natural caffeine. In exemplary embodiments, per serving, the composition may consist of or may comprise or may consist essentially of one or more or all of: about 5 mg calcium, about 20 mg magnesium, about 115 mg sodium, about 40 mg potassium, about 800 mg beta-alanine, about 500 mg quercetin, and about 200 mg green tea extract or about 100 mg natural caffeine. In exemplary embodiments, the composition may be used to improve exercise performance and/or recovery. In some embodiments, the effective amount of the composition to improve exercise performance and/or recovery is about 6 grams in a subject that weighs less than 160 lbs and about 12 grams in a subject that weighs 160 lbs or more. In some embodiments, the effective amount of the composition is dissolved in water. For example, in a subject that weighs less than 160 lbs, about 6 grams of the composition is dissolved in 8 ounces of water; or in a subject that weighs 160 lbs or more, about 12 grams of the composition is dissolved in 16 ounces of water. In some embodiments, the composition is consumed within 30 minutes prior to exercise.

During Exercise

During exercise body temperature rises, and if one is not adequately hydrated, it can result in a drop in power and performance. Water alone during exercise isn't the most effective way to hydrate, and typical sports drinks are filled with sugar and artificial ingredients that can actually dehydrate you and cause gastrointestinal discomfort. For effective hydration during exercise, the body requires an optimal balance of sugar, electrolytes, and water. This balance is known as the fluid's osmolality. Various compositions as described herein combine an optimal osmolality and specific electrolyte levels to maximize fluid absorption and replace electrolytes lost during exercise. When used as directed, these compositions have been specifically formulated to match sweat losses and are completely customizable to training duration. One should keep being hydrated to improve exercise effectiveness, recovery, and general well-being.

In various embodiments, the present invention provides a composition for improving exercise performance and/or recovery. Ingredients of the composition may include but are not limited to sugar (e.g., glucose, fructose, galactose, maltose, lactose, and sucrose (for example, cane sugar and beet sugar)), dextrose, sodium citrate, citric acid, quercetin, magnesium citrate, silicon dioxide, potassium citrate, calcium citrate, fruit flavor (e.g., lemonade, lemon, orange, mandarin orange, pineapple, pearl, apple, grape, cherry, citrus and other fruit flavors), and stevia and/or stevia leaf extract. In various embodiments, the fruit flavor is natural orange or mandarin orange flavor.

In various embodiments, the present invention provides a composition for improving exercise performance and/or recovery. The composition may consist of or may comprise or may consist essentially of one or more or all of: sugar (e.g., glucose, fructose, galactose, maltose, lactose, and sucrose (for example, cane sugar and beet sugar)), dextrose, sodium citrate, citric acid, quercetin, magnesium citrate, silicon dioxide, potassium citrate, calcium citrate, fruit flavor (e.g., lemonade, lemon, orange, mandarin orange, pineapple, pearl, apple, grape, cherry, citrus and other fruit flavors), and stevia and/or stevia leaf extract. In various embodiments, the fruit flavor is natural orange or mandarin orange flavor.

In various embodiments, the present invention provides a composition for improving exercise performance and/or recovery. The composition may consist of or may comprise or may consist essentially of one or more or all of: sugar (e.g., glucose, fructose, galactose, maltose, lactose, and sucrose (for example, cane sugar and beet sugar)), dextrose, sodium citrate, citric acid, quercetin, magnesium citrate, potassium citrate, calcium citrate, fruit flavor (e.g., lemonade, lemon, orange, mandarin orange, pineapple, pearl, apple, grape, cherry, citrus and other fruit flavors), and stevia and/or stevia leaf extract. In various embodiments, the fruit flavor is natural orange or mandarin orange flavor.

In various embodiments, the sugar (e.g., glucose, fructose, galactose, maltose, lactose, and sucrose (for example, cane sugar and beet sugar)) is granulated sugar. In various embodiments, the citric acid is citric acid granular. In various embodiments, the quercetin is quercetin anhydrous, quercetin 95%, quercetin 99.5%, or quercetin dehydrate. In various embodiments, the magnesium citrate is magnesium citrate 16% Mg. In various embodiments, the potassium citrate is potassium citrate 36% K. In various embodiments, the calcium citrate is calcium citrate tetrahydrate. In various embodiments, the fruit flavor is natural orange or mandarin orange flavor.

In various embodiments, the present invention provides a composition for improving exercise performance and/or recovery. The composition may consist of or may comprise or may consist essentially of one or more or all of: granulated sugar (e.g., glucose, fructose, galactose, maltose, lactose, and sucrose (for example, cane sugar and beet sugar)), dextrose, sodium citrate, citric acid granular, quercetin anhydrous, magnesium citrate, silicon dioxide, potassium citrate, calcium citrate tetrahydrate, natural fruit flavor (e.g., lemonade, lemon, orange, mandarin orange, pineapple, pearl, apple, grape, cherry, citrus and other fruit flavors), and stevia. In various embodiments, the fruit flavor is natural orange or mandarin orange flavor.

In various embodiments, the present invention provides a composition for improving exercise performance and/or recovery. The composition may consist of or may comprise or may consist essentially of one or more or all of: sugar (e.g., glucose, fructose, galactose, maltose, lactose, and sucrose (for example, cane sugar and beet sugar)), dextrose, sodium citrate, citric acid, quercetin 95%, magnesium citrate, potassium citrate, calcium citrate, fruit flavor (e.g., lemonade, lemon, orange, mandarin orange, pineapple, pearl, apple, grape, cherry, citrus and other fruit flavors), and stevia. In various embodiments, the fruit flavor is natural orange or mandarin orange flavor.

In various embodiments, the composition may comprise, or may consist essentially of, or may consist of sugar (e.g., glucose, fructose, galactose, maltose, lactose, and sucrose (for example, cane sugar and beet sugar)) at about 41.5-43.6%, 43.6-45.7%, 45.7-47.7%, 47.7-49.8%, 49.8-51.9%, 51.9-54.0%, 54.0-56.0%, 56.0-58.1%, 58.1-60.2%, or 60.2-62.3%, or about 51.9% by weight or volume. In various embodiments, the composition may comprise, or may consist essentially of, or may consist of dextrose at about 20.9-21.9%, 21.9-23.0%, 23.0-24.0%, 24.0-25.0%, 25.0-26.1%, 26.1-27.1%, 27.1-28.2%, 28.2-29.2%, 29.2-30.3%, or 30.3-31.3%, or about 26.1% by weight or volume. In various embodiments, the composition may comprise, or may consist essentially of, or may consist of sodium citrate at about 6.96-7.30%, 7.30-7.65%, 7.65-8.00%, 8.00-8.35%, 8.35-8.70%, 8.70-9.04%, 9.04-9.39%, 9.39-9.74%, 9.74-10.09%, or 10.09-10.43%, or about 8.70% by weight or volume. In various embodiments, the composition may comprise, or may consist essentially of, or may consist of citric acid at about 3.48-3.65%, 3.65-3.83%, 3.83-4.00%, 4.00-4.17%, 4.17-4.35%, 4.35-4.52%, 4.52-4.70%, 4.70-4.87%, 4.87-5.04%, or 5.04-5.22%, or about 4.35% by weight or volume. In various embodiments, the composition may comprise, or may consist essentially of, or may consist of quercetin at about 1.75-1.84%, 1.84-1.92%, 1.92-2.01%, 2.01-2.10%, 2.10-2.18%, 2.18-2.27%, 2.27-2.36%, 2.36-2.45%, 2.45-2.53%, or 2.53-2.62%, or about 2.18% by weight or volume. In various embodiments, the composition may comprise, or may consist essentially of, or may consist of magnesium citrate at about 1.74-1.83%, 1.83-1.91%, 1.91-2.00%, 2.00-2.09%, 2.09-2.17%, 2.17-2.26%, 2.26-2.35%, 2.35-2.43%, 2.43-2.52%, or 2.52-2.61%, or about 2.17% by weight or volume. In various embodiments, the composition may comprise, or may consist essentially of, or may consist of silicon dioxide at about 1.60-1.68%, 1.68-1.76%, 1.76-1.84%, 1.84-1.92%, 1.92-2.00%, 2.00-2.08%, 2.08-2.16%, 2.16-2.24%, 2.24-2.32%, or 2.32-2.40%, or about 2.00% by weight or volume. In various embodiments, the composition may comprise, or may consist essentially of, or may consist of potassium citrate at about 1.56-1.64%, 1.64-1.72%, 1.72-1.80%, 1.80-1.88%, 1.88-1.95%, 1.95-2.03%, 2.03-2.11%, 2.11-2.19%, 2.19-2.27%, or 2.27-

2.34%, or about 1.95% by weight or volume. In various embodiments, the composition may comprise, or may consist essentially of, or may consist of calcium citrate at about 0.331-0.348%, 0.348-0.364%, 0.364-0.381%, 0.381-0.398%, 0.398-0.414%, 0.414-0.431%, 0.431-0.447%, 0.447-0.464%, 0.464-0.480%, or 0.480-0.497%, or about 0.414% by weight or volume. In various embodiments, the composition may comprise, or may consist essentially of, or may consist of fruit flavor (e.g., lemonade, lemon, orange, mandarin orange, pineapple, pearl, apple, grape, cherry, citrus and other fruit flavors) at about 0.139-0.146%, 0.146-0.153%, 0.153-0.160%, 0.160-0.167%, 0.167-0.174%, 0.174-0.181%, 0.181-0.188%, 0.188-0.195%, 0.195-0.202%, or 0.202-0.209%, or about 0.174% by weight or volume. In various embodiments, the composition may comprise, or may consist essentially of, or may consist of stevia and/or stevia leaf extract at about 0.0696-0.0730%, 0.0730-0.0765%, 0.0765-0.0800%, 0.0800-0.0835%, 0.0835-0.0870%, 0.0870-0.0904%, 0.0904-0.0939%, 0.0939-0.0974%, 0.0974-0.1009%, or 0.1009-0.1043%, or about 0.0870% by weight or volume. In some embodiments, the composition may consist of or may comprise or may consist essentially of one or more or all of these ingredients. In other embodiments, the composition may consist of or may comprise or may consist essentially of all of these ingredients.

In various embodiments, one serving of a composition described herein may consist of or may comprise or may consist essentially of one or more or all of: sugar (e.g., glucose, fructose, galactose, maltose, lactose, and sucrose (for example, cane sugar and beet sugar)) at about 41.5-43.6%, 43.6-45.7%, 45.7-47.7%, 47.7-49.8%, 49.8-51.9%, 51.9-54.0%, 54.0-56.0%, 56.0-58.1%, 58.1-60.2%, or 60.2-62.3%, or about 51.9% by weight or volume; dextrose at about 20.9-21.9%, 21.9-23.0%, 23.0-24.0%, 24.0-25.0%, 25.0-26.1%, 26.1-27.1%, 27.1-28.2%, 28.2-29.2%, 29.2-30.3%, or 30.3-31.3%, or about 26.1% by weight or volume; sodium citrate at about 6.96-7.30%, 7.30-7.65%, 7.65-8.00%, 8.00-8.35%, 8.35-8.70%, 8.70-9.04%, 9.04-9.39%, 9.39-9.74%, 9.74-10.09%, or 10.09-10.43%, or about 8.70% by weight or volume; citric acid at about 3.48-3.65%, 3.65-3.83%, 3.83-4.00%, 4.00-4.17%, 4.17-4.35%, 4.35-4.52%, 4.52-4.70%, 4.70-4.87%, 4.87-5.04%, or 5.04-5.22%, or about 4.35% by weight or volume; quercetin at about 1.75-1.84%, 1.84-1.92%, 1.92-2.01%, 2.01-2.10%, 2.10-2.18%, 2.18-2.27%, 2.27-2.36%, 2.36-2.45%, 2.45-2.53%, or 2.53-2.62%, or about 2.18% by weight or volume; magnesium citrate at about 1.74-1.83%, 1.83-1.91%, 1.91-2.00%, 2.00-2.09%, 2.09-2.17%, 2.17-2.26%, 2.26-2.35%, 2.35-2.43%, 2.43-2.52%, or 2.52-2.61%, or about 2.17% by weight or volume; silicon dioxide at about 1.60-1.68%, 1.68-1.76%, 1.76-1.84%, 1.84-1.92%, 1.92-2.00%, 2.00-2.08%, 2.08-2.16%, 2.16-2.24%, 2.24-2.32%, or 2.32-2.40%, or about 2.00% by weight or volume; potassium citrate at about 1.56-1.64%, 1.64-1.72%, 1.72-1.80%, 1.80-1.88%, 1.88-1.95%, 1.95-2.03%, 2.03-2.11%, 2.11-2.19%, 2.19-2.27%, or 2.27-2.34%, or about 1.95% by weight or volume; calcium citrate at about 0.331-0.348%, 0.348-0.364%, 0.364-0.381%, 0.381-0.398%, 0.398-0.414%, 0.414-0.431%, 0.431-0.447%, 0.447-0.464%, 0.464-0.480%, or 0.480-0.497%, or about 0.414% by weight or volume; fruit flavor (e.g., lemonade, lemon, orange, mandarin orange, pineapple, pearl, apple, grape, cherry, citrus and other fruit flavors) at about 0.139-0.146%, 0.146-0.153%, 0.153-0.160%, 0.160-0.167%, 0.167-0.174%, 0.174-0.181%, 0.181-0.188%, 0.188-0.195%, 0.195-0.202%, or 0.202-0.209%, or about 0.174% by weight or volume; and stevia and/or stevia leaf extract at about 0.0696-0.0730%, 0.0730-0.0765%, 0.0765-0.0800%, 0.0800-0.0835%, 0.0835-0.0870%, 0.0870-0.0904%, 0.0904-0.0939%, 0.0939-0.0974%, 0.0974-0.1009%, or 0.1009-0.1043%, or about 0.0870% by weight or volume. In some embodiments, the composition may consist of or may comprise or may consist essentially of one or more or all of these ingredients. In other embodiments, the composition may consist of or may comprise or may consist essentially of all of these ingredients.

In various embodiments, the composition may comprise, or may consist essentially of, or may consist of sugar (e.g., glucose, fructose, galactose, maltose, lactose, and sucrose (for example, cane sugar and beet sugar)) at about 31.4-32.9%, 32.9-34.5%, 34.5-36.1%, 36.1-37.6%, 37.6-39.2%, 39.2-40.8%, 40.8-42.3%, 42.3-43.9%, 43.9-45.5%, or 45.5-47.0%, or about 39.2% by weight or volume. In various embodiments, the composition may comprise, or may consist essentially of, or may consist of dextrose at about 33.5-35.1%, 35.1-36.8%, 36.8-38.5%, 38.5-40.1%, 40.1-41.8%, 41.8-43.5%, 43.5-45.2%, 45.2-46.8%, 46.8-48.5%, or 48.5-50.2%, or about 41.8% by weight or volume. In various embodiments, the composition may comprise, or may consist essentially of, or may consist of sodium citrate at about 6.97-7.32%, 7.32-7.67%, 7.67-8.02%, 8.02-8.36%, 8.36-8.71%, 8.71-9.06%, 9.06-9.41%, 9.41-9.76%, 9.76-10.11%, or 10.11-10.46%, or about 8.71% by weight or volume. In various embodiments, the composition may comprise, or may consist essentially of, or may consist of citric acid at about 3.49-3.66%, 3.66-3.83%, 3.83-4.01%, 4.01-4.18%, 4.18-4.36%, 4.36-4.53%, 4.53-4.70%, 4.70-4.88%, 4.88-5.05%, or 5.05-5.23%, or about 4.36% by weight or volume. In various embodiments, the composition may comprise, or may consist essentially of, or may consist of quercetin at about 1.74-1.83%, 1.83-1.92%, 1.92-2.00%, 2.00-2.09%, 2.09-2.18%, 2.18-2.27%, 2.27-2.35%, 2.35-2.44%, 2.44-2.53%, or 2.53-2.61%, or about 2.18% by weight or volume. In various embodiments, the composition may comprise, or may consist essentially of, or may consist of magnesium citrate at about 0.87-0.91%, 0.91-0.96%, 0.96-1.00%, 1.00-1.05%, 1.05-1.09%, 1.09-1.13%, 1.13-1.18%, 1.18-1.22%, 1.22-1.26%, or 1.26-1.31%, or about 1.09% by weight or volume. In various embodiments, the composition may comprise, or may consist essentially of, or may consist of potassium citrate at about 1.57-1.64%, 1.64-1.72%, 1.72-1.80%, 1.80-1.88%, 1.88-1.96%, 1.96-2.04%, 2.04-2.11%, 2.11-2.19%, 2.19-2.27%, or 2.27-2.35%, or about 1.96% by weight or volume. In various embodiments, the composition may comprise, or may consist essentially of, or may consist of calcium citrate at about 0.332-0.349%, 0.349-0.365%, 0.365-0.382%, 0.382-0.398%, 0.398-0.415%, 0.415-0.431%, 0.431-0.448%, 0.448-0.465%, 0.465-0.481%, or 0.481-0.498%, or about 0.415% by weight or volume. In various embodiments, the composition may comprise, or may consist essentially of, or may consist of fruit flavor (e.g., lemonade, lemon, orange, mandarin orange, pineapple, pearl, apple, grape, cherry, citrus and other fruit flavors) at about 0.139-0.146%, 0.146-0.153%, 0.153-0.160%, 0.160-0.167%, 0.167-0.174%, 0.174-0.181%, 0.181-0.188%, 0.188-0.195%, 0.195-0.202%, or 0.202-0.209%, or about 0.174% by weight or volume. In various embodiments, the composition may comprise, or may consist essentially of, or may consist of stevia and/or stevia leaf extract at about 0.0697-0.0732%, 0.0732-0.0767%, 0.0767-0.0802%, 0.0802-0.0836%, 0.0836-0.0871%, 0.0871-0.0906%, 0.0906-0.0941%, 0.0941-0.0976%, 0.0976-0.1011%, or 0.1011-0.1046%, or about 0.0871% by weight or volume. In some embodiments, the composition may consist of or may comprise or may consist essentially of one or more or all of these ingredients. In other embodiments, the composition may consist of or may comprise or may consist essentially of all of these ingredients.

In various embodiments, one serving of a composition described herein may consist of or may comprise or may consist essentially of one or more or all of: sugar (e.g., glucose, fructose, galactose, maltose, lactose, and sucrose (for example, cane sugar and beet sugar)) at about 31.4-32.9%, 32.9-34.5%, 34.5-36.1%, 36.1-37.6%, 37.6-39.2%, 39.2-40.8%, 40.8-42.3%, 42.3-43.9%, 43.9-45.5%, or 45.5-47.0%, or about 39.2% by weight or volume; dextrose at about 33.5-35.1%, 35.1-36.8%, 36.8-38.5%, 38.5-40.1%, 40.1-41.8%, 41.8-43.5%, 43.5-45.2%, 45.2-46.8%, 46.8-48.5%, or 48.5-50.2%, or about 41.8% by weight or volume; sodium citrate at about 6.97-7.32%, 7.32-7.67%, 7.67-8.02%, 8.02-8.36%, 8.36-8.71%, 8.71-9.06%, 9.06-9.41%, 9.41-9.76%, 9.76-10.11%, or 10.11-10.46%, or about 8.71% by weight or volume; citric acid at about 3.49-3.66%, 3.66-3.83%, 3.83-4.01%, 4.01-4.18%, 4.18-4.36%, 4.36-4.53%, 4.53-4.70%, 4.70-4.88%, 4.88-5.05%, or 5.05-5.23%, or about 4.36% by weight or volume; quercetin at about 1.74-1.83%, 1.83-1.92%, 1.92-2.00%, 2.00-2.09%, 2.09-2.18%, 2.18-2.27%, 2.27-2.35%, 2.35-2.44%, 2.44-2.53%, or 2.53-2.61%, or about 2.18% by weight or volume; magnesium citrate at about 0.87-0.91%, 0.91-0.96%, 0.96-1.00%, 1.00-1.05%, 1.05-1.09%, 1.09-1.13%, 1.13-1.18%, 1.18-1.22%, 1.22-1.26%, or 1.26-1.31%, or about 1.09% by weight or volume; potassium citrate at about 1.57-1.64%, 1.64-1.72%, 1.72-1.80%, 1.80-1.88%, 1.88-1.96%, 1.96-2.04%, 2.04-2.11%, 2.11-2.19%, 2.19-2.27%, or 2.27-2.35%, or about 1.96% by weight or volume; calcium citrate at about 0.332-0.349%, 0.349-0.365%, 0.365-0.382%, 0.382-0.398%, 0.398-0.415%, 0.415-0.431%, 0.431-0.448%, 0.448-0.465%, 0.465-0.481%, or 0.481-0.498%, or about 0.415% by weight or volume; fruit flavor (e.g., lemonade, lemon, orange, mandarin orange, pineapple, pearl, apple, grape, cherry, citrus and other fruit flavors) at about 0.139-0.146%, 0.146-0.153%, 0.153-0.160%, 0.160-0.167%, 0.167-0.174%, 0.174-0.181%, 0.181-0.188%, 0.188-0.195%, 0.195-0.202%, or 0.202-0.209%, or about 0.174% by weight or volume; and stevia and/or stevia leaf extract at about 0.0697-0.0732%, 0.0732-0.0767%, 0.0767-0.0802%, 0.0802-0.0836%, 0.0836-0.0871%, 0.0871-0.0906%, 0.0906-0.0941%, 0.0941-0.0976%, 0.0976-0.1011%, or 0.1011-0.1046%, or about 0.0871% by weight or volume. In some embodiments, the composition may consist of or may comprise or may consist essentially of one or more or all of these ingredients. In other embodiments, the composition may consist of or may comprise or may consist essentially of all of these ingredients.

In various embodiments, the composition may comprise, or may consist essentially of, or may consist of sugar (e.g., glucose, fructose, galactose, maltose, lactose, and sucrose (for example, cane sugar and beet sugar)) at about 4.77-5.01, 5.01-5.25, 5.25-5.49, 5.49-5.73, 5.73-5.97, 5.97-6.21, 6.21-6.44, 6.44-6.68, 6.68-6.92, or 6.92-7.16 g, or about 5.97 g. In various embodiments, the composition may comprise, or may consist essentially of, or may consist of dextrose at about 2.40-2.52, 2.52-2.64, 2.64-2.76, 2.76-2.88, 2.88-3.00, 3.00-3.12, 3.12-3.24, 3.24-3.36, 3.36-3.48, or 3.48-3.60 g, or about 3.00 g. In various embodiments, the composition may comprise, or may consist essentially of, or may consist of sodium citrate at about 0.80-0.84, 0.84-0.88, 0.88-0.92, 0.92-0.96, 0.96-1.00, 1.00-1.04, 1.04-1.08, 1.08-1.12, 1.12-1.16, or 1.16-1.20 g, or about 1.00 g. In various embodiments, the composition may comprise, or may consist essentially of, or may consist of citric acid at about 0.400-0.420, 0.420-0.440, 0.440-0.460, 0.460-0.480, 0.480-0.500, 0.500-0.520, 0.520-0.540, 0.540-0.560, 0.560-0.580, or 0.580-0.600 g, or about 0.500 g. In various embodiments, the composition may comprise, or may consist essentially of, or may consist of quercetin at about 0.201-0.211, 0.211-0.221, 0.221-0.231, 0.231-0.241, 0.241-0.251, 0.251-0.261, 0.261-0.271, 0.271-0.281, 0.281-0.291, or 0.291-0.302 g, or about 0.251 g. In various embodiments, the composition may comprise, or may consist essentially of, or may consist of magnesium citrate at about 0.200-0.210, 0.210-0.220, 0.220-0.230, 0.230-0.240, 0.240-0.250, 0.250-0.260, 0.260-0.270, 0.270-0.280, 0.280-0.290, or 0.290-0.300 g, or about 0.250 g. In various embodiments, the composition may comprise, or may consist essentially of, or may consist of silicon dioxide at about 0.184-0.193, 0.193-0.202, 0.202-0.212, 0.212-0.221, 0.221-0.230, 0.230-0.239, 0.239-0.248, 0.248-0.258, 0.258-0.267, or 0.267-0.276 g, or about 0.230 g. In various embodiments, the composition may comprise, or may consist essentially of, or may consist of potassium citrate at about 0.180-0.189, 0.189-0.198, 0.198-0.207, 0.207-0.216, 0.216-0.225, 0.225-0.234, 0.234-0.243, 0.243-0.252, 0.252-0.261, or 0.261-0.270 g, or about 0.225 g. In various embodiments, the composition may comprise, or may consist essentially of, or may consist of calcium citrate at about 0.0381-0.0400, 0.0400-0.0419, 0.0419-0.0438, 0.0438-0.0457, 0.0457-0.0476, 0.0476-0.0495, 0.0495-0.0514, 0.0514-0.0533, 0.0533-0.0552, or 0.0552-0.0571 g, or about 0.0476 g. In various embodiments, the composition may comprise, or may consist essentially of, or may consist of fruit flavor (e.g., lemonade, lemon, orange, mandarin orange, pineapple, pearl, apple, grape, cherry, citrus and other fruit flavors) at about 0.0160-0.0168, 0.0168-0.0176, 0.0176-0.0184, 0.0184-0.0192, 0.0192-0.0200, 0.0200-0.0208, 0.0208-0.0216, 0.0216-0.0224, 0.0224-0.0232, or 0.0232-0.0240 g, or about 0.0200 g. In various embodiments, the composition may comprise, or may consist essentially of, or may consist of stevia and/or stevia leaf extract at about 0.0080-0.0084, 0.0084-0.0088, 0.0088-0.0092, 0.0092-0.0096, 0.0096-0.0100, 0.0100-0.0104, 0.0104-0.0108, 0.0108-0.0112, 0.0112-0.0116, or 0.0116-0.0120 g, or about 0.0100 g. In some embodiments, the composition may consist of or may comprise or may consist essentially of one or more or all of these ingredients. In other embodiments, the composition may consist of or may comprise or may consist essentially of all of these ingredients.

In various embodiments, one serving of a composition described herein may consist of or may comprise or may consist essentially of one or more or all of: sugar (e.g., glucose, fructose, galactose, maltose, lactose, and sucrose (for example, cane sugar and beet sugar)) at about 4.77-5.01, 5.01-5.25, 5.25-5.49, 5.49-5.73, 5.73-5.97, 5.97-6.21, 6.21-6.44, 6.44-6.68, 6.68-6.92, or 6.92-7.16 g, or about 5.97 g; dextrose at about 2.40-2.52, 2.52-2.64, 2.64-2.76, 2.76-2.88, 2.88-3.00, 3.00-3.12, 3.12-3.24, 3.24-3.36, 3.36-3.48, or 3.48-3.60 g, or about 3.00 g; sodium citrate at about 0.80-0.84, 0.84-0.88, 0.88-0.92, 0.92-0.96, 0.96-1.00, 1.00-1.04, 1.04-1.08, 1.08-1.12, 1.12-1.16, or 1.16-1.20 g, or about 1.00 g; citric acid at about 0.400-0.420, 0.420-0.440, 0.440-0.460, 0.460-0.480, 0.480-0.500, 0.500-0.520, 0.520-0.540, 0.540-0.560, 0.560-0.580, or 0.580-0.600 g, or about 0.500 g; quercetin at about 0.201-0.211, 0.211-0.221, 0.221-0.231, 0.231-0.241, 0.241-0.251, 0.251-0.261, 0.261-0.271, 0.271-0.281, 0.281-0.291, or 0.291-0.302 g, or about 0.251 g; magnesium citrate at about 0.200-0.210, 0.210-0.220, 0.220-0.230, 0.230-0.240, 0.240-0.250, 0.250-0.260, 0.260-0.270, 0.270-0.280, 0.280-0.290, or 0.290-0.300 g, or about 0.250 g; silicon dioxide at about 0.184-0.193, 0.193-0.202, 0.202-0.212, 0.212-0.221, 0.221-0.230, 0.230-0.239, 0.239-0.248, 0.248-0.258, 0.258-0.267, or 0.267-0.276 g, or about 0.230 g; potassium citrate at about 0.180-0.189, 0.189-0.198, 0.198-0.207, 0.207-0.216, 0.216-0.225, 0.225-0.234, 0.234-0.243, 0.243-0.252, 0.252-0.261, or 0.261-0.270 g, or about 0.225 g; calcium citrate at about 0.0381-0.0400, 0.0400-0.0419, 0.0419-0.0438, 0.0438-0.0457, 0.0457-0.0476, 0.0476-0.0495, 0.0495-0.0514, 0.0514-0.0533, 0.0533-0.0552, or 0.0552-0.0571 g, or about 0.0476 g; fruit flavor (e.g., lemonade, lemon, orange, mandarin orange, pineapple, pearl, apple, grape, cherry, citrus and other fruit flavors) at about 0.0160-0.0168, 0.0168-0.0176, 0.0176-0.0184, 0.0184-0.0192, 0.0192-0.0200, 0.0200-0.0208, 0.0208-0.0216, 0.0216-0.0224, 0.0224-0.0232, or 0.0232-0.0240 g, or about 0.0200 g; and stevia and/or stevia leaf extract at about 0.0080-0.0084, 0.0084-0.0088, 0.0088-0.0092, 0.0092-0.0096, 0.0096-0.0100, 0.0100-0.0104, 0.0104-0.0108, 0.0108-0.0112, 0.0112-0.0116, or 0.0116-0.0120 g, or about 0.0100 g. In some embodiments, one serving of the composition may consist of or may comprise or may consist essentially of one or more or all of these ingredients. In other embodiments, one serving of the composition may consist of or may comprise or may consist essentially of all of these ingredients.

In various embodiments, the composition may comprise, or may consist essentially of, or may consist of sugar (e.g., glucose, fructose, galactose, maltose, lactose, and sucrose (for example, cane sugar and beet sugar)) at about 3.60-3.78, 3.78-3.96, 3.96-4.14, 4.14-4.32, 4.32-4.50, 4.50-4.68, 4.68-4.86, 4.86-5.04, 5.04-5.22, or 5.22-5.40 g, or about 4.50 g. In various embodiments, the composition may comprise, or may consist essentially of, or may consist of dextrose at about 3.84-4.03, 4.03-4.22, 4.22-4.42, 4.42-4.61, 4.61-4.80, 4.80-4.99, 4.99-5.18, 5.18-5.38, 5.38-5.57, or 5.57-5.76 g, or about 4.80 g. In various embodiments, the composition may comprise, or may consist essentially of, or may consist of sodium citrate at about 0.80-0.84, 0.84-0.88, 0.88-0.92, 0.92-0.96, 0.96-1.00, 1.00-1.04, 1.04-1.08, 1.08-1.12, 1.12-1.16, or 1.16-1.20 g, or about 1.00 g. In various embodiments, the composition may comprise, or may consist essentially of, or may consist of citric acid at about 0.400-0.420, 0.420-0.440, 0.440-0.460, 0.460-0.480, 0.480-0.500, 0.500-0.520, 0.520-0.540, 0.540-0.560, 0.560-0.580, or 0.580-0.600 g, or about 0.500 g. In various embodiments, the composition may comprise, or may consist essentially of, or may consist of quercetin at about 0.200-0.210, 0.210-0.220, 0.220-0.230, 0.230-0.240, 0.240-0.250, 0.250-0.260, 0.260-0.270, 0.270-0.280, 0.280-0.290, or 0.290-0.300 g, or about 0.250 g. In various embodiments, the composition may comprise, or may consist essentially of, or may consist of magnesium citrate at about 0.100-0.105, 0.105-0.110, 0.110-0.115, 0.115-0.120, 0.120-0.125, 0.125-0.130, 0.130-0.135, 0.135-0.140, 0.140-0.145, or 0.145-0.150 g, or about 0.125 g. In various embodiments, the composition may comprise, or may consist essentially of, or may consist of potassium citrate at about 0.180-0.189, 0.189-0.198, 0.198-0.207, 0.207-0.216, 0.216-0.225, 0.225-0.234, 0.234-0.243, 0.243-0.252, 0.252-0.261, or 0.261-0.270 g, or about 0.225 g. In various embodiments, the composition may comprise, or may consist essentially of, or may consist of calcium citrate at about 0.0381-0.0400, 0.0400-0.0419, 0.0419-0.0438, 0.0438-0.0457, 0.0457-0.0476, 0.0476-0.0495, 0.0495-0.0514, 0.0514-0.0533, 0.0533-0.0552, or 0.0552-0.0571 g, or about 0.0476 g. In various embodiments, the composition may comprise, or may consist essentially of, or may consist of fruit flavor (e.g., lemonade, lemon, orange, mandarin orange, pineapple, pearl, apple, grape, cherry, citrus and other fruit flavors) at about 0.0160-0.0168, 0.0168-0.0176, 0.0176-0.0184, 0.0184-0.0192, 0.0192-0.0200, 0.0200-0.0208, 0.0208-0.0216, 0.0216-0.0224, 0.0224-0.0232, or 0.0232-0.0240 g, or about 0.0200 g. In various embodiments, the composition may comprise, or may consist essentially of, or may consist of stevia and/or stevia leaf extract at about 0.0080-0.0084, 0.0084-0.0088, 0.0088-0.0092, 0.0092-0.0096, 0.0096-0.0100, 0.0100-0.0104, 0.0104-0.0108, 0.0108-0.0112, 0.0112-0.0116, or 0.0116-0.0120 g, or about 0.0100 g. In some embodiments, the composition may consist of or may comprise or may consist essentially of one or more or all of these ingredients. In other embodiments, the composition may consist of or may comprise or may consist essentially of all of these ingredients.

In various embodiments, one serving of a composition described herein may consist of or may comprise or may consist essentially of one or more or all of: sugar (e.g., glucose, fructose, galactose, maltose, lactose, and sucrose (for example, cane sugar and beet sugar)) at about 3.60-3.78, 3.78-3.96, 3.96-4.14, 4.14-4.32, 4.32-4.50, 4.50-4.68, 4.68-4.86, 4.86-5.04, 5.04-5.22, or 5.22-5.40 g, or about 4.50 g; dextrose at about 3.84-4.03, 4.03-4.22, 4.22-4.42, 4.42-4.61, 4.61-4.80, 4.80-4.99, 4.99-5.18, 5.18-5.38, 5.38-5.57, or 5.57-5.76 g, or about 4.80 g; sodium citrate at about 0.80-0.84, 0.84-0.88, 0.88-0.92, 0.92-0.96, 0.96-1.00, 1.00-1.04, 1.04-1.08, 1.08-1.12, 1.12-1.16, or 1.16-1.20 g, or about 1.00 g; citric acid at about 0.400-0.420, 0.420-0.440, 0.440-0.460, 0.460-0.480, 0.480-0.500, 0.500-0.520, 0.520-0.540, 0.540-0.560, 0.560-0.580, or 0.580-0.600 g, or about 0.500 g; quercetin at about 0.200-0.210, 0.210-0.220, 0.220-0.230, 0.230-0.240, 0.240-0.250, 0.250-0.260, 0.260-0.270, 0.270-0.280, 0.280-0.290, or 0.290-0.300 g, or about 0.250 g; magnesium citrate at about 0.100-0.105, 0.105-0.110, 0.110-0.115, 0.115-0.120, 0.120-0.125, 0.125-0.130, 0.130-0.135, 0.135-0.140, 0.140-0.145, or 0.145-0.150 g, or about 0.125 g; potassium citrate at about 0.180-0.189, 0.189-0.198, 0.198-0.207, 0.207-0.216, 0.216-0.225, 0.225-0.234, 0.234-0.243, 0.243-0.252, 0.252-0.261, or 0.261-0.270 g, or about 0.225 g; calcium citrate at about 0.0381-0.0400, 0.0400-0.0419, 0.0419-0.0438, 0.0438-0.0457, 0.0457-0.0476, 0.0476-0.0495, 0.0495-0.0514, 0.0514-0.0533, 0.0533-0.0552, or 0.0552-0.0571 g, or about 0.0476 g; fruit flavor (e.g., lemonade, lemon, orange, mandarin orange, pineapple, pearl, apple, grape, cherry, citrus and other fruit flavors) at about 0.0160-0.0168, 0.0168-0.0176, 0.0176-0.0184, 0.0184-0.0192, 0.0192-0.0200, 0.0200-0.0208, 0.0208-0.0216, 0.0216-0.0224, 0.0224-0.0232, or 0.0232-0.0240 g, or about 0.0200 g; and stevia and/or stevia leaf extract at about 0.0080-0.0084, 0.0084-0.0088, 0.0088-0.0092, 0.0092-0.0096, 0.0096-0.0100, 0.0100-0.0104, 0.0104-0.0108, 0.0108-0.0112, 0.0112-0.0116, or 0.0116-0.0120 g, or about 0.0100 g. In some embodiments, one serving of the composition may consist of or may comprise or may consist essentially of one or more or all of these ingredients. In other embodiments, one serving of the composition may consist of or may comprise or may consist essentially of all of these ingredients.

In various embodiments, one serving of a composition as disclosed herein comprise about 1-2, 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, 20-21, 21-22, 22-23, 23-24, 24-25, 25-26, 26-27, 27-28, 28-29, 29-30, 30-31, 31-32, 32-33, 33-34, 34-35, 35-36, 36-37, 37-38, 38-39, 39-40, 40-41, 41-42, 42-43, 43-44, 44-45, 45-46, 46-47, 47-48, 48-49, 49-50, 50-51, 51-52, 52-53, 53-54, 54-55, 55-56, 56-57, 57-58, 58-59, 59-60, 60-61, 61-62, 62-63, 63-64, 64-65, 65-66, 66-67, 67-68, 68-69, 69-70, 70-71, 71-72, 72-73, 73-74, 74-75, 75-76, 76-77, 77-78, 78-79, 79-80, 80-81, 81-82, 82-83, 83-84, 84-85, 85-86, 86-87, 87-88, 88-89, 89-90, 90-91, 91-92, 92-93, 93-94, 94-95, 95-96, 96-97, 97-98, 98-99, or 99-100 g of the composition. In one embodiment, one serving of a composition as disclosed herein comprises about 11.5 g of the composition.

In one embodiment, one spoon/level scoop of a composition described herein is one serving of the composition. In another embodiment, two spoons/level scoops of a composition described herein are one serving of the composition. In still another embodiment, three or more spoons/level scoops of a composition described herein are one serving of the composition. In various embodiments, one serving of a composition as disclosed herein is packaged as one packet, tube, vial, pouch, or bag. In various embodiments, two servings of a composition as disclosed herein are packaged as one packet, tube, vial, pouch, or bag. In various embodiments, three or more servings of a composition as disclosed herein are packaged as one packet, tube, vial, pouch, or bag.

In various embodiments, one serving of a composition as disclosed is combined with about 1-2, 2-3, 3-4, 4-5, 5-6, 6-7, 7-8, 8-9, 9-10, 10-11, 11-12, 12-13, 13-14, 14-15, or 15-16 fl. oz. water or any other suitable drinking liquid before being administrated to a subject.

In various embodiments, for every about 30 minutes, one serving of a composition as disclosed herein is administered to a subject. In some embodiments, for every about 20, 25, 30, 35, or 40 minutes, one serving of a composition as disclosed herein is administered to a subject.

In some embodiments, 1 serving of a composition described herein may be administered to a subject, for example, during an exercise of about 1-10, 10-20, 20-30, 30-40, or 40-50 minutes. In some embodiments, 2 servings of a composition described herein may be administered to a subject, for example, during an exercise of about 30-40, 40-50, 50-60, 60-70, or 70-80 minutes. In some embodiments, 3 servings of a composition described herein may be administered to a subject, for example, during an exercise of about 60-70, 70-80, 80-90, 90-100, or 100-110 minutes. In some embodiments, 4 servings of a composition described herein may be administered to a subject, for example, during an exercise of about 90-100, 100-110, 110-120, 120-130, or 130-140 minutes.

In one embodiment, 1 serving of a composition described herein may be administered to a subject during an exercise of about 1-30 minutes. In one embodiment, 2 servings of a composition described herein may be administered to a subject during an exercise of about 30-60 minutes. In one embodiment, 3 servings of a composition described herein may be administered to a subject during an exercise of about 60-90 minutes. In one embodiment, 4 servings of a composition described herein may be administered to a subject during an exercise of about 90-120 minutes.

In various embodiments, the number of servings administered to a subject during an exercise is calculated by dividing the exercise' duration (in the unit of minute) by 30 minutes. For non-limiting examples, 1 serving is for an exercise of about 15-45 minutes; 2 servings are for an exercise of about 45-75 minutes; 3 servings are for an exercise of about 75-105 minutes; and 4 servings are for an exercise of about 105-135 minutes.

In various embodiments, a subject consumes a composition described herein during exercise. In various embodiments, the subject consumes a composition described herein daily. As a non-limiting example, one, two or three servings of a composition described herein (for example, about 11.5, 23 or 34.5 g of the composition powder) is mixed with about 8, 16, or 24 fl. oz. water or any other suitable drinking liquid; let sit for about one minute; mixed again if necessary; and consumed by a subject.

Various embodiments of the present invention provide a composition. The composition may consist of or may comprise or may consist essentially of one or more or all of: calcium, magnesium, sodium, potassium, and quercetin. The composition may further comprise one or more or all of: sugar (e.g., glucose, fructose, galactose, maltose, lactose, and sucrose (for example, cane sugar and beet sugar)), dextrose, citric acid, silica, fruit flavor (e.g., lemonade, lemon, orange, mandarin orange, pineapple, pearl, apple, grape, cherry, citrus and other fruit flavors) and stevia leaf extract. In various embodiments, the fruit flavor is natural orange or mandarin orange flavor. In various embodiments, the calcium is in the form of calcium citrate, and/or calcium chloride, and/or any other suitable calcium salts or calcium sources. In various embodiments, the magnesium is in the form of magnesium citrate, and/or magnesium chloride, and/or any other suitable magnesium salts or magnesium sources. In various embodiments, the sodium is in the form of sodium citrate, and/or sodium chloride, and/or any other suitable sodium salts or sodium sources. In various embodiments, the potassium is in the form of potassium citrate, and/or chloride, and/or any other suitable potassium salts or potassium sources. In various embodiments, the quercetin is quercetin anhydrous. In exemplary embodiments, per serving, the composition may consist of or may comprise or may consist essentially of one or more or all of: about 10 mg calcium, about 40 mg magnesium, about 230 mg sodium, about 80 mg potassium, and about 250 mg quercetin. In exemplary embodiments, the composition may be used to improve exercise performance and/or recovery. In some embodiments, the effective amount of the composition to improve exercise performance and/or recovery for exercise duration of 30 minutes is about 11.5 grams. In some embodiments, the effective amount of the composition to improve exercise performance and/or recovery for exercise duration of 60 minutes is about 23 grams. In some embodiments, the effective amount of the composition to improve exercise performance and/or recovery for exercise duration of 90 minutes is about 34.5 grams. In some embodiments, the effective amount of the composition is dissolved in water. For example, 11.5, 23, and 34.5 grams of the composition may respectively be dissolved in 8, 16, and 24 ounces of water. In some embodiments, the composition is consumed during exercise.

After Exercise

In various embodiments, the present invention provides a composition for improving exercise recovery. Ingredients of the composition may include but are not limited to whey protein, pea protein, sugar (e.g., glucose, fructose, galactose, maltose, lactose, and sucrose (for example, cane sugar and beet sugar)), casein, cocoa powder, potassium citrate, pomegranate extract, sodium chloride, chocolate flavor, xanthan gum, stevia and/or stevia leaf extract, L-glutamine, and BCAA.

In various embodiments, the present invention provides a composition for improving exercise recovery. The composition may consist of or may comprise or may consist essentially of one or more or all of: whey protein, pea protein, sugar (e.g., glucose, fructose, galactose, maltose, lactose, and sucrose (for example, cane sugar and beet sugar)), casein, cocoa powder, potassium citrate, pomegranate extract, sodium chloride, chocolate flavor, xanthan gum, stevia and/or stevia leaf extract, L-glutamine, and BCAA.

In various embodiments, the whey protein is whey protein isolate 90%. In various embodiments, the pea protein is pea protein 80%—micronized. In various embodiments, the sugar (e.g., glucose, fructose, galactose, maltose, lactose, and sucrose (for example, cane sugar and beet sugar)) is granulated sugar. In various embodiments, the casein is micellar casein. In various embodiments, the cocoa powder is cocoa powder alkalized or cocoa powder (23% protein). In various embodiments, the potassium citrate is potassium citrate 36% K or potassium citrate (35.6% K). In various embodiments, the pomegranate extract is a high polyphenol pomegranate extract (e.g., POMx pomegranate extract and PomX pomegranate (75% polyphenols)). In various embodiments, the sodium chloride is sodium chloride (39% Na). In various embodiments, the chocolate flavor is natural chocolate flavor. In various embodiments, the L-glutamine is L-glutamine FCC. In various embodiments, the BCAA is BCAA 2:1:1.

In various embodiments, the present invention provides a composition for improving exercise recovery. The composition may consist of or may comprise or may consist essentially of one or more or all of: whey protein isolate, pea protein—micronized, granulated sugar (e.g., glucose, fructose, galactose, maltose, lactose, and sucrose (for example, cane sugar and beet sugar)), micellar casein, cocoa powder alkalized, potassium citrate, high polyphenol pomegranate extract (e.g., POMx pomegranate extract and PomX pomegranate (75% polyphenols)), sodium chloride, natural chocolate flavor, xanthan gum, stevia, L-glutamine, and BCAA 2:1:1.

In various embodiments, the present invention provides a composition for improving exercise recovery. The composition may consist of or may comprise or may consist essentially of one or more or all of: whey protein isolate, pea protein, sugar (e.g., glucose, fructose, galactose, maltose, lactose, and sucrose (for example, cane sugar and beet sugar)), casein, cocoa powder, potassium citrate, high polyphenol pomegranate extract (e.g., POMx pomegranate extract and PomX pomegranate (75% polyphenols)), sodium chloride, natural chocolate flavor, xanthan gum, stevia, L-glutamine FCC, and BCAA 2:1:1.

In various embodiments, the composition may comprise, or may consist essentially of, or may consist of whey protein at about 29.5-31.0%, 31.0-32.5%, 32.5-33.9%, 33.9-35.4%, 35.4-36.9%, 36.9-38.4%, 38.4-39.8%, 39.8-41.3%, 41.3-42.8%, or 42.8-44.3%, or about 36.9% by weight or volume. In various embodiments, the composition may comprise, or may consist essentially of, or may consist of pea protein at about 16.9-17.7%, 17.7-18.6%, 18.6-19.4%, 19.4-20.3%, 20.3-21.1%, 21.1-22.0%, 22.0-22.8%, 22.8-23.7%, 23.7-24.5%, or 24.5-25.4%, or about 21.1% by weight or volume. In various embodiments, the composition may comprise, or may consist essentially of, or may consist of sugar (e.g., glucose, fructose, galactose, maltose, lactose, and sucrose (for example, cane sugar and beet sugar)) at about 13.9-14.6%, 14.6-15.3%, 15.3-16.0%, 16.0-16.7%, 16.7-17.4%, 17.4-18.1%, 18.1-18.8%, 18.8-19.5%, 19.5-20.2%, or 20.2-20.9%, or about 17.4% by weight or volume. In various embodiments, the composition may comprise, or may consist essentially of, or may consist of casein at about 7.86-8.25%, 8.25-8.65%, 8.65-9.04%, 9.04-9.43%, 9.43-9.83%, 9.83-10.22%, 10.22-10.61%, 10.61-11.01%, 11.01-11.40%, or 11.40-11.79%, or about 9.83% by weight or volume. In various embodiments, the composition may comprise, or may consist essentially of, or may consist of cocoa powder at about 5.63-5.92%, 5.92-6.20%, 6.20-6.48%, 6.48-6.76%, 6.76-7.04%, 7.04-7.32%, 7.32-7.61%, 7.61-7.89%, 7.89-8.17%, or 8.17-8.45%, or about 7.04% by weight or volume. In various embodiments, the composition may comprise, or may consist essentially of, or may consist of potassium citrate at about 1.52-1.60%, 1.60-1.67%, 1.67-1.75%, 1.75-1.82%, 1.82-1.90%, 1.90-1.98%, 1.98-2.05%, 2.05-2.13%, 2.13-2.20%, or 2.20-2.28%, or about 1.90% by weight or volume. In various embodiments, the composition may comprise, or may consist essentially of, or may consist of pomegranate extract at about 1.46-1.54%, 1.54-1.61%, 1.61-1.68%, 1.68-1.76%, 1.76-1.83%, 1.83-1.90%, 1.90-1.98%, 1.98-2.05%, 2.05-2.12%, or 2.12-2.20%, or about 1.83% by weight or volume. In various embodiments, the composition may comprise, or may consist essentially of, or may consist of sodium chloride at about 1.13-1.18%, 1.18-1.24%, 1.24-1.30%, 1.30-1.35%, 1.35-1.41%, 1.41-1.46%, 1.46-1.52%, 1.52-1.58%, 1.58-1.63%, or 1.63-1.69%, or about 1.41% by weight or volume. In various embodiments, the composition may comprise, or may consist essentially of, or may consist of chocolate flavor at about 0.90-0.95%, 0.95-0.99%, 0.99-1.04%, 1.04-1.08%, 1.08-1.13%, 1.13-1.17%, 1.17-1.22%, 1.22-1.26%, 1.26-1.31%, or 1.31-1.35%, or about 1.13% by weight or volume. In various embodiments, the composition may comprise, or may consist essentially of, or may consist of xanthan gum at about 0.451-0.473%, 0.473-0.496%, 0.496-0.518%, 0.518-0.541%, 0.541-0.563%, 0.563-0.586%, 0.586-0.608%, 0.608-0.631%, 0.631-0.654%, or 0.654-0.676%, or about 0.563% by weight or volume. In various embodiments, the composition may comprise, or may consist essentially of, or may consist of stevia and/or stevia leaf extract at about 0.270-0.284%, 0.284-0.297%, 0.297-0.311%, 0.311-0.325%, 0.325-0.338%, 0.338-0.352%, 0.352-0.365%, 0.365-0.379%, 0.379-0.392%, or 0.392-0.406%, or about 0.338% by weight or volume. In various embodiments, the composition may comprise, or may consist essentially of, or may consist of L-glutamine at about 0.225-0.237%, 0.237-0.248%, 0.248-0.259%, 0.259-0.270%, 0.270-0.282%, 0.282-0.293%, 0.293-0.304%, 0.304-0.315%, 0.315-0.327%, or 0.327-0.338%, or about 0.282% by weight or volume. In various embodiments, the composition may comprise, or may consist essentially of, or may consist of BCAA at about 0.225-0.237%, 0.237-0.248%, 0.248-0.259%, 0.259-0.270%, 0.270-0.282%, 0.282-0.293%, 0.293-0.304%, 0.304-0.315%, 0.315-0.327%, or 0.327-0.338%, or about 0.282% by weight or volume. In some embodiments, the composition may consist of or may comprise or may consist essentially of one or more or all of these ingredients. In other embodiments, the composition may consist of or may comprise or may consist essentially of all of these ingredients.

In various embodiments, one serving of a composition described herein may consist of or may comprise or may consist essentially of one or more or all of: whey protein at about 29.5-31.0%, 31.0-32.5%, 32.5-33.9%, 33.9-35.4%, 35.4-36.9%, 36.9-38.4%, 38.4-39.8%, 39.8-41.3%, 41.3-42.8%, or 42.8-44.3%, or about 36.9% by weight or volume; pea protein at about 16.9-17.7%, 17.7-18.6%, 18.6-19.4%, 19.4-20.3%, 20.3-21.1%, 21.1-22.0%, 22.0-22.8%, 22.8-23.7%, 23.7-24.5%, or 24.5-25.4%, or about 21.1% by weight or volume; sugar (e.g., glucose, fructose, galactose, maltose, lactose, and sucrose (for example, cane sugar and beet sugar)) at about 13.9-14.6%, 14.6-15.3%, 15.3-16.0%, 16.0-16.7%, 16.7-17.4%, 17.4-18.1%, 18.1-18.8%, 18.8-19.5%, 19.5-20.2%, or 20.2-20.9%, or about 17.4% by weight or volume; casein at about 7.86-8.25%, 8.25-8.65%, 8.65-9.04%, 9.04-9.43%, 9.43-9.83%, 9.83-10.22%, 10.22-

10.61%, 10.61-11.01%, 11.01-11.40%, or 11.40-11.79%, or about 9.83% by weight or volume; cocoa powder at about 5.63-5.92%, 5.92-6.20%, 6.20-6.48%, 6.48-6.76%, 6.76-7.04%, 7.04-7.32%, 7.32-7.61%, 7.61-7.89%, 7.89-8.17%, or 8.17-8.45%, or about 7.04% by weight or volume; potassium citrate at about 1.52-1.60%, 1.60-1.67%, 1.67-1.75%, 1.75-1.82%, 1.82-1.90%, 1.90-1.98%, 1.98-2.05%, 2.05-2.13%, 2.13-2.20%, or 2.20-2.28%, or about 1.90% by weight or volume; pomegranate extract at about 1.46-1.54%, 1.54-1.61%, 1.61-1.68%, 1.68-1.76%, 1.76-1.83%, 1.83-1.90%, 1.90-1.98%, 1.98-2.05%, 2.05-2.12%, or 2.12-2.20%, or about 1.83% by weight or volume; sodium chloride at about 1.13-1.18%, 1.18-1.24%, 1.24-1.30%, 1.30-1.35%, 1.35-1.41%, 1.41-1.46%, 1.46-1.52%, 1.52-1.58%, 1.58-1.63%, or 1.63-1.69%, or about 1.41% by weight or volume; chocolate flavor at about 0.90-0.95%, 0.95-0.99%, 0.99-1.04%, 1.04-1.08%, 1.08-1.13%, 1.13-1.17%, 1.17-1.22%, 1.22-1.26%, 1.26-1.31%, or 1.31-1.35%, or about 1.13% by weight or volume; xanthan gum at about 0.451-0.473%, 0.473-0.496%, 0.496-0.518%, 0.518-0.541%, 0.541-0.563%, 0.563-0.586%, 0.586-0.608%, 0.608-0.631%, 0.631-0.654%, or 0.654-0.676%, or about 0.563% by weight or volume; stevia and/or stevia leaf extract at about 0.270-0.284%, 0.284-0.297%, 0.297-0.311%, 0.311-0.325%, 0.325-0.338%, 0.338-0.352%, 0.352-0.365%, 0.365-0.379%, 0.379-0.392%, or 0.392-0.406%, or about 0.338% by weight or volume; L-glutamine at about 0.225-0.237%, 0.237-0.248%, 0.248-0.259%, 0.259-0.270%, 0.270-0.282%, 0.282-0.293%, 0.293-0.304%, 0.304-0.315%, 0.315-0.327%, or 0.327-0.338%, or about 0.282% by weight or volume; and BCAA at about 0.225-0.237%, 0.237-0.248%, 0.248-0.259%, 0.259-0.270%, 0.270-0.282%, 0.282-0.293%, 0.293-0.304%, 0.304-0.315%, 0.315-0.327%, or 0.327-0.338%, or about 0.282% by weight or volume. In some embodiments, the composition may consist of or may comprise or may consist essentially of one or more or all of these ingredients. In other embodiments, the composition may consist of or may comprise or may consist essentially of all of these ingredients.

In various embodiments, the composition may comprise, or may consist essentially of, or may consist of whey protein at about 32.5-34.1%, 34.1-35.8%, 35.8-37.4%, 37.4-39.0%, 39.0-40.7%, 40.7-42.3%, 42.3-43.9%, 43.9-45.5%, 45.5-47.2%, or 47.2-48.8%, or about 40.7% by weight or volume. In various embodiments, the composition may comprise, or may consist essentially of, or may consist of pea protein at about 14.6-15.4%, 15.4-16.1%, 16.1-16.8%, 16.8-17.6%, 17.6-18.3%, 18.3-19.0%, 19.0-19.8%, 19.8-20.5%, 20.5-21.2%, or 21.2-22.0%, or about 18.3% by weight or volume. In various embodiments, the composition may comprise, or may consist essentially of, or may consist of sugar (e.g., glucose, fructose, galactose, maltose, lactose, and sucrose (for example, cane sugar and beet sugar)) at about 11.7-12.3%, 12.3-12.8%, 12.8-13.4%, 13.4-14.0%, 14.0-14.6%, 14.6-15.2%, 15.2-15.8%, 15.8-16.3%, 16.3-16.9%, or 16.9-17.5%, or about 14.6% by weight or volume. In various embodiments, the composition may comprise, or may consist essentially of, or may consist of casein at about 6.65-6.98%, 6.98-7.32%, 7.32-7.65%, 7.65-7.98%, 7.98-8.31%, 8.31-8.65%, 8.65-8.98%, 8.98-9.31%, 9.31-9.65%, or 9.65-9.98%, or about 8.31% by weight or volume. In various embodiments, the composition may comprise, or may consist essentially of, or may consist of cocoa powder at about 8.8-9.2%, 9.2-9.7%, 9.7-10.1%, 10.1-10.5%, 10.5-11.0%, 11.0-11.4%, 11.4-11.9%, 11.9-12.3%, 12.3-12.7%, or 12.7-13.2%, or about 11.0% by weight or volume. In various embodiments, the composition may comprise, or may consist essentially of, or may consist of potassium citrate at about 1.95-2.05%, 2.05-2.15%, 2.15-2.24%, 2.24-2.34%, 2.34-2.44%, 2.44-2.54%, 2.54-2.63%, 2.63-2.73%, 2.73-2.83%, or 2.83-2.93%, or about 2.44% by weight or volume. In various embodiments, the composition may comprise, or may consist essentially of, or may consist of pomegranate extract at about 1.27-1.33%, 1.33-1.40%, 1.40-1.46%, 1.46-1.52%, 1.52-1.59%, 1.59-1.65%, 1.65-1.71%, 1.71-1.78%, 1.78-1.84%, or 1.84-1.90%, or about 1.59% by weight or volume. In various embodiments, the composition may comprise, or may consist essentially of, or may consist of sodium chloride at about 0.98-1.02%, 1.02-1.07%, 1.07-1.12%, 1.12-1.17%, 1.17-1.22%, 1.22-1.27%, 1.27-1.32%, 1.32-1.37%, 1.37-1.41%, or 1.41-1.46%, or about 1.22% by weight or volume. In various embodiments, the composition may comprise, or may consist essentially of, or may consist of chocolate flavor at about 0.780-0.820%, 0.820-0.859%, 0.859-0.898%, 0.898-0.937%, 0.937-0.976%, 0.976-1.015%, 1.015-1.054%, 1.054-1.093%, 1.093-1.132%, or 1.132-1.171%, or about 0.976% by weight or volume. In various embodiments, the composition may comprise, or may consist essentially of, or may consist of xanthan gum at about 0.195-0.205%, 0.205-0.215%, 0.215-0.224%, 0.224-0.234%, 0.234-0.244%, 0.244-0.254%, 0.254-0.263%, 0.263-0.273%, 0.273-0.283%, or 0.283-0.293%, or about 0.244% by weight or volume. In various embodiments, the composition may comprise, or may consist essentially of, or may consist of stevia and/or stevia leaf extract at about 0.176-0.184%, 0.184-0.193%, 0.193-0.202%, 0.202-0.211%, 0.211-0.220%, 0.220-0.228%, 0.228-0.237%, 0.237-0.246%, 0.246-0.255%, or 0.255-0.263%, or about 0.220% by weight or volume. In various embodiments, the composition may comprise, or may consist essentially of, or may consist of L-glutamine at about 0.195-0.205%, 0.205-0.215%, 0.215-0.224%, 0.224-0.234%, 0.234-0.244%, 0.244-0.254%, 0.254-0.263%, 0.263-0.273%, 0.273-0.283%, or 0.283-0.293%, or about 0.244% by weight or volume. In various embodiments, the composition may comprise, or may consist essentially of, or may consist of BCAA at about 0.195-0.205%, 0.205-0.215%, 0.215-0.224%, 0.224-0.234%, 0.234-0.244%, 0.244-0.254%, 0.254-0.263%, 0.263-0.273%, 0.273-0.283%, or 0.283-0.293%, or about 0.244% by weight or volume. In some embodiments, the composition may consist of or may comprise or may consist essentially of one or more or all of these ingredients. In other embodiments, the composition may consist of or may comprise or may consist essentially of all of these ingredients.

In various embodiments, one serving of a composition described herein may consist of or may comprise or may consist essentially of one or more or all of: whey protein at about 32.5-34.1%, 34.1-35.8%, 35.8-37.4%, 37.4-39.0%, 39.0-40.7%, 40.7-42.3%, 42.3-43.9%, 43.9-45.5%, 45.5-47.2%, or 47.2-48.8%, or about 40.7% by weight or volume; pea protein at about 14.6-15.4%, 15.4-16.1%, 16.1-16.8%, 16.8-17.6%, 17.6-18.3%, 18.3-19.0%, 19.0-19.8%, 19.8-20.5%, 20.5-21.2%, or 21.2-22.0%, or about 18.3% by weight or volume; sugar (e.g., glucose, fructose, galactose, maltose, lactose, and sucrose (for example, cane sugar and beet sugar)) at about 11.7-12.3%, 12.3-12.8%, 12.8-13.4%, 13.4-14.0%, 14.0-14.6%, 14.6-15.2%, 15.2-15.8%, 15.8-16.3%, 16.3-16.9%, or 16.9-17.5%, or about 14.6% by weight or volume; casein at about 6.65-6.98%, 6.98-7.32%, 7.32-7.65%, 7.65-7.98%, 7.98-8.31%, 8.31-8.65%, 8.65-8.98%, 8.98-9.31%, 9.31-9.65%, or 9.65-9.98%, or about 8.31% by weight or volume; cocoa powder at about 8.8-9.2%, 9.2-9.7%, 9.7-10.1%, 10.1-10.5%, 10.5-11.0%, 11.0-

11.4%, 11.4-11.9%, 11.9-12.3%, 12.3-12.7%, or 12.7-13.2%, or about 11.0% by weight or volume; potassium citrate at about 1.95-2.05%, 2.05-2.15%, 2.15-2.24%, 2.24-2.34%, 2.34-2.44%, 2.44-2.54%, 2.54-2.63%, 2.63-2.73%, 2.73-2.83%, or 2.83-2.93%, or about 2.44% by weight or volume; pomegranate extract at about 1.27-1.33%, 1.33-1.40%, 1.40-1.46%, 1.46-1.52%, 1.52-1.59%, 1.59-1.65%, 1.65-1.71%, 1.71-1.78%, 1.78-1.84%, or 1.84-1.90%, or about 1.59% by weight or volume; sodium chloride at about 0.98-1.02%, 1.02-1.07%, 1.07-1.12%, 1.12-1.17%, 1.17-1.22%, 1.22-1.27%, 1.27-1.32%, 1.32-1.37%, 1.37-1.41%, or 1.41-1.46%, or about 1.22% by weight or volume; chocolate flavor at about 0.780-0.820%, 0.820-0.859%, 0.859-0.898%, 0.898-0.937%, 0.937-0.976%, 0.976-1.015%, 1.015-1.054%, 1.054-1.093%, 1.093-1.132%, or 1.132-1.171%, or about 0.976% by weight or volume; xanthan gum at about 0.195-0.205%, 0.205-0.215%, 0.215-0.224%, 0.224-0.234%, 0.234-0.244%, 0.244-0.254%, 0.254-0.263%, 0.263-0.273%, 0.273-0.283%, or 0.283-0.293%, or about 0.244% by weight or volume; stevia and/or stevia leaf extract at about 0.176-0.184%, 0.184-0.193%, 0.193-0.202%, 0.202-0.211%, 0.211-0.220%, 0.220-0.228%, 0.228-0.237%, 0.237-0.246%, 0.246-0.255%, or 0.255-0.263%, or about 0.220% by weight or volume; L-glutamine at about 0.195-0.205%, 0.205-0.215%, 0.215-0.224%, 0.224-0.234%, 0.234-0.244%, 0.244-0.254%, 0.254-0.263%, 0.263-0.273%, 0.273-0.283%, or 0.283-0.293%, or about 0.244% by weight or volume; and BCAA at about 0.195-0.205%, 0.205-0.215%, 0.215-0.224%, 0.224-0.234%, 0.234-0.244%, 0.244-0.254%, 0.254-0.263%, 0.263-0.273%, 0.273-0.283%, or 0.283-0.293%, or about 0.244% by weight or volume. In some embodiments, the composition may consist of or may comprise or may consist essentially of one or more or all of these ingredients. In other embodiments, the composition may consist of or may comprise or may consist essentially of all of these ingredients.

In various embodiments, the composition may comprise, or may consist essentially of, or may consist of whey protein at about 10.5-11.0, 11.0-11.5, 11.5-12.0, 12.0-12.6, 12.6-13.1, 13.1-13.6, 13.6-14.1, 14.1-14.7, 14.7-15.2, or 15.2-15.7 g, or about 13.1 g. In various embodiments, the composition may comprise, or may consist essentially of, or may consist of pea protein at about 6.00-6.30, 6.30-6.60, 6.60-6.90, 6.90-7.20, 7.20-7.50, 7.50-7.80, 7.80-8.10, 8.10-8.40, 8.40-8.70, or 8.70-9.00 g, or about 7.50 g. In various embodiments, the composition may comprise, or may consist essentially of, or may consist of sugar (e.g., glucose, fructose, galactose, maltose, lactose, and sucrose (for example, cane sugar and beet sugar)) at about 4.94-5.18, 5.18-5.43, 5.43-5.68, 5.68-5.93, 5.93-6.17, 6.17-6.42, 6.42-6.67, 6.67-6.91, 6.91-7.16, or 7.16-7.41 g, or about 6.17 g. In various embodiments, the composition may comprise, or may consist essentially of, or may consist of casein at about 2.79-2.93, 2.93-3.07, 3.07-3.21, 3.21-3.35, 3.35-3.49, 3.49-3.63, 3.63-3.77, 3.77-3.91, 3.91-4.05, or 4.05-4.19 g, or about 3.49 g. In various embodiments, the composition may comprise, or may consist essentially of, or may consist of cocoa powder at about 2.00-2.10, 2.10-2.20, 2.20-2.30, 2.30-2.40, 2.40-2.50, 2.50-2.60, 2.60-2.70, 2.70-2.80, 2.80-2.90, or 2.90-3.00 g, or about 2.50 g. In various embodiments, the composition may comprise, or may consist essentially of, or may consist of potassium citrate at about 0.539-0.566, 0.566-0.593, 0.593-0.620, 0.620-0.647, 0.647-0.674, 0.674-0.701, 0.701-0.728, 0.728-0.755, 0.755-0.782, or 0.782-0.809 g, or about 0.674 g. In various embodiments, the composition may comprise, or may consist essentially of, or may consist of pomegranate extract at about 0.520-0.546, 0.546-0.572, 0.572-0.598, 0.598-0.624, 0.624-0.650, 0.650-0.676, 0.676-0.702, 0.702-0.728, 0.728-0.754, or 0.754-0.780 g, or about 0.650 g. In various embodiments, the composition may comprise, or may consist essentially of, or may consist of sodium chloride at about 0.400-0.420, 0.420-0.440, 0.440-0.460, 0.460-0.480, 0.480-0.500, 0.500-0.520, 0.520-0.540, 0.540-0.560, 0.560-0.580, or 0.580-0.600 g, or about 0.500 g. In various embodiments, the composition may comprise, or may consist essentially of, or may consist of chocolate flavor at about 0.320-0.336, 0.336-0.352, 0.352-0.368, 0.368-0.384, 0.384-0.400, 0.400-0.416, 0.416-0.432, 0.432-0.448, 0.448-0.464, or 0.464-0.480 g, or about 0.400 g. In various embodiments, the composition may comprise, or may consist essentially of, or may consist of xanthan gum at about 0.160-0.168, 0.168-0.176, 0.176-0.184, 0.184-0.192, 0.192-0.200, 0.200-0.208, 0.208-0.216, 0.216-0.224, 0.224-0.232, or 0.232-0.240 g, or about 0.200 g. In various embodiments, the composition may comprise, or may consist essentially of, or may consist of stevia and/or stevia leaf extract at about 0.096-0.101, 0.101-0.106, 0.106-0.110, 0.110-0.115, 0.115-0.120, 0.120-0.125, 0.125-0.130, 0.130-0.134, 0.134-0.139, or 0.139-0.144 g, or about 0.120 g. In various embodiments, the composition may comprise, or may consist essentially of, or may consist of L-glutamine at about 0.080-0.084, 0.084-0.088, 0.088-0.092, 0.092-0.096, 0.096-0.100, 0.100-0.104, 0.104-0.108, 0.108-0.112, 0.112-0.116, or 0.116-0.120 g, or about 0.100 g. In various embodiments, the composition may comprise, or may consist essentially of, or may consist of BCAA at about 0.080-0.084, 0.084-0.088, 0.088-0.092, 0.092-0.096, 0.096-0.100, 0.100-0.104, 0.104-0.108, 0.108-0.112, 0.112-0.116, or 0.116-0.120 g, or about 0.100 g. In some embodiments, the composition may consist of or may comprise or may consist essentially of one or more or all of these ingredients. In other embodiments, the composition may comprise or may consist essentially of all of these ingredients.

In various embodiments, one serving of a composition described herein may consist of or may comprise or may consist essentially of one or more or all of: whey protein at about 10.5-11.0, 11.0-11.5, 11.5-12.0, 12.0-12.6, 12.6-13.1, 13.1-13.6, 13.6-14.1, 14.1-14.7, 14.7-15.2, or 15.2-15.7 g, or about 13.1 g; pea protein at about 6.00-6.30, 6.30-6.60, 6.60-6.90, 6.90-7.20, 7.20-7.50, 7.50-7.80, 7.80-8.10, 8.10-8.40, 8.40-8.70, or 8.70-9.00 g, or about 7.50 g; sugar (e.g., glucose, fructose, galactose, maltose, lactose, and sucrose (for example, cane sugar and beet sugar)) at about 4.94-5.18, 5.18-5.43, 5.43-5.68, 5.68-5.93, 5.93-6.17, 6.17-6.42, 6.42-6.67, 6.67-6.91, 6.91-7.16, or 7.16-7.41 g, or about 6.17 g; casein at about 2.79-2.93, 2.93-3.07, 3.07-3.21, 3.21-3.35, 3.35-3.49, 3.49-3.63, 3.63-3.77, 3.77-3.91, 3.91-4.05, or 4.05-4.19 g, or about 3.49 g; cocoa powder at about 2.00-2.10, 2.10-2.20, 2.20-2.30, 2.30-2.40, 2.40-2.50, 2.50-2.60, 2.60-2.70, 2.70-2.80, 2.80-2.90, or 2.90-3.00 g, or about 2.50 g; potassium citrate at about 0.539-0.566, 0.566-0.593, 0.593-0.620, 0.620-0.647, 0.647-0.674, 0.674-0.701, 0.701-0.728, 0.728-0.755, 0.755-0.782, or 0.782-0.809 g, or about 0.674 g; pomegranate extract at about 0.520-0.546, 0.546-0.572, 0.572-0.598, 0.598-0.624, 0.624-0.650, 0.650-0.676, 0.676-0.702, 0.702-0.728, 0.728-0.754, or 0.754-0.780 g, or about 0.650 g; sodium chloride at about 0.400-0.420, 0.420-0.440, 0.440-0.460, 0.460-0.480, 0.480-0.500, 0.500-0.520, 0.520-0.540, 0.540-0.560, 0.560-0.580, or 0.580-0.600 g, or about 0.500 g; chocolate flavor at about 0.320-0.336, 0.336-0.352, 0.352-0.368, 0.368-0.384, 0.384-0.400, 0.400-0.416, 0.416-0.432, 0.432-0.448, 0.448-0.464, or 0.464-0.480 g, or about 0.400 g; xanthan gum at about 0.160-0.168, 0.168-

0.176, 0.176-0.184, 0.184-0.192, 0.192-0.200, 0.200-0.208, 0.208-0.216, 0.216-0.224, 0.224-0.232, or 0.232-0.240 g, or about 0.200 g; stevia and/or stevia leaf extract at about 0.096-0.101, 0.101-0.106, 0.106-0.110, 0.110-0.115, 0.115-0.120, 0.120-0.125, 0.125-0.130, 0.130-0.134, 0.134-0.139, or 0.139-0.144 g, or about 0.120 g; L-glutamine at about 0.080-0.084, 0.084-0.088, 0.088-0.092, 0.092-0.096, 0.096-0.100, 0.100-0.104, 0.104-0.108, 0.108-0.112, 0.112-0.116, or 0.116-0.120 g, or about 0.100 g; and BCAA at about 0.080-0.084, 0.084-0.088, 0.088-0.092, 0.092-0.096, 0.096-0.100, 0.100-0.104, 0.104-0.108, 0.108-0.112, 0.112-0.116, or 0.116-0.120 g, or about 0.100 g. In some embodiments, the composition may consist of or may comprise or may consist essentially of one or more or all of these ingredients. In other embodiments, the composition may consist of or may comprise or may consist essentially of all of these ingredients.

In various embodiments, the composition may comprise, or may consist essentially of, or may consist of whey protein at about 13.3-14.0, 14.0-14.7, 14.7-15.3, 15.3-16.0, 16.0-16.7, 16.7-17.3, 17.3-18.0, 18.0-18.7, 18.7-19.3, or 19.3-20.0 g, or about 16.7 g. In various embodiments, the composition may comprise, or may consist essentially of, or may consist of pea protein at about 6.00-6.30, 6.30-6.60, 6.60-6.90, 6.90-7.20, 7.20-7.50, 7.50-7.80, 7.80-8.10, 8.10-8.40, 8.40-8.70, or 8.70-9.00 g, or about 7.50 g. In various embodiments, the composition may comprise, or may consist essentially of, or may consist of sugar (e.g., glucose, fructose, galactose, maltose, lactose, and sucrose (for example, cane sugar and beet sugar)) at about 4.79-5.03, 5.03-5.27, 5.27-5.51, 5.51-5.74, 5.74-5.98, 5.98-6.22, 6.22-6.46, 6.46-6.70, 6.70-6.94, or 6.94-7.18 g, or about 5.98 g. In various embodiments, the composition may comprise, or may consist essentially of, or may consist of casein at about 2.73-2.86, 2.86-3.00, 3.00-3.14, 3.14-3.27, 3.27-3.41, 3.41-3.55, 3.55-3.68, 3.68-3.82, 3.82-3.95, or 3.95-4.09 g, or about 3.41 g. In various embodiments, the composition may comprise, or may consist essentially of, or may consist of cocoa powder at about 3.60-3.78, 3.78-3.96, 3.96-4.14, 4.14-4.32, 4.32-4.50, 4.50-4.68, 4.68-4.86, 4.86-5.04, 5.04-5.22, or 5.22-5.40 g, or about 4.50 g. In various embodiments, the composition may comprise, or may consist essentially of, or may consist of potassium citrate at about 0.80-0.84, 0.84-0.88, 0.88-0.92, 0.92-0.96, 0.96-1.00, 1.00-1.04, 1.04-1.08, 1.08-1.12, 1.12-1.16, or 1.16-1.20 g, or about 1.00 g. In various embodiments, the composition may comprise, or may consist essentially of, or may consist of pomegranate extract at about 0.520-0.546, 0.546-0.572, 0.572-0.598, 0.598-0.624, 0.624-0.650, 0.650-0.676, 0.676-0.702, 0.702-0.728, 0.728-0.754, or 0.754-0.780 g, or about 0.650 g. In various embodiments, the composition may comprise, or may consist essentially of, or may consist of sodium chloride at about 0.400-0.420, 0.420-0.440, 0.440-0.460, 0.460-0.480, 0.480-0.500, 0.500-0.520, 0.520-0.540, 0.540-0.560, 0.560-0.580, or 0.580-0.600 g, or about 0.500 g. In various embodiments, the composition may comprise, or may consist essentially of, or may consist of chocolate flavor at about 0.320-0.336, 0.336-0.352, 0.352-0.368, 0.368-0.384, 0.384-0.400, 0.400-0.416, 0.416-0.432, 0.432-0.448, 0.448-0.464, or 0.464-0.480 g, or about 0.400 g. In various embodiments, the composition may comprise, or may consist essentially of, or may consist of xanthan gum at about 0.080-0.084, 0.084-0.088, 0.088-0.092, 0.092-0.096, 0.096-0.100, 0.100-0.104, 0.104-0.108, 0.108-0.112, 0.112-0.116, or 0.116-0.120 g, or about 0.100 g. In various embodiments, the composition may comprise, or may consist essentially of, or may consist of stevia and/or stevia leaf extract at about 0.072-0.076, 0.076-0.079, 0.079-0.083, 0.083-0.086, 0.086-0.090, 0.090-0.094, 0.094-0.097, 0.097-0.101, 0.101-0.104, or 0.104-0.108 g, or about 0.090 g. In various embodiments, the composition may comprise, or may consist essentially of, or may consist of L-glutamine at about 0.080-0.084, 0.084-0.088, 0.088-0.092, 0.092-0.096, 0.096-0.100, 0.100-0.104, 0.104-0.108, 0.108-0.112, 0.112-0.116, or 0.116-0.120 g, or about 0.100 g. In various embodiments, the composition may comprise, or may consist essentially of, or may consist of BCAA at about 0.080-0.084, 0.084-0.088, 0.088-0.092, 0.092-0.096, 0.096-0.100, 0.100-0.104, 0.104-0.108, 0.108-0.112, 0.112-0.116, or 0.116-0.120 g, or about 0.100 g. In some embodiments, the composition may consist of or may comprise or may consist essentially of one or more or all of these ingredients. In other embodiments, the composition may consist of or may comprise or may consist essentially of all of these ingredients.

In various embodiments, one serving of a composition described herein may consist of or may comprise or may consist essentially of one or more or all of: whey protein at about 13.3-14.0, 14.0-14.7, 14.7-15.3, 15.3-16.0, 16.0-16.7, 16.7-17.3, 17.3-18.0, 18.0-18.7, 18.7-19.3, or 19.3-20.0 g, or about 16.7 g; pea protein at about 6.00-6.30, 6.30-6.60, 6.60-6.90, 6.90-7.20, 7.20-7.50, 7.50-7.80, 7.80-8.10, 8.10-8.40, 8.40-8.70, or 8.70-9.00 g, or about 7.50 g; sugar (e.g., glucose, fructose, galactose, maltose, lactose, and sucrose (for example, cane sugar and beet sugar)) at about 4.79-5.03, 5.03-5.27, 5.27-5.51, 5.51-5.74, 5.74-5.98, 5.98-6.22, 6.22-6.46, 6.46-6.70, 6.70-6.94, or 6.94-7.18 g, or about 5.98 g; casein at about 2.73-2.86, 2.86-3.00, 3.00-3.14, 3.14-3.27, 3.27-3.41, 3.41-3.55, 3.55-3.68, 3.68-3.82, 3.82-3.95, or 3.95-4.09 g, or about 3.41 g; cocoa powder at about 3.60-3.78, 3.78-3.96, 3.96-4.14, 4.14-4.32, 4.32-4.50, 4.50-4.68, 4.68-4.86, 4.86-5.04, 5.04-5.22, or 5.22-5.40 g, or about 4.50 g; potassium citrate at about 0.80-0.84, 0.84-0.88, 0.88-0.92, 0.92-0.96, 0.96-1.00, 1.00-1.04, 1.04-1.08, 1.08-1.12, 1.12-1.16, or 1.16-1.20 g, or about 1.00 g; pomegranate extract at about 0.520-0.546, 0.546-0.572, 0.572-0.598, 0.598-0.624, 0.624-0.650, 0.650-0.676, 0.676-0.702, 0.702-0.728, 0.728-0.754, or 0.754-0.780 g, or about 0.650 g; sodium chloride at about 0.400-0.420, 0.420-0.440, 0.440-0.460, 0.460-0.480, 0.480-0.500, 0.500-0.520, 0.520-0.540, 0.540-0.560, 0.560-0.580, or 0.580-0.600 g, or about 0.500 g; chocolate flavor at about 0.320-0.336, 0.336-0.352, 0.352-0.368, 0.368-0.384, 0.384-0.400, 0.400-0.416, 0.416-0.432, 0.432-0.448, 0.448-0.464, or 0.464-0.480 g, or about 0.400 g; xanthan gum at about 0.080-0.084, 0.084-0.088, 0.088-0.092, 0.092-0.096, 0.096-0.100, 0.100-0.104, 0.104-0.108, 0.108-0.112, 0.112-0.116, or 0.116-0.120 g, or about 0.100 g; stevia and/or stevia leaf extract at about 0.072-0.076, 0.076-0.079, 0.079-0.083, 0.083-0.086, 0.086-0.090, 0.090-0.094, 0.094-0.097, 0.097-0.101, 0.101-0.104, or 0.104-0.108 g, or about 0.090 g; L-glutamine at about 0.080-0.084, 0.084-0.088, 0.088-0.092, 0.092-0.096, 0.096-0.100, 0.100-0.104, 0.104-0.108, 0.108-0.112, 0.112-0.116, or 0.116-0.120 g, or about 0.100 g; and BCAA at about 0.080-0.084, 0.084-0.088, 0.088-0.092, 0.092-0.096, 0.096-0.100, 0.100-0.104, 0.104-0.108, 0.108-0.112, 0.112-0.116, or 0.116-0.120 g, or about 0.100 g. In some embodiments, the composition may consist of or may comprise or may consist essentially of one or more or all of these ingredients. In other embodiments, the composition may consist of or may comprise or may consist essentially of all of these ingredients.

In various embodiments, one serving of a composition as disclosed herein is administered to a subject. In various embodiments, one serving of a composition as disclosed herein comprise about 1-2, 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, 20-21, 21-22, 22-23, 23-24, 24-25, 25-26, 26-27, 27-28, 28-29, 29-30, 30-31, 31-32, 32-33, 33-34, 34-35, 35-36, 36-37, 37-38, 38-39, 39-40, 40-41, 41-42, 42-43, 43-44, 44-45, 45-46, 46-47, 47-48, 48-49, 49-50, 50-51, 51-52, 52-53, 53-54, 54-55, 55-56, 56-57, 57-58, 58-59, 59-60, 60-61, 61-62, 62-63, 63-64, 64-65, 65-66, 66-67, 67-68, 68-69, 69-70, 70-71, 71-72, 72-73, 73-74, 74-75, 75-76, 76-77, 77-78, 78-79, 79-80, 80-81, 81-82, 82-83, 83-84, 84-85, 85-86, 86-87, 87-88, 88-89, 89-90, 90-91, 91-92, 92-93, 93-94, 94-95, 95-96, 96-97, 97-98, 98-99, or 99-100 g of the composition. In one embodiment, one serving of a composition as disclosed herein comprises about 35.5 g of the composition. In another embodiment, one serving of a composition as disclosed herein comprises about 41 g of the composition.

In one embodiment, one spoon/level scoop of a composition described herein is one serving of the composition. In another embodiment, two spoons/level scoops of a composition described herein are one serving of the composition. In still another embodiment, three or more spoons/level scoops of a composition described herein are one serving of the composition. In various embodiments, one serving of a composition as disclosed herein is packaged as one packet, tube, vial, pouch, or bag. In various embodiments, two servings of a composition as disclosed herein are packaged as one packet, tube, vial, pouch, or bag. In various embodiments, three or more servings of a composition as disclosed herein are packaged as one packet, tube, vial, pouch, or bag.

In various embodiments, one serving of a composition as disclosed is combined with about 1-2, 2-3, 3-4, 4-5, 5-6, 6-7, 7-8, 8-9, 9-10, 10-11, 11-12, 12-13, 13-14, 14-15, or 15-16 fl. oz. water or any other suitable drinking liquid before being administrated to a subject.

In some embodiments, 1 serving of a composition described herein may be administered to a subject, for example, if the subject's body weight is below about 130, 140, 150, 160, 170, 180, or 190 pounds. In one embodiment, 1 serving of a composition described herein may be administered to a subject having a body weight below 160 pounds. In other embodiments, 2 servings of a composition described herein may be administered to a subject at one time, for example, if the subject's body weight is at or above about 130, 140, 150, 160, 170, 180, or 190 pounds. In one embodiment, 2 servings of a composition described herein may be administered to a subject having a body weight at or above 160 pounds.

In various embodiments, a subject consumes a composition described herein after exercise. In various embodiments, the subject consumes a composition described herein daily. As a non-limiting example, one serving of a composition described herein (for example, about 35.5 g of the composition powder) is mixed with about 8 fl. oz. water or any other suitable drinking liquid; let sit for about one minute; mixed again if necessary; and consumed by a subject. In one embodiment, the composition is consumed by a subject within a few minutes after preparation.

Various embodiments of the present invention provide a composition. The composition may consist of or may comprise or may consist essentially of one or more or all of: calcium, magnesium, sodium, potassium, pomegranate extract and a combination of whey protein isolate, pea protein isolate, micellar casein, branched chain amino acids (BCAAs), L-leucine, valine, isoleucine and L-glutamine. The composition may further comprise one or more or all of: sugar (e.g., glucose, fructose, galactose, maltose, lactose, and sucrose (for example, cane sugar and beet sugar)), cocoa powder, chocolate flavor, xanthan gum and stevia leaf extract. In various embodiments, the calcium is in the form of calcium citrate, and/or calcium chloride, and/or any other suitable calcium salts or calcium sources. In various embodiments, the magnesium is in the form of magnesium citrate, and/or magnesium chloride, and/or any other suitable magnesium salts or magnesium sources. In various embodiments, the sodium is in the form of sodium citrate, and/or sodium chloride, and/or any other suitable sodium salts or sodium sources. In various embodiments, the potassium is in the form of potassium citrate, and/or chloride, and/or any other suitable potassium salts or potassium sources. In some embodiments, L-leucine, valine and isoleucine are at a ratio of 2:1:1. In exemplary embodiments, per serving, the composition may consist of or may comprise or may consist essentially of one or more or all of: about 140 mg calcium, about 40 mg magnesium, about 300 mg sodium, about 420 mg potassium, about 650 mg pomegranate extract, and about 23 g of the combination of whey protein isolate, pea protein isolate, micellar casein, branched chain amino acids (BCAAs), L-leucine, valine, isoleucine and L-glutamine. In exemplar embodiments, the composition may be used to improve exercise recovery. In some embodiments, the effective amount of the composition to improve exercise recovery is about 35.5 grams. In some embodiments, the effective amount of the composition is dissolved in water. For example, 35.5 grams of the composition may be dissolved in 8 ounces of water. In some embodiments, the composition is consumed after exercise, for example, within 30 minutes after exercise.

Before Sleep

In various embodiments, the present invention provides a composition for improving exercise recovery. Ingredients of the composition may include but are not limited to casein, sugar (e.g., glucose, fructose, galactose, maltose, lactose, and sucrose (for example, cane sugar and beet sugar)), vanilla flavor, tart cherry extract, sodium chloride, BCAA, L-glutamine, stevia and/or stevia leaf extract, and xanthan gum.

In various embodiments, the present invention provides a composition for improving exercise recovery. The composition may consist of or may comprise or may consist essentially of one or more or all of: casein, sugar (e.g., glucose, fructose, galactose, maltose, lactose, and sucrose (for example, cane sugar and beet sugar)), vanilla flavor, tart cherry extract, sodium chloride, BCAA, L-glutamine, stevia and/or stevia leaf extract, and xanthan gum.

In various embodiments, the present invention provides a composition for improving exercise recovery. The composition may consist of or may comprise or may consist essentially of one or more or all of: casein, sugar (e.g., glucose, fructose, galactose, maltose, lactose, and sucrose (for example, cane sugar and beet sugar)), vanilla flavor, tart cherry extract, sodium chloride, BCAA, L-glutamine, stevia and/or stevia leaf extract, and xanthan gum.

In various embodiments, the present invention provides a composition for improving exercise recovery. The composition may consist of or may comprise or may consist essentially of one or more or all of: casein, sugar (e.g., glucose, fructose, galactose, maltose, lactose, and sucrose (for example, cane sugar and beet sugar)), vanilla flavor, tart cherry extract, sodium chloride, stevia and/or stevia leaf extract, and xanthan gum.

In various embodiments, the casein is micellar casein. In various embodiments, the sugar (e.g., glucose, fructose, galactose, maltose, lactose, and sucrose (for example, cane sugar and beet sugar)) is granulated sugar. In various embodiments, the vanilla flavor is natural vanilla flavor, natural vanilla chamomile flavor or vanilla chamomile wild flavor. In various embodiments, the BCAA is BCAA 2:1:1.

In various embodiments, the present invention provides a composition for improving exercise recovery. The composition may consist of or may comprise or may consist essentially of one or more or all of: micellar casein; granulated sugar (e.g., glucose, fructose, galactose, maltose, lactose, and sucrose (for example, cane sugar and beet sugar)); vanilla flavor; tart cherry extract; sodium chloride; BCAA 2:1:1; L-glutamine; stevia; and xanthan gum. In various embodiments, the vanilla flavor is natural vanilla flavor, natural vanilla chamomile flavor or vanilla chamomile wild flavor.

In various embodiments, the present invention provides a composition for improving exercise recovery. The composition may consist of or may comprise or may consist essentially of one or more or all of: casein; sugar (e.g., glucose, fructose, galactose, maltose, lactose, and sucrose (for example, cane sugar and beet sugar)); vanilla flavor; tart cherry; sodium chloride; stevia; and xanthan gum. In various embodiments, the vanilla flavor is natural vanilla flavor, natural vanilla chamomile flavor or vanilla chamomile wild flavor.

In various embodiments, the composition may comprise, or may consist essentially of, or may consist of casein at about 65.3-68.5%, 68.5-71.8%, 71.8-75.1%, 75.1-78.3%, 78.3-81.6%, 81.6-84.9%, 84.9-88.1%, 88.1-91.4%, 91.4-94.7%, or 94.7-97.9%, or about 81.6% by weight or volume. In various embodiments, the composition may comprise, or may consist essentially of, or may consist of sugar (e.g., glucose, fructose, galactose, maltose, lactose, and sucrose (for example, cane sugar and beet sugar)) at about 10.4-10.9%, 10.9-11.4%, 11.4-12.0%, 12.0-12.5%, 12.5-13.0%, 13.0-13.5%, 13.5-14.0%, 14.0-14.6%, 14.6-15.1%, or 15.1-15.6%, or about 13.0% by weight or volume. In various embodiments, the composition may comprise, or may consist essentially of, or may consist of vanilla flavor at about 1.40-1.47%, 1.47-1.54%, 1.54-1.61%, 1.61-1.68%, 1.68-1.75%, 1.75-1.82%, 1.82-1.89%, 1.89-1.96%, 1.96-2.04%, or 2.04-2.11%, or about 1.75% by weight or volume. In various embodiments, the composition may comprise, or may consist essentially of, or may consist of tart cherry extract at about 1.35-1.41%, 1.41-1.48%, 1.48-1.55%, 1.55-1.62%, 1.62-1.68%, 1.68-1.75%, 1.75-1.82%, 1.82-1.89%, 1.89-1.95%, or 1.95-2.02%, or about 1.68% by weight or volume. In various embodiments, the composition may comprise, or may consist essentially of, or may consist of sodium chloride at about 0.561-0.589%, 0.589-0.618%, 0.618-0.646%, 0.646-0.674%, 0.674-0.702%, 0.702-0.730%, 0.730-0.758%, 0.758-0.786%, 0.786-0.814%, or 0.814-0.842%, or about 0.702% by weight or volume. In various embodiments, the composition may comprise, or may consist essentially of, or may consist of BCAA at about 0.281-0.295%, 0.295-0.309%, 0.309-0.323%, 0.323-0.337%, 0.337-0.351%, 0.351-0.365%, 0.365-0.379%, 0.379-0.393%, 0.393-0.407%, or 0.407-0.421%, or about 0.351% by weight or volume. In various embodiments, the composition may comprise, or may consist essentially of, or may consist of L-glutamine at about 0.281-0.295%, 0.295-0.309%, 0.309-0.323%, 0.323-0.337%, 0.337-0.351%, 0.351-0.365%, 0.365-0.379%, 0.379-0.393%, 0.393-0.407%, or 0.407-0.421%, or about 0.351% by weight or volume. In various embodiments, the composition may comprise, or may consist essentially of, or may consist of stevia and/or stevia leaf extract at about 0.253-0.265%, 0.265-0.278%, 0.278-0.291%, 0.291-0.303%, 0.303-0.316%, 0.316-0.328%, 0.328-0.341%, 0.341-0.354%, 0.354-0.366%, or 0.366-0.379%, or about 0.316% by weight or volume. In various embodiments, the composition may comprise, or may consist essentially of, or may consist of xanthan gum at about 0.196-0.206%, 0.206-0.216%, 0.216-0.226%, 0.226-0.236%, 0.236-0.246%, 0.246-0.255%, 0.255-0.265%, 0.265-0.275%, 0.275-0.285%, or 0.285-0.295%, or about 0.246% by weight or volume. In some embodiments, the composition may consist of or may comprise or may consist essentially of one or more or all of these ingredients. In other embodiments, the composition may consist of or may comprise or may consist essentially of all of these ingredients.

In various embodiments, one serving of a composition described herein may consist of or may comprise or may consist essentially of one or more or all of: casein at about 65.3-68.5%, 68.5-71.8%, 71.8-75.1%, 75.1-78.3%, 78.3-81.6%, 81.6-84.9%, 84.9-88.1%, 88.1-91.4%, 91.4-94.7%, or 94.7-97.9%, or about 81.6% by weight or volume; sugar (e.g., glucose, fructose, galactose, maltose, lactose, and sucrose (for example, cane sugar and beet sugar)) at about 10.4-10.9%, 10.9-11.4%, 11.4-12.0%, 12.0-12.5%, 12.5-13.0%, 13.0-13.5%, 13.5-14.0%, 14.0-14.6%, 14.6-15.1%, or 15.1-15.6%, or about 13.0% by weight or volume; vanilla flavor at about 1.40-1.47%, 1.47-1.54%, 1.54-1.61%, 1.61-1.68%, 1.68-1.75%, 1.75-1.82%, 1.82-1.89%, 1.89-1.96%, 1.96-2.04%, or 2.04-2.11%, or about 1.75% by weight or volume; tart cherry extract at about 1.35-1.41%, 1.41-1.48%, 1.48-1.55%, 1.55-1.62%, 1.62-1.68%, 1.68-1.75%, 1.75-1.82%, 1.82-1.89%, 1.89-1.95%, or 1.95-2.02%, or about 1.68% by weight or volume; sodium chloride at about 0.561-0.589%, 0.589-0.618%, 0.618-0.646%, 0.646-0.674%, 0.674-0.702%, 0.702-0.730%, 0.730-0.758%, 0.758-0.786%, 0.786-0.814%, or 0.814-0.842%, or about 0.702% by weight or volume; BCAA at about 0.281-0.295%, 0.295-0.309%, 0.309-0.323%, 0.323-0.337%, 0.337-0.351%, 0.351-0.365%, 0.365-0.379%, 0.379-0.393%, 0.393-0.407%, or 0.407-0.421%, or about 0.351% by weight or volume; L-glutamine at about 0.281-0.295%, 0.295-0.309%, 0.309-0.323%, 0.323-0.337%, 0.337-0.351%, 0.351-0.365%, 0.365-0.379%, 0.379-0.393%, 0.393-0.407%, or 0.407-0.421%, or about 0.351% by weight or volume; stevia and/or stevia leaf extract at about 0.253-0.265%, 0.265-0.278%, 0.278-0.291%, 0.291-0.303%, 0.303-0.316%, 0.316-0.328%, 0.328-0.341%, 0.341-0.354%, 0.354-0.366%, or 0.366-0.379%, or about 0.316% by weight or volume; and xanthan gum at about 0.196-0.206%, 0.206-0.216%, 0.216-0.226%, 0.226-0.236%, 0.236-0.246%, 0.246-0.255%, 0.255-0.265%, 0.265-0.275%, 0.275-0.285%, or 0.285-0.295%, or about 0.246% by weight or volume. In some embodiments, the composition may consist of or may comprise or may consist essentially of one or more or all of these ingredients. In other embodiments, the composition may consist of or may comprise or may consist essentially of all of these ingredients.

In various embodiments, the composition may comprise, or may consist essentially of, or may consist of casein at about 64.9-68.2%, 68.2-71.4%, 71.4-74.7%, 74.7-77.9%, 77.9-81.2%, 81.2-84.4%, 84.4-87.7%, 87.7-90.9%, 90.9-94.2%, or 94.2-97.4%, or about 81.2% by weight or volume. In various embodiments, the composition may comprise, or may consist essentially of, or may consist of sugar (e.g., glucose, fructose, galactose, maltose, lactose, and sucrose (for example, cane sugar and beet sugar)) at about 11.1-11.6%, 11.6-12.2%, 12.2-12.8%, 12.8-13.3%, 13.3-13.9%, 13.9-14.4%, 14.4-15.0%, 15.0-15.5%, 15.5-16.1%, or 16.1-

16.6%, or about 13.9% by weight or volume. In various embodiments, the composition may comprise, or may consist essentially of, or may consist of vanilla flavor at about 1.43-1.50%, 1.50-1.57%, 1.57-1.64%, 1.64-1.71%, 1.71-1.79%, 1.79-1.86%, 1.86-1.93%, 1.93-2.00%, 2.00-2.07%, or 2.07-2.14%, or about 1.79% by weight or volume. In various embodiments, the composition may comprise, or may consist essentially of, or may consist of tart cherry extract at about 1.37-1.44%, 1.44-1.51%, 1.51-1.58%, 1.58-1.65%, 1.65-1.71%, 1.71-1.78%, 1.78-1.85%, 1.85-1.92%, 1.92-1.99%, or 1.99-2.06%, or about 1.71% by weight or volume. In various embodiments, the composition may comprise, or may consist essentially of, or may consist of sodium chloride at about 0.571-0.600%, 0.600-0.629%, 0.629-0.657%, 0.657-0.686%, 0.686-0.714%, 0.714-0.743%, 0.743-0.771%, 0.771-0.800%, 0.800-0.829%, or 0.829-0.857%, or about 0.714% by weight or volume. In various embodiments, the composition may comprise, or may consist essentially of, or may consist of stevia and/or stevia leaf extract at about 0.257-0.270%, 0.270-0.283%, 0.283-0.296%, 0.296-0.309%, 0.309-0.321%, 0.321-0.334%, 0.334-0.347%, 0.347-0.360%, 0.360-0.373%, or 0.373-0.386%, or about 0.321% by weight or volume. In various embodiments, the composition may comprise, or may consist essentially of, or may consist of xanthan gum at about 0.200-0.210%, 0.210-0.220%, 0.220-0.230%, 0.230-0.240%, 0.240-0.250%, 0.250-0.260%, 0.260-0.270%, 0.270-0.280%, 0.280-0.290%, or 0.290-0.300%, or about 0.250% by weight or volume. In some embodiments, the composition may consist of or may comprise or may consist essentially of one or more or all of these ingredients. In other embodiments, the composition may consist of or may comprise or may consist essentially of all of these ingredients.

In various embodiments, one serving of a composition described herein may consist of or may comprise or may consist essentially of one or more or all of: casein at about 64.9-68.2%, 68.2-71.4%, 71.4-74.7%, 74.7-77.9%, 77.9-81.2%, 81.2-84.4%, 84.4-87.7%, 87.7-90.9%, 90.9-94.2%, or 94.2-97.4%, or about 81.2% by weight or volume; sugar (e.g., glucose, fructose, galactose, maltose, lactose, and sucrose (for example, cane sugar and beet sugar)) at about 11.1-11.6%, 11.6-12.2%, 12.2-12.8%, 12.8-13.3%, 13.3-13.9%, 13.9-14.4%, 14.4-15.0%, 15.0-15.5%, 15.5-16.1%, or 16.1-16.6%, or about 13.9% by weight or volume; vanilla flavor at about 1.43-1.50%, 1.50-1.57%, 1.57-1.64%, 1.64-1.71%, 1.71-1.79%, 1.79-1.86%, 1.86-1.93%, 1.93-2.00%, 2.00-2.07%, or 2.07-2.14%, or about 1.79% by weight or volume; tart cherry extract at about 1.37-1.44%, 1.44-1.51%, 1.51-1.58%, 1.58-1.65%, 1.65-1.71%, 1.71-1.78%, 1.78-1.85%, 1.85-1.92%, 1.92-1.99%, or 1.99-2.06%, or about 1.71% by weight or volume; sodium chloride at about 0.571-0.600%, 0.600-0.629%, 0.629-0.657%, 0.657-0.686%, 0.686-0.714%, 0.714-0.743%, 0.743-0.771%, 0.771-0.800%, 0.800-0.829%, or 0.829-0.857%, or about 0.714% by weight or volume; stevia and/or stevia leaf extract at about 0.257-0.270%, 0.270-0.283%, 0.283-0.296%, 0.296-0.309%, 0.309-0.321%, 0.321-0.334%, 0.334-0.347%, 0.347-0.360%, 0.360-0.373%, or 0.373-0.386%, or about 0.321% by weight or volume; and xanthan gum at about 0.200-0.210%, 0.210-0.220%, 0.220-0.230%, 0.230-0.240%, 0.240-0.250%, 0.250-0.260%, 0.260-0.270%, 0.270-0.280%, 0.280-0.290%, or 0.290-0.300%, or about 0.250% by weight or volume. In some embodiments, the composition may consist of or may comprise or may consist essentially of one or more or all of these ingredients. In other embodiments, the composition may consist of or may comprise or may consist essentially of all of these ingredients.

In various embodiments, the composition may comprise, or may consist essentially of, or may consist of casein at about 18.6-19.5, 19.5-20.5, 20.5-21.4, 21.4-22.3, 22.3-23.3, 23.3-24.2, 24.2-25.1, 25.1-26.0, 26.0-27.0, or 27.0-27.9 g, or about 23.3 g. In various embodiments, the composition may comprise, or may consist essentially of, or may consist of sugar (e.g., glucose, fructose, galactose, maltose, lactose, and sucrose (for example, cane sugar and beet sugar)) at about 2.96-3.11, 3.11-3.26, 3.26-3.41, 3.41-3.56, 3.56-3.70, 3.70-3.85, 3.85-4.00, 4.00-4.15, 4.15-4.30, or 4.30-4.44 g, or about 3.70 g. In various embodiments, the composition may comprise, or may consist essentially of, or may consist of vanilla flavor at about 0.400-0.420, 0.420-0.440, 0.440-0.460, 0.460-0.480, 0.480-0.500, 0.500-0.520, 0.520-0.540, 0.540-0.560, 0.560-0.580, or 0.580-0.600 g, or about 0.500 g. In various embodiments, the composition may comprise, or may consist essentially of, or may consist of tart cherry extract at about 0.384-0.403, 0.403-0.422, 0.422-0.442, 0.442-0.461, 0.461-0.480, 0.480-0.499, 0.499-0.518, 0.518-0.538, 0.538-0.557, or 0.557-0.576 g, or about 0.480 g. In various embodiments, the composition may comprise, or may consist essentially of, or may consist of sodium chloride at about 0.160-0.168, 0.168-0.176, 0.176-0.184, 0.184-0.192, 0.192-0.200, 0.200-0.208, 0.208-0.216, 0.216-0.224, 0.224-0.232, or 0.232-0.240 g, or about 0.200 g. In various embodiments, the composition may comprise, or may consist essentially of, or may consist of BCAA at about 0.080-0.084, 0.084-0.088, 0.088-0.092, 0.092-0.096, 0.096-0.100, 0.100-0.104, 0.104-0.108, 0.108-0.112, 0.112-0.116, or 0.116-0.120 g, or about 0.100 g. In various embodiments, the composition may comprise, or may consist essentially of, or may consist of L-glutamine at about 0.080-0.084, 0.084-0.088, 0.088-0.092, 0.092-0.096, 0.096-0.100, 0.100-0.104, 0.104-0.108, 0.108-0.112, 0.112-0.116, or 0.116-0.120 g, or about 0.100 g. In various embodiments, the composition may comprise, or may consist essentially of, or may consist of stevia and/or stevia leaf extract at about 0.0720-0.0756, 0.0756-0.0792, 0.0792-0.0828, 0.0828-0.0864, 0.0864-0.0900, 0.0900-0.0936, 0.0936-0.0972, 0.0972-0.1008, 0.1008-0.1044, or 0.1044-0.1080 g, or about 0.0900 g. In various embodiments, the composition may comprise, or may consist essentially of, or may consist of xanthan gum at about 0.0560-0.0588, 0.0588-0.0616, 0.0616-0.0644, 0.0644-0.0672, 0.0672-0.0700, 0.0700-0.0728, 0.0728-0.0756, 0.0756-0.0784, 0.0784-0.0812, or 0.0812-0.0840 g, or about 0.0700 g. In some embodiments, the composition may consist of or may comprise or may consist essentially of one or more or all of these ingredients. In other embodiments, the composition may consist of or may comprise or may consist essentially of all of these ingredients.

In various embodiments, one serving of a composition described herein may consist of or may comprise or may consist essentially of one or more or all of: casein at about 18.6-19.5, 19.5-20.5, 20.5-21.4, 21.4-22.3, 22.3-23.3, 23.3-24.2, 24.2-25.1, 25.1-26.0, 26.0-27.0, or 27.0-27.9 g, or about 23.3 g; sugar (e.g., glucose, fructose, galactose, maltose, lactose, and sucrose (for example, cane sugar and beet sugar)) at about 2.96-3.11, 3.11-3.26, 3.26-3.41, 3.41-3.56, 3.56-3.70, 3.70-3.85, 3.85-4.00, 4.00-4.15, 4.15-4.30, or 4.30-4.44 g, or about 3.70 g; vanilla flavor at about 0.400-0.420, 0.420-0.440, 0.440-0.460, 0.460-0.480, 0.480-0.500, 0.500-0.520, 0.520-0.540, 0.540-0.560, 0.560-0.580, or 0.580-0.600 g, or about 0.500 g; tart cherry extract at about 0.384-0.403, 0.403-0.422, 0.422-0.442, 0.442-0.461, 0.461-0.480, 0.480-0.499, 0.499-0.518, 0.518-0.538, 0.538-0.557, or 0.557-0.576 g, or about 0.480 g; sodium chloride at about 0.160-0.168, 0.168-0.176, 0.176-0.184, 0.184-0.192, 0.192-0.200, 0.200-0.208, 0.208-0.216, 0.216-0.224, 0.224-0.232, or 0.232-0.240 g, or about 0.200 g; BCAA at about 0.080-0.084, 0.084-0.088, 0.088-0.092, 0.092-0.096, 0.096-0.100, 0.100-0.104, 0.104-0.108, 0.108-0.112, 0.112-0.116, or 0.116-0.120 g, or about 0.100 g; L-glutamine at about 0.080-0.084, 0.084-0.088, 0.088-0.092, 0.092-0.096, 0.096-0.100, 0.100-0.104, 0.104-0.108, 0.108-0.112, 0.112-0.116, or 0.116-0.120 g, or about 0.100 g; stevia and/or stevia leaf extract at about 0.0720-0.0756, 0.0756-0.0792, 0.0792-0.0828, 0.0828-0.0864, 0.0864-0.0900, 0.0900-0.0936, 0.0936-0.0972, 0.0972-0.1008, 0.1008-0.1044, or 0.1044-0.1080 g, or about 0.0900 g; and xanthan gum at about 0.0560-0.0588, 0.0588-0.0616, 0.0616-0.0644, 0.0644-0.0672, 0.0672-0.0700, 0.0700-0.0728, 0.0728-0.0756, 0.0756-0.0784, 0.0784-0.0812, or 0.0812-0.0840 g, or about 0.0700 g. In some embodiments, the composition may consist of or may comprise or may consist essentially of one or more or all of these ingredients. In other embodiments, the composition may consist of or may comprise or may consist essentially of all of these ingredients.

In various embodiments, the composition may comprise, or may consist essentially of, or may consist of casein at about 18.2-19.1, 19.1-20.0, 20.0-20.9, 20.9-21.8, 21.8-22.7, 22.7-23.6, 23.6-24.5, 24.5-25.5, 25.5-26.4, or 26.4-27.3 g, or about 22.7 g. In various embodiments, the composition may comprise, or may consist essentially of, or may consist of sugar (e.g., glucose, fructose, galactose, maltose, lactose, and sucrose (for example, cane sugar and beet sugar)) at about 3.11-3.26, 3.26-3.42, 3.42-3.57, 3.57-3.73, 3.73-3.88, 3.88-4.04, 4.04-4.19, 4.19-4.35, 4.35-4.50, or 4.50-4.66 g, or about 3.88 g. In various embodiments, the composition may comprise, or may consist essentially of, or may consist of vanilla flavor at about 0.400-0.420, 0.420-0.440, 0.440-0.460, 0.460-0.480, 0.480-0.500, 0.500-0.520, 0.520-0.540, 0.540-0.560, 0.560-0.580, or 0.580-0.600 g, or about 0.500 g. In various embodiments, the composition may comprise, or may consist essentially of, or may consist of tart cherry extract at about 0.384-0.403, 0.403-0.422, 0.422-0.442, 0.442-0.461, 0.461-0.480, 0.480-0.499, 0.499-0.518, 0.518-0.538, 0.538-0.557, or 0.557-0.576 g, or about 0.480 g. In various embodiments, the composition may comprise, or may consist essentially of, or may consist of sodium chloride at about 0.160-0.168, 0.168-0.176, 0.176-0.184, 0.184-0.192, 0.192-0.200, 0.200-0.208, 0.208-0.216, 0.216-0.224, 0.224-0.232, or 0.232-0.240 g, or about 0.200 g. In various embodiments, the composition may comprise, or may consist essentially of, or may consist of stevia and/or stevia leaf extract at about 0.0720-0.0756, 0.0756-0.0792, 0.0792-0.0828, 0.0828-0.0864, 0.0864-0.0900, 0.0900-0.0936, 0.0936-0.0972, 0.0972-0.1008, 0.1008-0.1044, or 0.1044-0.1080 g, or about 0.0900 g. In various embodiments, the composition may comprise, or may consist essentially of, or may consist of xanthan gum at about 0.0560-0.0588, 0.0588-0.0616, 0.0616-0.0644, 0.0644-0.0672, 0.0672-0.0700, 0.0700-0.0728, 0.0728-0.0756, 0.0756-0.0784, 0.0784-0.0812, or 0.0812-0.0840 g, or about 0.0700 g. In some embodiments, the composition may consist of or may comprise or may consist essentially of one or more or all of these ingredients. In other embodiments, the composition may consist of or may comprise or may consist essentially of all of these ingredients.

In various embodiments, one serving of a composition described herein may consist of or may comprise or may consist essentially of one or more or all of: casein at about 18.2-19.1, 19.1-20.0, 20.0-20.9, 20.9-21.8, 21.8-22.7, 22.7-23.6, 23.6-24.5, 24.5-25.5, 25.5-26.4, or 26.4-27.3 g, or about 22.7 g; sugar (e.g., glucose, fructose, galactose, maltose, lactose, and sucrose (for example, cane sugar and beet sugar)) at about 3.11-3.26, 3.26-3.42, 3.42-3.57, 3.57-3.73, 3.73-3.88, 3.88-4.04, 4.04-4.19, 4.19-4.35, 4.35-4.50, or 4.50-4.66 g, or about 3.88 g; vanilla flavor at about 0.400-0.420, 0.420-0.440, 0.440-0.460, 0.460-0.480, 0.480-0.500, 0.500-0.520, 0.520-0.540, 0.540-0.560, 0.560-0.580, or 0.580-0.600 g, or about 0.500 g; tart cherry extract at about 0.384-0.403, 0.403-0.422, 0.422-0.442, 0.442-0.461, 0.461-0.480, 0.480-0.499, 0.499-0.518, 0.518-0.538, 0.538-0.557, or 0.557-0.576 g, or about 0.480 g; sodium chloride at about 0.160-0.168, 0.168-0.176, 0.176-0.184, 0.184-0.192, 0.192-0.200, 0.200-0.208, 0.208-0.216, 0.216-0.224, 0.224-0.232, or 0.232-0.240 g, or about 0.200 g; stevia and/or stevia leaf extract at about 0.0720-0.0756, 0.0756-0.0792, 0.0792-0.0828, 0.0828-0.0864, 0.0864-0.0900, 0.0900-0.0936, 0.0936-0.0972, 0.0972-0.1008, 0.1008-0.1044, or 0.1044-0.1080 g, or about 0.0900 g; and xanthan gum at about 0.0560-0.0588, 0.0588-0.0616, 0.0616-0.0644, 0.0644-0.0672, 0.0672-0.0700, 0.0700-0.0728, 0.0728-0.0756, 0.0756-0.0784, 0.0784-0.0812, or 0.0812-0.0840 g, or about 0.0700 g. In some embodiments, the composition may consist of or may comprise or may consist essentially of one or more or all of these ingredients. In other embodiments, the composition may consist of or may comprise or may consist essentially of all of these ingredients.

In various embodiments, one serving of a composition as disclosed herein is administered to a subject. In various embodiments, one serving of a composition as disclosed herein comprise about 1-2, 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, 20-21, 21-22, 22-23, 23-24, 24-25, 25-26, 26-27, 27-28, 28-29, 29-30, 30-31, 31-32, 32-33, 33-34, 34-35, 35-36, 36-37, 37-38, 38-39, 39-40, 40-41, 41-42, 42-43, 43-44, 44-45, 45-46, 46-47, 47-48, 48-49, 49-50, 50-51, 51-52, 52-53, 53-54, 54-55, 55-56, 56-57, 57-58, 58-59, 59-60, 60-61, 61-62, 62-63, 63-64, 64-65, 65-66, 66-67, 67-68, 68-69, 69-70, 70-71, 71-72, 72-73, 73-74, 74-75, 75-76, 76-77, 77-78, 78-79, 79-80, 80-81, 81-82, 82-83, 83-84, 84-85, 85-86, 86-87, 87-88, 88-89, 89-90, 90-91, 91-92, 92-93, 93-94, 94-95, 95-96, 96-97, 97-98, 98-99, or 99-100 g of the composition. In one embodiment, one serving of a composition as disclosed herein comprises about 28.5 g of the composition. In another embodiment, one serving of a composition as disclosed herein comprises about 28 g of the composition.

In one embodiment, one spoon/level scoop of a composition described herein is one serving of the composition. In another embodiment, two spoons/level scoops of a composition described herein are one serving of the composition. In still another embodiment, three or more spoons/level scoops of a composition described herein are one serving of the composition. In various embodiments, one serving of a composition as disclosed herein is packaged as one packet, tube, vial, pouch, or bag. In various embodiments, two servings of a composition as disclosed herein are packaged as one packet, tube, vial, pouch, or bag. In various embodiments, three or more servings of a composition as disclosed herein are packaged as one packet, tube, vial, pouch, or bag.

In various embodiments, one serving of a composition as disclosed is combined with about 1-2, 2-3, 3-4, 4-5, 5-6, 6-7, 7-8, 8-9, 9-10, 10-11, 11-12, 12-13, 13-14, 14-15, or 15-16 fl. oz. water or any other suitable drinking liquid before being administrated to a subject.

In some embodiments, 1 serving of a composition described herein may be administered to a subject, for example, if the subject's body weight is below about 130, 140, 150, 160, 170, 180, or 190 pounds. In one embodiment, 1 serving of a composition described herein may be administered to a subject having a body weight below 160 pounds. In other embodiments, 2 servings of a composition described herein may be administered to a subject at one time, for example, if the subject's body weight is at or above about 130, 140, 150, 160, 170, 180, or 190 pounds. In one embodiment, 2 servings of a composition described herein may be administered to a subject having a body weight at or above 160 pounds.

In various embodiments, a subject consumes a composition described herein after exercise and before sleep. In some embodiments, a subject consumes a composition described herein immediately before sleep. In various embodiments, the subject consumes a composition described herein daily. As a non-limiting example, one serving of a composition described herein (for example, about 28.5 g of the composition powder) is mixed with about 8 fl. oz. water or any other suitable drinking liquid; let sit for about one minute; mixed again if necessary; and consumed by a subject. In one embodiment, the composition is consumed by a subject within a few minutes after preparation.

Various embodiments of the present invention provide a composition. The composition may consist of or may comprise or may consist essentially of one or more or all of: calcium, magnesium, sodium, potassium, tart cherry powder and a combination of micellar casein, branched chain amino acids (BCAAs), L-leucine, valine, isoleucine and L-glutamine. The composition may further comprise one or more or all of: sugar (e.g., glucose, fructose, galactose, maltose, lactose, and sucrose (for example, cane sugar and beet sugar)), vanilla flavor, stevia leaf extract and xanthan gum. In various embodiments, the calcium is in the form of calcium citrate, and/or calcium chloride, and/or any other suitable calcium salts or calcium sources. In various embodiments, the magnesium is in the form of magnesium citrate, and/or magnesium chloride, and/or any other suitable magnesium salts or magnesium sources. In various embodiments, the sodium is in the form of sodium citrate, and/or sodium chloride, and/or any other suitable sodium salts or sodium sources. In various embodiments, the potassium is in the form of potassium citrate, and/or chloride, and/or any other suitable potassium salts or potassium sources. In some embodiments, L-leucine, valine and isoleucine are at a ratio of 2:1:1. In exemplary embodiments, per serving, the composition may consist of or may comprise or may consist essentially of one or more or all of: about 420 mg calcium, about 15 mg magnesium, about 80 mg sodium, about 50 mg potassium, about 480 mg tart cherry powder, and about 23 g of the combination of micellar casein, branched chain amino acids (BCAAs), L-leucine, valine, isoleucine and L-glutamine. In exemplar embodiments, the composition may be used to improve exercise recovery. In some embodiments, the effective amount of the composition to improve exercise recovery is about 28.5 grams. In some embodiments, the effective amount of the composition is dissolved in water. For example, 28.5 grams of the composition may be dissolved in 8 ounces of water. In some embodiments, the composition is consumed before sleep, for example, within 1 hour before sleep.

In various embodiments, one, or more, or all of the ingredients of a composition described herein are dry blended together. In various embodiments, a composition described herein is provided in powder.

In various embodiments, a compositions described herein may be formulated in form of a solid, liquid or emulsion. For example, a composition described herein is provided in solid form as packets, tubes, vials, pouches or bags of powder that may be added to water or a beverage of a subject's choice for ease of consumption. In some embodiments, a composition described herein may be encapsulated, tableted or prepared in an emulsion or syrup for oral administration.

In various embodiments, a composition described herein may further include an excipient. As used herein, an "excipient" is a natural or synthetic substance formulated alongside the active ingredient of a composition or formula, included for the purpose of bulking-up the composition or formula. Thus, "excipient" is often referred to as "bulking agent", "filler", or "diluent". For a non-limiting example, one or more excipients may be added to a composition described herein and increase the composition's volume or size so that one serving of the composition fits into one spoon/level scoop. Also, an "excipient" may confer an enhancement on the active ingredients in the final dosage form, such as facilitating absorption or solubility of the active ingredients.

The compositions may be made following conventional techniques involving dry milling, mixing, and blending for powder forms; milling, mixing, granulation, and compressing for tablet forms; or milling, mixing and filling for hard gelatin capsule forms. The compositions of the invention may be sterilized by conventional sterilization techniques.

The compositions according to the invention may be delivered in an effective amount for improving exercise performance and/or recovery. The precise effective amount is that amount of the composition that will yield the most effective results in terms of efficacy of exercise performance and/or recovery in a given subject. This amount will vary depending upon a variety of factors, including but not limited to the characteristics of the formula's ingredients (including activity and bioavailability), the physiological condition of the subject (including age, sex, weight, metabolism, general physical condition, responsiveness to exercise nutrition systems), and the route of administration. One ordinarily skilled in the art will be able to determine an effective amount through routine experimentation, for instance, by monitoring a subject's response to administration of a composition described herein and adjusting the amounts of each accordingly.

A composition described herein may be administered in any number of routes. In accordance with the present invention, it is considered as "administering" that a subject consumes a composition as disclosed herein. Also in accordance with the present invention, "improving exercise performance and/or recovery" may mean that one subject's exercise performance and/or recovery is better with taking a composition as disclosed herein than without taking a composition as disclosed herein.

Methods of the Invention
Before Exercise

In various embodiments, the present invention provides a method for improving exercise performance and/or recovery in a subject. The method may consist of or may comprise or may consist essentially of: providing a composition described herein; and administering an effective amount of the composition to the subject, thereby improving exercise performance and/or recovery in a subject. In various embodiments, the composition is administered to the subject before an exercise.

In various embodiments, the present invention provides a method for controlling body weight and/or for promoting weight loss in a subject. The method may consist of or may comprise or may consist essentially of: providing a composition as disclosed herein; administering an effective amount of the composition to the subject, and subjecting the subject to an exercise after administering the effective amount of the composition, thereby controlling body weight and/or for promoting weight loss in the subject.

In various embodiments, the composition is administered before an exercise. In various embodiments, the composition is administered about 1-5, 5-10, 10-15, 15-20, 20-25, 25-30, 30-35, 35-40, 40-45, 45-50, 50-55, or 55-60 minutes, or 1-2, 2-3, 3-4, 4-5, 5-6, 6-7, 7-8, 8-9, 9-10, 10-11, or 11-12 hours before the exercise.

In various embodiments, the dosage of the composition is adjusted according to the subject's body weight. For example, if the subject's body weight is below about 130, 140, 150, 160, 170, 180, or 190 pounds, the subject may take 1 serving; and if the subject's body weight is at or above about 130, 140, 150, 160, 170, 180, or 190 pounds, the subject may take 2 servings. In certain embodiments, if the subject's body weight is below about 160 pounds, the subject may take 1 serving; and if the subject's body weight is at or above about 160 pounds, the subject may take 2 servings.

In various embodiments, the composition is administered at about 1-2, 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, 20-21, 21-22, 22-23, 23-24, 24-25, 25-26, 26-27, 27-28, 28-29, 29-30, 30-31, 31-32, 32-33, 33-34, 34-35, 35-36, 36-37, 37-38, 38-39, 39-40, 40-41, 41-42, 42-43, 43-44, 44-45, 45-46, 46-47, 47-48, 48-49, 49-50, 50-51, 51-52, 52-53, 53-54, 54-55, 55-56, 56-57, 57-58, 58-59, 59-60, 60-61, 61-62, 62-63, 63-64, 64-65, 65-66, 66-67, 67-68, 68-69, 69-70, 70-71, 71-72, 72-73, 73-74, 74-75, 75-76, 76-77, 77-78, 78-79, 79-80, 80-81, 81-82, 82-83, 83-84, 84-85, 85-86, 86-87, 87-88, 88-89, 89-90, 90-91, 91-92, 92-93, 93-94, 94-95, 95-96, 96-97, 97-98, 98-99, or 99-100 g per serving. In various embodiments, the composition is administered one, two, three, four or five times per day. In various embodiments, the composition is administered for about 1-3, 3-10, 10-20, 20-30, 30-40, 40-50, 50-60, 60-70, 70-80, 80-90 or 90-100 days, 1-6 or 6-12 months, or 1-5 years.

During Exercise

In various embodiments, the present invention provides a method for improving exercise performance and/or recovery in a subject. The method may consist of or may comprise or may consist essentially of: providing a composition described herein; and administering an effective amount of the composition to the subject, thereby improving exercise performance and/or recovery in a subject. In various embodiments, the composition is administered to the subject during an exercise.

In various embodiments, the present invention provides a method for controlling body weight and/or for promoting weight loss in a subject. The method may consist of or may comprise or may consist essentially of: providing a composition as disclosed herein; subjecting the subject to an exercise; and administering an effective amount of the composition to the subject during the exercise, thereby controlling body weight and/or for promoting weight loss in the subject.

In various embodiments, the composition is administered during an exercise In various embodiments, the exercise is about 1-5, 5-10, 10-15, 15-20, 20-25, 25-30, 30-35, 35-40, 40-45, 45-50, 50-55, or 55-60 minutes, or 1-2, 2-3, 3-4, 4-5, 5-6, 6-7, 7-8, 8-9, 9-10, 10-11, or 11-12 hours. In various embodiments, the dosage of the composition is adjusted according to the duration of the exercise.

In various embodiments, for every about 30 minutes, one serving of a composition as disclosed herein is administered to a subject. In some embodiments, for every about 20, 25, 30, 35, or 40 minutes, one serving of a composition as disclosed herein is administered to a subject.

In some embodiments, 1 serving of a composition described herein may be administered to a subject, for example, during an exercise of about 1-10, 10-20, 20-30, 30-40, or 40-50 minutes. In some embodiments, 2 servings of a composition described herein may be administered to a subject, for example, during an exercise of about 30-40, 40-50, 50-60, 60-70, or 70-80 minutes. In some embodiments, 3 servings of a composition described herein may be administered to a subject, for example, during an exercise of about 60-70, 70-80, 80-90, 90-100, or 100-110 minutes. In some embodiments, 4 servings of a composition described herein may be administered to a subject, for example, during an exercise of about 90-100, 100-110, 110-120, 120-130, or 130-140 minutes.

In one embodiment, 1 serving of a composition described herein may be administered to a subject during an exercise of about 1-30 minutes. In one embodiment, 2 servings of a composition described herein may be administered to a subject during an exercise of about 30-60 minutes. In one embodiment, 3 servings of a composition described herein may be administered to a subject during an exercise of about 60-90 minutes. In one embodiment, 4 servings of a composition described herein may be administered to a subject during an exercise of about 90-120 minutes.

In various embodiments, the number of servings administered to a subject during an exercise is calculated by dividing the exercise' duration (in the unit of minute) by 30 minutes. For non-limiting examples, 1 serving is for an exercise of about 15-45 minutes; 2 servings are for an exercise of about 45-75 minutes; 3 servings are for an exercise of about 75-105 minutes; and 4 servings are for an exercise of about 105-135 minutes.

In various embodiments, the composition is administered at about 1-2, 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, 20-21, 21-22, 22-23, 23-24, 24-25, 25-26, 26-27, 27-28, 28-29, 29-30, 30-31, 31-32, 32-33, 33-34, 34-35, 35-36, 36-37, 37-38, 38-39, 39-40, 40-41, 41-42, 42-43, 43-44, 44-45, 45-46, 46-47, 47-48, 48-49, 49-50, 50-51, 51-52, 52-53, 53-54, 54-55, 55-56, 56-57, 57-58, 58-59, 59-60, 60-61, 61-62, 62-63, 63-64, 64-65, 65-66, 66-67, 67-68, 68-69, 69-70, 70-71, 71-72, 72-73, 73-74, 74-75, 75-76, 76-77, 77-78, 78-79, 79-80, 80-81, 81-82, 82-83, 83-84, 84-85, 85-86, 86-87, 87-88, 88-89, 89-90, 90-91, 91-92, 92-93, 93-94, 94-95, 95-96, 96-97, 97-98, 98-99, or 99-100 g per serving. In various embodiments, the composition is administered one, two, three, four or five times per day. In various embodiments, the composition is administered for about 1-3, 3-10, 10-20, 20-30, 30-40, 40-50, 50-60, 60-70, 70-80, 80-90 or 90-100 days, 1-6 or 6-12 months, or 1-5 years.

After Exercise

In various embodiments, the present invention provides a method for improving exercise recovery in a subject. The method may consist of or may comprise or may consist essentially of: providing a composition described herein; and administering an effective amount of the composition to the subject, thereby improving exercise recovery in a subject. In various embodiments, the composition is administered to the subject after an exercise.

In various embodiments, the present invention provides a method for controlling body weight and/or for promoting lean muscle growth in a subject. The method may consist of or may comprise or may consist essentially of: providing a composition as disclosed herein; subjecting the subject to an exercise; and administering an effective amount of the composition to the subject after the exercise, thereby controlling body weight and/or for promoting lean muscle growth in the subject.

In various embodiments, the composition is administered after an exercise. In various embodiments, the composition is administered about 1-5, 5-10, 10-15, 15-20, 20-25, 25-30, 30-35, 35-40, 40-45, 45-50, 50-55, or 55-60 minutes, or 1-2, 2-3, 3-4, 4-5, 5-6, 6-7, 7-8, 8-9, 9-10, 10-11, or 11-12 hours after the exercise. In various embodiments, the composition is administered within about 1-5, 5-10, 10-15, 15-20, 20-25, 25-30, 30-35, 35-40, 40-45, 45-50, 50-55, or 55-60 minutes, or 1-2, 2-3, 3-4, 4-5, or 5-6 hours after the exercise.

In various embodiments, one serving is administered to the subject after one exercise. In some embodiments, the dosage of the composition is not adjusted according to the subject's body weight. In other embodiments, the dosage of the composition is adjusted according to the subject's body weight. For example, if the subject's body weight is below about 130, 140, 150, 160, 170, 180, or 190 pounds, the subject may take 1 serving; and if the subject's body weight is at or above about 130, 140, 150, 160, 170, 180, or 190 pounds, the subject may take 2 servings. In certain embodiments, if the subject's body weight is below about 160 pounds, the subject may take 1 serving; and if the subject's body weight is at or above about 160 pounds, the subject may take 2 servings.

In various embodiments, the composition is administered at about 1-2, 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, 20-21, 21-22, 22-23, 23-24, 24-25, 25-26, 26-27, 27-28, 28-29, 29-30, 30-31, 31-32, 32-33, 33-34, 34-35, 35-36, 36-37, 37-38, 38-39, 39-40, 40-41, 41-42, 42-43, 43-44, 44-45, 45-46, 46-47, 47-48, 48-49, 49-50, 50-51, 51-52, 52-53, 53-54, 54-55, 55-56, 56-57, 57-58, 58-59, 59-60, 60-61, 61-62, 62-63, 63-64, 64-65, 65-66, 66-67, 67-68, 68-69, 69-70, 70-71, 71-72, 72-73, 73-74, 74-75, 75-76, 76-77, 77-78, 78-79, 79-80, 80-81, 81-82, 82-83, 83-84, 84-85, 85-86, 86-87, 87-88, 88-89, 89-90, 90-91, 91-92, 92-93, 93-94, 94-95, 95-96, 96-97, 97-98, 98-99, or 99-100 g per serving. In various embodiments, the composition is administered one, two, three, four or five times per day. In various embodiments, the composition is administered for about 1-3, 3-10, 10-20, 20-30, 30-40, 40-50, 50-60, 60-70, 70-80, 80-90 or 90-100 days, 1-6 or 6-12 months, or 1-5 years.

Before Sleep

In various embodiments, the present invention provides a method for improving exercise recovery in a subject. The method may consist of or may comprise or may consist essentially of: providing a composition described herein; and administering an effective amount of the composition to the subject, thereby improving exercise recovery in a subject. In various embodiments, the composition is administered to the subject after an exercise and before sleep. In some embodiments, the composition is administered to the subject immediately before sleep.

In various embodiments, the present invention provides a method for controlling body weight and/or for promoting lean muscle growth in a subject. The method may consist of or may comprise or may consist essentially of: providing a composition as disclosed herein; subjecting the subject to an exercise; and administering an effective amount of the composition to the subject after the exercise and before sleep, thereby controlling body weight and/or for promoting lean muscle growth in the subject. In some embodiments, the composition is administered to the subject immediately before sleep.

In various embodiments, the composition is administered before sleep. In some embodiments, the composition is administered about 1-5, 5-10, 10-15, 15-20, 20-25, 25-30, 30-35, 35-40, 40-45, 45-50, 50-55, or 55-60 minutes before sleep. In other embodiments, the composition is administered about 1-2, 2-3, 3-4, 4-5, or 5-6 hours before sleep. In some embodiments, the composition is administered within about 1-5, 5-10, 10-15, 15-20, 20-25, 25-30, 30-35, 35-40, 40-45, 45-50, 50-55, or 55-60 minutes before sleep. In other embodiments, the composition is administered within about 1-2, 2-3, 3-4, 4-5, or 5-6 hours before sleep. In various embodiments, the composition is administered to the subject immediately before sleep.

In various embodiments, the composition is administered after an exercise. In various embodiments, the composition is administered about 1-5, 5-10, 10-15, 15-20, 20-25, 25-30, 30-35, 35-40, 40-45, 45-50, 50-55, or 55-60 minutes, or 1-2, 2-3, 3-4, 4-5, 5-6, 6-7, 7-8, 8-9, 9-10, 10-11, or 11-12 hours after the exercise. In various embodiments, the composition is administered within about 1-5, 5-10, 10-15, 15-20, 20-25, 25-30, 30-35, 35-40, 40-45, 45-50, 50-55, or 55-60 minutes, or 1-2, 2-3, 3-4, 4-5, 5-6, 6-7, 7-8, 8-9, 9-10, 10-11, or 11-12 hours after the exercise. In various embodiments, the composition is administered after an exercise and before sleep.

In various embodiments, one serving is administered to the subject. In some embodiments, the dosage of the composition is not adjusted according to the subject's body weight. In other embodiments, the dosage of the composition is adjusted according to the subject's body weight. For example, if the subject's body weight is below about 130, 140, 150, 160, 170, 180, or 190 pounds, the subject may take 1 serving; and if the subject's body weight is at or above about 130, 140, 150, 160, 170, 180, or 190 pounds, the subject may take 2 servings. In certain embodiments, if the subject's body weight is below about 160 pounds, the subject may take 1 serving; and if the subject's body weight is at or above about 160 pounds, the subject may take 2 servings.

In various embodiments, the composition is administered at about 1-2, 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, 20-21, 21-22, 22-23, 23-24, 24-25, 25-26, 26-27, 27-28, 28-29, 29-30, 30-31, 31-32, 32-33, 33-34, 34-35, 35-36, 36-37, 37-38, 38-39, 39-40, 40-41, 41-42, 42-43, 43-44, 44-45, 45-46, 46-47, 47-48, 48-49, 49-50, 50-51, 51-52, 52-53, 53-54, 54-55, 55-56, 56-57, 57-58, 58-59, 59-60, 60-61, 61-62, 62-63, 63-64, 64-65, 65-66, 66-67, 67-68, 68-69, 69-70, 70-71, 71-72, 72-73, 73-74, 74-75, 75-76, 76-77, 77-78, 78-79, 79-80, 80-81, 81-82, 82-83, 83-84, 84-85, 85-86, 86-87, 87-88, 88-89, 89-90, 90-91, 91-92, 92-93, 93-94, 94-95, 95-96, 96-97, 97-98, 98-99, or 99-100 g per serving. In various embodiments, the composition is administered one, two, three, four or five times per day. In various embodiments, the composition is administered for about 1-3, 3-10, 10-20, 20-30, 30-40, 40-50, 50-60, 60-70, 70-80, 80-90 or 90-100 days, 1-6 or 6-12 months, or 1-5 years.

In various embodiments, the subject is a human. In some embodiments, the subject has a normal body weight or a normal body mass index (BMI). In some embodiment, the subject is overweight or obese, or has a BMI over the normal range. In some embodiment, the subject is underweight, or has a BMI below the normal range. In accordance with the present invention, for adults 20 years and older: a BMI below 18.5 is considered underweight; a BMI of 18.5 to 24.9 is considered normal or healthy; a BMI of 25 to 29.9 is considered overweight; and a BMI of 30 or higher is considered obese.

In various embodiments, the composition is administered orally to the subject. In various embodiments, the composition is administered with water or a beverage to the subject.

Kits of the Invention

In various embodiments, the present invention provides a kit for improving exercise performance and/or recovery in a subject. The kit may consist of or may comprise or may consist essentially of: a composition described herein; and instructions for using the composition to improve exercise performance and/or recovery in the subject.

In various embodiments, the present invention provides a kit for controlling body weight and/or for promoting weight loss in a subject. The kit may consist of or may comprise or may consist essentially of: a composition as disclosed herein; and instructions for using the composition and an exercise to control body weight and/or promote weight loss in the subject.

In various embodiments, the present invention provides a kit for controlling body weight and/or for promoting lean muscle growth in a subject. The kit may consist of or may comprise or may consist essentially of: a composition as disclosed herein; and instructions for using the composition and an exercise to control body weight and/or promote lean muscle growth in the subject.

The kit is an assemblage of materials or components, including at least one of the inventive compositions. In one embodiment, the kit may consist of or may comprise or may consist essentially of a composition described herein. In various embodiments, the kit may contain one or more servings of the composition.

Instructions for use may be included in the kit. "Instructions for use" typically include a tangible expression describing the technique to be employed in using the components of the kit to affect a desired outcome. In various embodiments, the instructions comprise a program guide, exercise planner, manual, and/or recipe guide. Optionally, the kit also contains other useful components, such as, water, tea, beverages, fruits, vegetables, containers, applicators, measuring tools, or other useful materials as will be readily recognized by those of skill in the art.

The materials or components assembled in the kit can be provided to the practitioner stored in any convenient and suitable ways that preserve their operability and utility. The components are typically contained in suitable packaging material(s). As employed herein, the phrase "packaging material" refers to one or more physical structures used to house the contents of the kit, such as inventive compositions and the like. The packaging material is constructed by well-known methods, and may provide a sterile, contaminant-free environment. As used herein, the term "package" refers to a suitable solid matrix or material such as glass, plastic, paper, foil, and the like, capable of holding the individual kit components. Thus, for example, a package can be a paper packet to contain suitable quantities of a composition as described herein. The packaging material generally has an external label which indicates the contents and/or purpose of the kit and/or its components.

Many variations and alternative elements have been disclosed in embodiments of the present invention. Still further variations and alternate elements will be apparent to one of skill in the art. Among these variations, without limitation, are the selection of constituent modules for the inventive methods, compositions, kits, and systems, and the various conditions, diseases, and disorders that may be diagnosed, prognosed or treated therewith. Various embodiments of the invention can specifically include or exclude any of these variations or elements.

Various compositions of the present invention are described using the language "may consist of or may comprise or may consist essentially of one or more or all of certain ingredients." As used herein, the term "one or more or all" encompasses various embodiments where at least one, two, three, four, five, six, seven, eight, nine, . . . , until all those ingredients are included in a composition described herein. As a non-limiting example, a composition as described herein may consist of or may comprise or may consist essentially of one or more or all of: ingredient 1, ingredient 2, ingredient 3, ingredient 4, ingredient 5, ingredient 6, ingredient 7, ingredient 8, ingredient 9, . . . , and ingredient N (where N is the total number of possible ingredients). Accordingly, the composition may consist of or may comprise or may consist essentially of at least X of all these possible ingredients, wherein X is any integer between 1 and N (i.e., X=1, 2, 3, 4, 5, 6, 7, 8, 9, . . . , or N).

In some embodiments, the numbers expressing quantities of ingredients, properties such as concentration, reaction conditions, and so forth, used to describe and claim certain embodiments of the invention are to be understood as being modified in some instances by the term "about." As one non-limiting example, one of ordinary skill in the art would generally consider a value difference (increase or decrease) no more than 5% to be in the meaning of the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

EXAMPLES

The following examples are offered for illustrative purposes only, and are not intended to limit the scope of the present invention in any way.

Example 1: An Exemplar Pre-Exercise Product

One non-limiting example of the various compositions described herein is a pre-exercise product. This pre-exercise product is believed to improve intense exercise performance, improve energy and endurance, sharpen focus and reaction time, increase muscle carnosine concentration, increase muscle power output, delay exercise-induced muscle fatigue, and reduce exercise-induced muscle acid buildup.

This pre-exercise product has a unique combination of important performance enhancing (ergogenic) ingredients and ingredient forms. These important ingredients and ingredient forms are contained at specific levels in the pre-exercise product (Table 1 and Table 2), and possess synergistic mechanisms of action. While not wishing to be bound by any particular theory, FIG. 1A shows one mechanism of action of the product composition.

TABLE 1

Formula of the Exemplar Pre-Exercise Product

| Item Description | Item Weight | Unit | Percentage |
|---|---|---|---|
| Granuated Sugar (e.g., glucose, fructose, galactose, maltose, lactose, and sucrose (for example, cane sugar and beet sugar)) | 2.2755 | gram | 37.9250% |
| Citric Acid Granular | 1.0000 | gram | 16.6667% |
| Beta Alanine | 0.8000 | gram | 13.3333% |
| Quercetin Anhydrous | 0.5025 | gram | 8.3752% |
| Sodium Citrate | 0.2826 | gram | 4.7102% |
| Stevia | 0.2300 | gram | 3.8333% |
| Fruit flavor (e.g., lemonade, lemon, orange, mandarin orange, pineapple, pearl, apple, grape, cherry, citrus and other fruit flavors) | 0.2000 | gram | 3.3333% |
| Green tea extract | 0.2000 | gram | 3.3333% |
| Sodium Chloride | 0.1282 | gram | 2.1368% |
| Magnesium Citrate | 0.1250 | gram | 2.0833% |
| Silicon Dioxide | 0.1200 | gram | 2.0000% |
| Potassium Citrate | 0.1124 | gram | 1.8727% |
| Calcium Citrate Tetrahydrate | 0.0238 | gram | 0.3968% |
| TOTAL | 6.0000 | gram | 100.0000% |

TABLE 2

Supplement Facts of the Exemplar Pre-Exercise Product
Supplement Facts

Serving Size: 1 level scoop (6 g)
Serving per Container: 40

| | Amount per serving | % Daily Value * |
|---|---|---|
| Calories | 15 | |
| Total Carbohydrate | 4 g | 1% |
| Sugars | 2 g | ** |
| Calcium (as calcium citrate) | 5 mg | 1% |
| Magnesium (as magnesium citrate) | 20 mg | 5% |
| Sodium (as sodium citrate and sodium chloride) | 115 mg | 5% |
| Potassium (as potassium citrate) | 40 mg | 1% |
| PERFORMANCE/ANTI-MUSCLE FATIGUE BLEND | | |
| Beta-alanine | 800 mg | ** |
| Quercetin (*Uncaria elliptica*) anhydrous | 500 mg | ** |
| Green tea (*Carmellia sinensis*) extract (provides 100 mg of natural caffeine) | 200 mg | ** |

* Percent Daily Values are based on a 2,000 calorie diet
** % Daily Value (DV) not established.
Other Ingredients: Sugar (e.g., glucose, fructose, galactose, maltose, lactose, and sucrose (for example, cane sugar and beet sugar)), Citric Acid, Stevia (*Stevia rebaudiana*) leaf extract, Natural fruit flavor (e.g., lemonade, lemon, orange, mandarin orange, pineapple, pearl, apple, grape, cherry, citrus and other fruit flavors) type, Silica.

The pre-exercise product's dose may be customized or recommended according to a user's body weight. Before using the pre-exercise product, the product container is gently shaken to loosen compressed powder. One or two level scoops of the product powder are mixed with water until dissolved according to the recommended dosage below (Table 3), and the user drinks the beverage within 30 minutes before exercise. The pre-exercise product may be kept in a cool, dry place for storage.

TABLE 3

Recommended Dosages of the Exemplar Pre-Exercise Product
RECOMMENDED DOSAGE

| Body Weight (lbs) | <160 | ≥160 |
|---|---|---|
| Level Scoops | 1 | 2 |
| Water (oz) | 8 | 16 |

The specific levels of important ingredients and ingredient forms are validated by human clinical trials (on an individual basis), and shown to "improve exercise performance", "improve high-intensity or intense exercise performance", "reduce muscle lactic acid", "reduce muscle fatigue", "increase power output", "increase focus", and "increase reaction time". The combination of these important ingredients is to elicit an acute (single use) effect and a chronic (repeated use) effect to improve exercise performance and recovery. Described below are some non-limiting examples of various acute and chronic effects from some important ingredients and ingredient forms in the pre-exercise product.

β-Alanine

β-alanine at correct levels increases muscle carnosine overtime (>4 weeks supplementation) to buffer muscle and blood acid and/or lactic acid accumulation during exercise, reduce muscle fatigue, and increase power output.

Mechanism of β-Alanine

While not wishing to be bound by any particular theory, the mechanism for the ergogenic effects of β-alanine during exercise is believed to be related to the role of muscle carnosine in pH buffering as well as other mechanisms that explain a performance effect, including improved calcium handling and antioxidant effects. The effect of muscle carnosine on intracellular buffering has been demonstrated (Sale et al., 2010). A buffer has the ability to maintain a nearly constant pH in the face of acid or base challenges. During very intense exercise there are large increases in muscle and blood lactate and hydrogen ion ($H^+$) production, which can cause significant decreases in muscle pH. During very intense exercise for short durations, fatigue is caused, in part, by negative consequences resulting from the associated muscle acidosis. During these acidotic challenges there are several physiological mechanisms that can contribute to muscular and blood buffering capacity in attempts to maintain intramuscular pH, including a role for muscle carnosine. Carnosine is a potent intra-muscular buffer due to its nitrogen containing side imidazole ring, which can directly accept and buffer $H^+$ ions, and therefore slow the decline in pH during intense exercise.

Amount of β-Alanine

It has been shown that prolonged β-alanine supplementation (800 mg doses, ~1.6 to 6 g/day over 4 weeks) improves exercise performance (Harris et al., 2006). Since this discovery, every human study so far has demonstrated significant increases (>40%) in muscle carnosine during prolonged β-alanine supplementation (800 mg doses, 1.6-6.4 g/day for >4 weeks). It has also been shown that the absolute β-alanine/carnosine dose-response is solely dependent upon the total grams of β-alanine consumed and compounded overtime, and there is no impact on the daily β-alanine regime. Initial studies using β-alanine were at high single doses in excess of 800 mg (>10 mg/kg body mass) where subjects experienced symptoms of parathesia, described as a prickly sensation to the skin. In order to reduce the incidence of parathesia, 800 mg dose of β-alanine is recommended per serving (with a maximum 10 mg/kg body mass). Based on this established science, this is the dose strategy employed in the pre-exercise product by a dose per serving suggestion (i.e., body mass <160 lbs=1 scoop=800 mg; body mass ≥160 lbs=2 scoops=1600 mg). This approach was shown to be most successful in reducing the incidence and severity of any of discomfort in subjects. As such, this amount has been employed in numerous important future supplementation studies (Kendrick et al., 2008; Stout et al., 2007; van Thienen et al., 2009). The washout of β-alanine is also very slow (Stellingwerf et al., 2011). Therefore, practically speaking, once muscle carnosine content is increased, people can expect see potential performance benefits up to even 1 month post-supplementation due to the stability of muscle carnosine and slow washout profile.

Quercetin

Quercetin at correct levels improves and sustains exercise performance overtime (>1 week supplementation), and increases muscle mitochondrial biogenesis (or related energy production markers) to improve exercise performance and reduce exercise-induced muscle inflammation to improve exercise recovery.

Mechanism of Quercetin

Quercetin has been shown to improve exercise performance (Davis et al., 2010; Neiman et al., 2010). Quercetin may possess the ability to increase mitochondrial biogenesis to enhance energy metabolism and improve exercise performance, as shown in animal models (Davis et al., 2009) and trends in human clinical trials (Nieman et al., 2010). Quercetin also has relatively powerful anti-inflammatory activity given its ability to inhibit the proinflammatory pathway via Nf-KB (Harwood et al., 2007) that supports a role for quercetin to reduce muscle inflammation and improve exercise recovery. There are several clinical investigations that have examined the anti-inflammatory effects of quercetin following exercise. One study reported a reduction of certain blood inflammatory markers in quercetin-treated ultramarathon runners (Nieman et al., 2007). In another study by the same group, the influence of quercetin in combination with a flavanol from green tea was found to reduce markers of inflammation immediately after cycling (Nieman et al., 2009).

Amount of Quercetin

Studies investigating a role of quercetin in humans have employed a dosage protocol of 500 mg servings (500 mg, up to 1 g/day) to elicit a notable exercise performance benefit (Davis et al., 2010; Nieman et al., 2010). Based on established science, the pre-exercise product reflects this dose per serving (ie. BM<160 lbs=1 scoop=500 mg; BM≥160 lbs=2 scoops=1000 mg).

Green Tea and/or Natural Low-Dose Caffeine

Natural low-dose caffeine from green tea enhances energy, sharpens focus and reaction time, and improves exercise performance (>30 minutes supplementation) without side effects of higher doses such as jitters, nervousness, anxiety, the inability to sleep, or gastrointestinal distress. The use of low-dose caffeine from green tea is novel to improve exercise performance (studies have tested low-doses of anhydrous caffeine).

It is demonstrated that moderate to high caffeine doses (5-13 mg/kg body mass) consumed around 1 h before exercise, increased exercise performance in laboratory and field-simulations of sporting situations (Burke 2008; Conger et al. 2011; Graham et al. 1995; Spriet et al. 2000). These effects extend to recreationally trained and well-trained subjects, and are independent of gender, habitual caffeine use, withdrawal of caffeine, high carbohydrate diets prior to exercise, and consumption of carbohydrate during exercise.

Recent work suggests that caffeine is ergogenic in some short-term high intensity exercise and sport situations and also in team sport simulations. Lower caffeine doses (up to ~100 to 200 mg or 1.5-3 mg/kg body mass) taken before exercise also increase athletic performance and recent evidence also demonstrated a potent ergogenic effect of low doses of caffeine taken during prolonged exercise (Cox et al., 2002; Van Niewenhoven et al., 2000). Lower caffeine doses do not cause changes in the peripheral whole body responses to exercise, are associated with few if any side effects of higher doses, such as jitters, nervousness, the inability to sleep, or gastrointestinal distress (Cox et al., 2002; Van Niewenhoven et al., 2000; Talanian et al., 2008), and have no effect on hydration status and the ability to thermoregulate during exercise in normal conditions (Maughan, 2003).

Mechanism of Low-Dose Caffeine

Given the ergogenic effect of low caffeine doses, while not wishing to be bound by any particular theory, it is believed that the mechanisms to explain this effect lie in the central nervous system (Gliotonni et al., 2009; Kalmar et al., 2004). While all human caffeine performance studies have not separated the central effects of caffeine from the peripheral effects, there is direct evidence in preclinical studies that caffeine positively affects the central nervous system via adenosine receptor antagonism and ultimately enhancing brain neurotransmitter function (Kalmar et al., 2004).

Amount of Caffeine

Only low doses of caffeine (up to ~100 to 200 mg or 1.5-3 mg/kg body mass) are needed to improve exercise performance in most people. Consuming 100-200 mg caffeine may be the optimal dose for performance enhancement dependent on body mass. Based on this established science, this is the dose strategy employed in the pre-exercise product by a dose per serving suggestion (i.e., body mass <160 lbs=1 scoop=100 mg; body mass ≥160 lbs=2 scoops=200 mg).

While not wishing to be bound by any particular theory, it is believed that the pre-exercise product addresses various problems associated with exercise. Non-limiting examples include: (1) muscle acid buildup and ensuing muscle fatigue resulting in decline in exercise performance and power output—addressed by β-alanine; (2) reduced energy production by mitochondria and energy producing pathways (carbohydrate and fat oxidation and regulation)—addressed by quercetin; (3) increased muscle inflammation and damage and reduced adaptation to exercise and/or increase in muscle recovery time—addressed by quercetin; (4) reduced perception of energy and/or increased perception of fatigue—addressed by green tea and/or natural low-dose caffeine; (5) dehydration or reduced hydration status and compromised exercise performance—addressed by osmolality of final solution and the sugar, electrolyte, and water composition; and (6) jitters, nervousness, anxiety, the inability to sleep, or gastrointestinal distress from typical pre-exercise/energy drinks and powders—addressed by green tea and/or natural low-dose caffeine level.

The pre-exercise product improves intense exercise performance, improves energy and endurance, sharpens focus and reaction time, increases muscle carnosine concentration, increases muscle power output, delays exercise-induced muscle fatigue, reduces exercise-induced muscle acid buildup, reduces exercise-induced muscle inflammation, and improves hydration during exercise.

Example 2: Pre-Exercise Formula

Another non-limiting example of the various compositions described herein is a pre-exercise formula shown in Table 4. One serving of this pre-exercise formula may be combined with 8 oz. water for drinking. In addition to the listed ingredients, this pre-exercise formula may further include an excipient to increase its bulk size to, for example, 20 g per serving.

TABLE 4

Pre-Exercise Formula

| Item Description | % in formula | gram/serving |
|---|---|---|
| dextrose | 23.696% | 2.2511 |
| citric acid | 10.526% | 1.0000 |
| potassium citrate | 10.526% | 1.0000 |
| sodium citrate | 10.526% | 1.0000 |
| fruit flavor (e.g., lemonade, lemon, orange, mandarin orange, pineapple, pearl, apple, grape, cherry, citrus and other fruit flavors) | 2.105% | 0.2000 |
| beta alanine (compound solution) | 16.842% | 1.6000 |
| L-carnitine tartrate | 15.711% | 1.4925 |
| quercetin | 5.540% | 0.5263 |
| stevia | 2.421% | 0.2300 |
| green tea extract | 2.105% | 0.2000 |
| Total | 100% | 9.5000 |

Example 3: An Exemplar During-Exercise Product

One non-limiting example of the various compositions described herein is a during-exercise product. This during-exercise product is believed to support hydration during exercise, improve intense exercise performance, improve endurance, increase fluid absorption during exercise, replace electrolytes lost during exercise, and fuel working muscles.

This during-exercise product has a unique combination of important performance enhancing (ergogenic) ingredients and ingredient forms. These important ingredients and ingredient forms are contained at specific levels in the during-exercise product (Table 5 and Table 6), and possess synergistic mechanisms of action. While not wishing to be bound by any particular theory, FIG. 1B shows one mechanism of action of the product composition.

TABLE 5

Formula of the Exemplar During-Exercise Product

| Item Description | Item Weight | Unit | Percentage |
|---|---|---|---|
| Granulated Sugar (e.g., glucose, fructose, galactose, maltose, lactose, and sucrose (for example, cane sugar and beet sugar)) | 5.9664 | gram | 51.8817% |
| Dextrose | 3.0000 | gram | 26.0870% |
| Sodium citrate | 1.0000 | gram | 8.6957% |
| Citric Acid Granular | 0.5000 | gram | 4.3478% |
| Quercetin Anhydrous | 0.2513 | gram | 2.1849% |
| Magnesium Citrate | 0.2500 | gram | 2.1739% |
| Silicon Dioxide | 0.2300 | gram | 2.0000% |

TABLE 5-continued

Formula of the Exemplar During-Exercise Product

| Item Description | Item Weight | Unit | Percentage |
|---|---|---|---|
| Potassium Citrate | 0.2247 | gram | 1.9541% |
| Calcium Citrate Tetrahydrate | 0.0476 | gram | 0.4141% |
| Natural Mandarin Orange Flavor | 0.0200 | gram | 0.1739% |
| Stevia | 0.0100 | gram | 0.0870% |
| TOTAL | 11.5000 | | 100.0000% |

TABLE 6

Supplement Facts of the Exemplar During-Exercise Product
Supplement Facts

Serving Size: 1 level scoop (11.5 g)
Serving per Container: 40

| | Amount per serving | % Daily Value * |
|---|---|---|
| Calories | 40 | |
| Total Carbohydrate | 10 g | 3% |
| Sugars | 9 g | ** |
| HYDRATION BLEND | | |
| Calcium (as calcium citrate) | 10 mg | 1% |
| Magnesium (as magnesium citrate) | 40 mg | 10% |
| Sodium (as sodium citrate) | 230 mg | 10% |
| Potassium (as potassium citrate) | 80 mg | 2% |
| Quercetin (Uncaria elliptica) anhydrous | 250 mg | ** |

* Percent Daily Values are based on a 2,000 calorie diet
** % Daily Value (DV) not established.
Other Ingredients: Sugar (e.g., glucose, fructose, galactose, maltose, lactose, and sucrose (for example, cane sugar and beet sugar)), Dextrose, Citric Acid, Silica, Natural mandarin orange flavor (with other natural flavors), Stevia (Stevia rebaudiana) leaf extract.

The during-exercise product's dose may be customized or recommended according to duration of exercise. Before using the during-exercise product, the product container is gently shaken to loosen compressed powder. One, two, three or more level scoops of the product powder are mixed with water until dissolved according to the recommended dosage below (Table 7), and the user drinks the beverage during exercise. The during-exercise product may be kept in a cool, dry place for storage.

TABLE 7

Recommended Dosages of the Exemplar During-Exercise Product
RECOMMENDED DOSAGE

| Time (min) | 30 | 60 | 90 |
|---|---|---|---|
| Level Scoops | 1 | 2 | 3 |
| Water (oz) | 8 | 16 | 24 |

Described below are some non-limiting examples of various effects from some important ingredients and ingredient forms in the during-exercise product.

Hydration

The during-exercise product is prepared as a drink composition of specific solution osmolality to ensure rapid fluid absorption to the body and optimal fluid balance while replacing key electrolytes during exercise, which is matched to the average sweat loss rates in humans.

A water deficit is poorly tolerated; a deficit as little as 1% of body mass can impair exercise performance and tolerance; and both high-intensity and endurance exercises and sports are adversely affected (Cheuvront et al., 2003). Replacement of losses is, therefore, vital, but the relative insensitivity of the thirst mechanism can make this difficult to achieve in practice. Control of fluid balance in the body is intimately linked to electrolyte balance, and maintenance of hydration when sweat rates are high requires the replacement of electrolyte and fluid volume losses.

Effective Fluid Replacement

The major issues in fluid replacement for active individuals are optimizing hydration status before, during and/or after exercise, provision of fluid and fuel and possibly other nutrients during exercise, and rehydration and recovery after exercise. A diluted low sugar-electrolyte solution is the most effective way of replacing water loss when rapid rehydration is desired (Maughan, 1997). The rate of gastric emptying of solutions is slowed in proportion to the amount of carbohydrate content, and concentrated solutions will be unable to deliver water at high rates. Fluid absorption is driven by osmotic gradients and solvent drag resulting from active absorption of solute, especially glucose and sodium, which are transported by an ATP-dependent mechanism. Hypotonic (200-250 mosmol/kg) solutions containing glucose and sodium will maximize the rate of water absorption, but hypertonic solutions will cause a temporary secretion of water to the intestinal lumen, which can worsen any existing dehydration (Scedl et al., 1994). This during-exercise product contains a specific carbohydrate blend and electrolyte composition to ensure osmolality within the "hypotonic range" (e.g. 200-250 mosmol/kg). The ingestion of fluid during exercise can help reduce the fall in blood plasma volume that normally occurs; this in turn helps maintain cardiac output and increases skin blood blow, which helps promote heat loss and limits the rise in core temperature (Montain et al., 1995).

Drink Composition

Water alone during exercise does not effectively hydrate (Maughan et al., 1997; Maughan and Shirreffs, 1997). Through sweating, blood volume and electrolyte levels are reduced. To effectively hydrate during exercise, a solution with a specific composition of carbohydrate, electrolytes, and water is required to help maintain the body's water balance and replace important functional electrolytes (e.g., sodium) that are lost in sweat (Rowlands et al., 2011). Typical sports drinks can provide electrolytes but they can also be high in sugar (e.g. hypertonic>280 mosmol/kg) and artificial flavors and colors, which can cause gastrointestinal distress. This during-exercise product is different, because its specific composition of carbohydrates and electrolytes with a specific volume of water creates an optimal "hypotonic range" osmolality to maximize fluid absorption during exercise.

Here, the osmolality of a drink prepared from this during-exercise product is the ratio of the amount of solute (e.g. carbohydrates, electrolytes) dissolved in a given amount of water and should be ideally slightly lower than the osmolality of blood (slightly "hypotonic") in order allow rapid fluid absorption with minimal gastrointestinal discomfort. In one non-limiting example, the osmolality may be 213 mmoles/kg measured by vapor pressure osmometer (Model 5600) according to the vapor operating manual. This is the most important feature to allow for rapid and effective hydration and uniquely differentiates this during-exercise product from other sports drinks.

Quercetin

Quercetin at customizable levels, dependent on duration of exercise, improves exercise performance overtime (>1 week supplementation) and increases muscle mitochondrial biogenesis (or related energy production markers) to improve exercise performance and reduce exercise-induced muscle inflammation to improve exercise recovery Mechanism of Quercetin Quercetin has been shown to improve exercise performance (Davis et al., 2010; Neiman et al., 2010). Quercetin may possess the ability to increase mitochondrial biogenesis to enhance energy metabolism and improve exercise performance, as shown in animal models (Davis et al., 2009) and trends in human clinical trials (Nieman et al., 2010). Quercetin also has relatively powerful anti-inflammatory activity given its ability to inhibit the proinflammatory pathway via Nf-KB (Harwood et al., 2007) that supports a role for quercetin to reduce muscle inflammation and improve performance recovery. There are several clinical investigations that have examined the anti-inflammatory effects of quercetin following exercise. One study reported a reduction of certain blood inflammatory markers in quercetin-treated ultramarathon runners (Nieman et al., 2007). In another study by the same group, the influence of quercetin in combination with a flavanol from green tea was found to reduce markers of inflammation immediately after cycling (Nieman et al., 2009).

Amount of Quercetin

Studies investigating a role of quercetin in humans have employed a dosage protocol of 500 mg servings (500 mg, up to 1 g/day) to elicit a notable exercise performance benefit (Davis et al., 2010; Nieman et al., 2010). Based on established science, this during-exercise product reflects a 250 mg dose per serving which can be effective dependent on duration of exercise (e.g., 30 min exercise=1 scoop=250 mg; 1 h exercise=2 scoop=500 mg; and 1 h 30 min exercise=3 scoop=750 mg etc.).

While not wishing to be bound by any particular theory, it is believed that the during-exercise product addresses various problems associated with exercise. Non-limiting examples include: (1) drop in blood volume—addressed by fluid composition/osmolality, hypotonic solution; (2) changes in fluid balance—addressed by fluid composition/osmolality, hypotonic solution; (3) loss of electrolytes through sweat—addressed by electrolyte, sodium potassium, magnesium, calcium provision, which are matched to the average sweat loss rates; (4) reduced endurance and performance—addressed by effective hydration (i.e., fluid composition/osmolality, hypotonic solution); (5) reduced power output—addressed by effective hydration (i.e., fluid composition/osmolality, hypotonic solution); (6) dehydration and reduced hydration status through exercise and/or high ambient temperatures resulting in compromised exercise performance—addressed by fluid composition/osmolality, hypotonic solution; (7) gastrointestinal discomfort often associated with sports drinks—addressed by fluid composition/osmolality, hypotonic solution; and (8) glycogen depletion and impaired performance during and/or after exercise—addressed by carbohydrate provision.

The during-exercise product supports hydration during exercise, improves intense exercise performance, improves endurance, increases fluid absorption during exercise, replaces electrolytes lost during exercise, and fuel working muscles.

Example 4: During-Exercise Formula

Another non-limiting example of the various compositions described herein is a during-exercise formula shown in Table 8. One serving of this during-exercise formula may be combined with 8 oz. water for drinking. In addition to the listed ingredients, this during-exercise formula may further include an excipient to increase its bulk size to, for example, 20 g per serving.

TABLE 8

During-Exercise Formula

| Item Description | % in formula | gram/ serving |
|---|---|---|
| sugar (e.g., glucose, fructose, galactose, maltose, lactose, and sucrose (for example, cane sugar and beet sugar)) | 39.208% | 4.500 |
| dextrose | 41.822% | 4.800 |
| quercetin | 2.178% | 0.250 |
| sodium citrate | 8.713% | 1.000 |
| potassium citrate | 1.958% | 0.225 |
| magnesium citrate | 1.089% | 0.125 |
| calcium citrate | 0.415% | 0.048 |
| citric acid | 4.356% | 0.500 |
| stevia | 0.087% | 0.010 |
| mandarin orange | 0.174% | 0.020 |
| Total | 100.00% | 11.477 |

Example 5: An Exemplar Post-Exercise Product

One non-limiting example of the various compositions described herein is a post-exercise product. This post-exercise product is believed to speed muscle recovery, improve adaptation to exercise, promote lean muscle synthesis, reduce muscle breakdown, combat exercise-induced muscle soreness, support muscle glycogen recovery, and improve muscle strength recovery.

This post-exercise product has a unique combination of important recovery ingredients and ingredient forms. These important ingredients and ingredient forms are contained at specific levels in the post-exercise product (Table 9 and Table 10), possess synergistic mechanisms of action, and have important physiological and functional effects.

These important ingredients are scientifically shown to assist with muscle recovery and soreness from intense exercise sessions. Fast-, intermediate-, and slow-release proteins support muscle recovery and optimize training adaptations; an optimal ratio of branched-chain amino acids (BCAAs) helps stimulate muscle protein synthesis; a small amount carbohydrate supports muscle glycogen recovery; and a powerful ellagitannin-rich pomegranate extract helps promote speedy muscle strength recovery while reducing delayed onset muscle soreness (DOMS) from intense workouts. While not wishing to be bound by any particular theory, FIG. 1C shows one mechanism of action of the product composition.

TABLE 9

Formula of the Exemplar Post-Exercise Product

| Item Description | Item Weight | Unit | Percentage |
|---|---|---|---|
| Whey Protein Isolate | 13.0952 | gram | 36.8880% |
| Pea Protein | 7.5000 | gram | 21.1268% |
| Granulated Sugar (e.g., glucose, fructose, galactose, maltose, lactose, and sucrose (for example, cane sugar and beet sugar)) | 6.1722 | gram | 17.3865% |
| Micellar Casein | 3.4884 | gram | 9.8264% |
| Cocoa Powder, Alkalized | 2.5000 | gram | 7.0423% |
| Potassium Citrate | 0.6742 | gram | 1.8990% |
| POMx Pomegranate Ext. | 0.6500 | gram | 1.8310% |
| Sodium Chloride | 0.5000 | gram | 1.4085% |
| Natural Chocolate Flavor | 0.4000 | gram | 1.1268% |
| Xanthan Gum | 0.2000 | gram | 0.5634% |
| Stevia | 0.1200 | gram | 0.3380% |
| L-glutamine | 0.1000 | gram | 0.2817% |
| BCAA 2:1:1 | 0.1000 | gram | 0.2817% |
| TOTAL | 35.5000 | | 100.0000% |

TABLE 10

Supplement Facts of the Exemplar Post-Exercise Product
Supplement Facts

Serving Size: 1 level scoop (35.5 g)
Serving per Container: 20

| | Amount per serving | % Daily Value * |
|---|---|---|
| Calories | 130 | |
| Calories from Fat | 10 | |
| Total Fat | 1 g | 2% |
| Cholesterol | 5 mg | 2% |
| Total Carbohydrate | 10 g | 3% |
| Sugars | 6 g | ** |
| Protein | 20 g | 40% |
| Calcium | 140 mg | 14% |
| Magnesium | 40 mg | 10% |
| Sodium (as Sodium chloride) | 300 mg | 13% |
| Potassium (as Potassium citrate) | 420 mg | 12% |
| MUSCLE RECOVERY/ANTI-MUSCLE SORENESS BLEND | | |
| [Whey protein isolate, Pea protein isolate, Micellar casein, Branched-chain amino acids (BCAAs); L-leucine, Valine, Isoleucine (2:1:1), L-glutamine] | 23 g | ** |
| Pomegranate (*Punica granatum L.*) extract (POMx) | 650 mg | ** |

* Percent Daily Values are based on a 2,000 calorie diet
** % Daily Value (DV) not established.

Other Ingredients: Sugar (e.g., glucose, fructose, galactose, maltose, lactose, and sucrose (for example, cane sugar and beet sugar)), Cocoa Powder, Natural chocolate flavor (with other natural flavors), Xanthan gum, Stevia (*Stevia rebaudiana*) leaf extract.

Before using the post-exercise product, the product container is gently shaken to loosen compressed powder. One level scoop of the product powder is mixed with 8 oz. water until dissolved, and the user drinks the beverage within 30 minutes after exercise. The post-exercise product may be kept in a cool, dry place for storage.

The specific levels of important ingredients and ingredient forms are validated by human clinical trials (on an individual basis) shown to "improve recovery", "improve muscle recovery", "increase muscle growth", "reduce muscle breakdown", "reduce exercise-induced inflammation", "reduce muscle soreness", "increase strength recovery", and "improve adaptation to exercise". The combination of these important ingredients is to elicit an acute (single use) effect and a chronic (repeated use) effect to improve recovery. Described below are some non-limiting examples of various acute and chronic effects from some important ingredients and ingredient forms in the post-exercise product.

Protein Blend

Protein blend and leucine content at correct level increase muscle protein synthesis (MPS) and decrease muscle protein breakdown (MPB) via an amino acid-, insulin-dependent mechanism to improve muscle recovery, improve adaptation to exercise/training effects, increase muscle synthesis/mass, and reduce muscle breakdown.

Mechanism of Protein Blend

Dietary protein intake immediately after the cessation of resistance- or endurance-type exercise stimulates post-exercise muscle protein synthesis, inhibits protein breakdown and, as such allows net muscle accretion. Such dietary practice will allow a more adaptive response to each successive exercise bout, resulting in improved muscle reconditioning. It is clear that targeted timing for the ingestion of protein is very important. Protein should be consumed early during the post-exercise recovery phase (i.e., immediately to 2 hours post exercise). And, protein quality/amino acid profile is also very important in maximizing the accretion of muscle proteins. This is where portable protein sources, in the form of protein supplements, offer a practical alternative. Whey protein seems to be the most effective to increase muscle protein synthesis rates during acute post-exercise recovery, while other protein forms such as pea protein, and micellar casein provide slower rates of digestion and absorption to support sustained post-exercise recovery.

Amount of Protein and Leucine 20 g of high quality dietary protein should be provided immediately after cessation of exercise to allow post-exercise muscle protein synthesis rates to reach maximal levels above which protein synthesis is not further stimulated. Excess to this may result in increases in amino acid oxidation and urea synthesis may result as a consequence. Co-ingestion of (large) amounts of carbohydrate or additional leucine does not further increase muscle protein synthesis rate when ample protein is ingested. A healthy diet with smart timing of the ingestion of dietary protein after exercise will further improve the skeletal muscle adaptive response to continuous training. Based on established science, this post-exercise product reflects this dose per serving suggestion (i.e., 1 scoop=20 g of protein as fast (whey protein isolate), intermediate (pea protein isolate) and slow (micellar casein) protein).

The novel protein blend of fast—(whey protein isolate), intermediate—(pea protein), and slow-release (casein) proteins provides >1.8 g of leucine to maximally stimulate muscle protein synthesis (Glynn et al., 2010).

Pomegranate and Ellagitannins

Pomegranate at correct level reduces exercise-induced muscle inflammation, reduces muscle soreness, and improves strength recovery.

Nonsteroidal anti-inflammatory drugs (NSAIDS) like ibuprofen are commonly used by athletes of all levels in an effort to alleviate pain, muscle soreness, stiffness, and overall inflammation that occurs as a result of intense exercise or competition (Ciocca, 2005). NSAIDS can have serious side effects including cardiovascular complications and gastrointestinal distress. Phytonutrients with distinct recovery can be potent recovery aids following physical performance without documented side effects of NSAIDs.

Recent investigations involving the ellagitannins (a large phytonutrient found primarily in pomegranates) and physical performance recovery after stressful exercise have begun to emerge. Ellagitannin research has primarily focused on reducing inflammation (Gonzalez-Gallego et al., 2010). Trombold et al. (2010) examined the effects of 9 days of 650 mg doses of pomegranate extract (POMx) treatment in muscle damage and strength recovery following intense resistance training. The results indicated that the pomegranate extract treatment group produced more force in the exercised muscle at 48-72 hours after training. A follow up study confirmed that pomegranate supplementation reduced muscle weakness and soreness and implicated an ergogenic effect of pomegranate in resistance trained individuals after eccentric exercise (Trombold et al., 2011). Based on this established science, this post-exercise product provides this dose per serving suggestion (i.e., 1 scoop=650 mg of ellagitannin-rich pomegranate extract, POMx).

While not wishing to be bound by any particular theory, it is believed that the post-exercise product addresses various problems associated with exercise. Non-limiting examples include: (1) access and portability to effective level and form of protein to improve rapid and sustained recovery during post-exercise window—addressed by protein blend, >1.8 g leucine; (2) balance of muscle protein synthesis (MPS) and muscle protein breakdown (MPB) directed towards net MPS enabling muscle recovery/synthesis vs. net MPB resulting in limited adaptations to exercise/ or promoting muscle breakdown—addressed by protein blend, >1.8 g leucine; (3) muscle inflammation from exercise and ensuing muscle soreness/delayed onset muscle soreness (DOMS) resulting in decline in exercise performance, strength recovery, and overall muscle recovery, and related psychological discomfort—addressed by pomegranate, ellagitannins; and (4) alternative measure to reduce muscle soreness without the side effects of NSAIDS provided—addressed by pomegranate, ellagitannins.

The post-exercise product speeds muscle recovery, improves adaptation to exercise, promotes lean muscle synthesis, reduces muscle breakdown, combats exercise-induced muscle soreness, supports muscle glycogen recovery, and improves muscle strength recovery. Also, the post-exercise product contains fast, intermediate, and slow release proteins.

Example 6: Post-Exercise Formula

Another non-limiting example of the various compositions described herein is a post-exercise formula shown in Table 11. One serving of this post-exercise formula may be combined with 8 oz. water for drinking. In addition to the listed ingredients, this post-exercise formula may further include an excipient to increase its bulk size.

TABLE 11

Post-Exercise Formula

| Item Description | % in formula | gram/ serving |
|---|---|---|
| Pea Protein | 18.293% | 7.500 |
| Whey Protein Isolate | 40.651% | 16.667 |
| Casein | 8.315% | 3.409 |
| Sugar (e.g., glucose, fructose, galactose, maltose, lactose, and sucrose (for example, cane sugar and beet sugar)) | 14.595% | 5.984 |
| Cocoa powder | 10.976% | 4.500 |
| L-glutamine FCC | 0.244% | 0.100 |
| BCAA 2:1:1 | 0.244% | 0.100 |
| Xanthan gum | 0.244% | 0.100 |
| Potassium Citrate | 2.439% | 1.000 |
| Sodium Chloride | 1.220% | 0.500 |
| Natural Chocolate Flavor | 0.976% | 0.400 |
| Stevia | 0.220% | 0.090 |
| PomX Pomegranate (75% polyphenols) | 1.585% | 0.650 |
| Total | 100% | 41.000 |

Example 7: An Exemplar Nighttime Product

One non-limiting example of the various compositions described herein is a nighttime product for improving post-exercise overnight recovery. This nighttime product is believed to support overnight muscle recovery or improve overnight adaptation to exercise, improve overnight adaptation to exercise, promote lean muscle synthesis, reduce muscle breakdown, combat exercise-induced muscle soreness, and reduce exercise-induced oxidative stress.

This nighttime product has a unique combination of important recovery ingredients and ingredient forms. These important ingredients and ingredient forms are contained at specific levels in the nighttime product (Table 12 and Table 13), possess synergistic mechanisms of action, and have important physiological and functional effects.

Figure 1D:
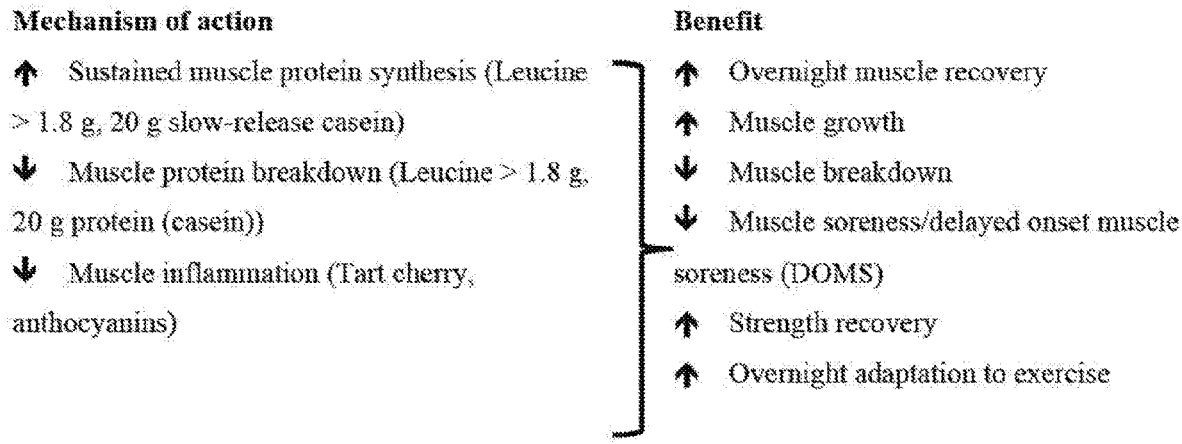

Sleep is crucial to recovery. This nighttime product is formulated with important ingredients scientifically shown to assist with overnight muscle recovery and soreness from intense workout days. Slow-release micellar casein protein supports overnight muscle recovery and repair while combating breakdown; an optimal ratio of branched-chain amino acids (BCAAs) helps stimulate muscle protein synthesis overnight; and a powerful anthocyanin-rich tart cherry powder helps reduce exercise-induced oxidative stress and delayed onset muscle soreness (DOMS) from intense workout days. While not wishing to be bound by any particular theory, FIG. 1D shows one mechanism of action of the product composition.

TABLE 12

Formula of the Exemplar Nighttime Product

| Item Description | Item Weight | Unit | Percentage |
|---|---|---|---|
| Micellar Casein | 23.2560 | gram | 81.6000% |
| Granulated Sugar (e.g., glucose, fructose, galactose, maltose, lactose, and sucrose (for example, cane sugar and beet sugar)) | 3.7040 | gram | 12.9965% |
| Natural Vanilla Flavor | 0.5000 | gram | 1.7544% |
| Tart Cherry Extract | 0.4800 | gram | 1.6842% |
| Sodium Chloride | 0.2000 | gram | 0.7018% |
| BCAA 2:1:1 | 0.1000 | gram | 0.3509% |
| L-glutamine | 0.1000 | gram | 0.3509% |
| Stevia | 0.0900 | gram | 0.3158% |
| Xanthan Gum | 0.0700 | gram | 0.2456% |
| TOTAL | 28.5000 | | 100.0000% |

TABLE 13

Supplement Facts of the Exemplar Nighttime Product
Supplement Facts

Serving Size: 1 level scoop (28.5 g)
Serving per Container : 20

| | Amount per serving | % Daily Value * |
|---|---|---|
| Calories | 100 | |
| Cholesterol | 10 mg | 3% |
| Total Carbohydrate | 6 g | 2% |
| Sugars | 5 g | ** |
| Protein | 20 g | 40% |
| Calcium | 420 mg | 42% |
| Magnesium | 15 mg | 4% |
| Sodium (as sodium chloride) | 80 mg | 3% |
| Potassium | 50 mg | 1% |
| OVERNIGHT MUSCLE RECOVERY/ ANTI-MUSCLE SORENESS BLEND | | |
| [(Micellar casein, Branched chain amino acids (BCAAs); L-leucine, Valine, Isoleucine (2:1:1), L-glutamine)] | 23 g | ** |
| Tart cherry (*Prunus cerasus*) powder | 480 mg | ** |

\* Percent Daily Values are based on a 2,000 calorie diet
\*\*% Daily Value (DV) not established
Other Ingredients: Sugar (e.g., glucose, fructose, galactose, maltose, lactose, and sucrose (for example, cane sugar and beet sugar)), Natural vanilla flavor (with other natural flavors), Stevia (*Stevia rebaudiana*) leaf extract, Xanthan gum.

Before using the nighttime product, the product container is gently shaken to loosen compressed powder. One level scoop of the product powder is mixed with 8 oz. water until dissolved, and the user drinks the beverage within 1 hour of going to sleep. The nighttime product may be kept in a cool, dry place for storage.

The specific levels of important ingredients and ingredient forms are validated by human clinical trials (on an individual basis) shown to "improve overnight recovery", "improve overnight muscle recovery", "increase muscle growth", "reduce muscle breakdown", "reduce exercise-induced inflammation", "reduce muscle soreness", "increase strength recovery", and "improve overnight adaptation to exercise". The combination of these important ingredients is to elicit an acute (single use) effect and a chronic (repeated use) effect to improve overnight recovery. Described below are some non-limiting examples of various acute and chronic effects from some important ingredients and ingredient forms in the nighttime product.

Protein Blend

Slow-release casein at correct level increases sustained muscle protein synthesis (MPS) and decrease muscle protein breakdown (MPB) via an amino acid-, insulin-dependent mechanism to improve overnight muscle recovery, improve overnight adaptation to exercise/training effects, increase muscle synthesis/mass, and reduce muscle breakdown.

Mechanism of Slow-Release Protein

One novel area of research involves whether protein administration following exercise performed in the evening has an impact on subsequent overnight recovery. Post-exercise muscle reconditioning during overnight sleep is a novel field of research. There is emerging evidence on the impact of exercise on muscle protein synthesis during subsequent overnight recovery (Beelen et al., 2008). It was shown that muscle protein synthesis was increased during the first few hours of post-exercise recovery when protein was ingested. However, muscle protein synthesis during subsequent sleep was unexpectedly low, with values being close to basal. Since this finding, the impact of protein ingestion immediately before sleep on digestion and absorption kinetics and protein metabolism during overnight recovery after exercise was investigated (Res et al., 2012). This recent research was the first to show that 20 g protein ingested in the form of casein immediately before sleep was effectively digested and absorbed, thereby stimulating muscle protein synthesis and improving whole-body protein balance during post-exercise overnight recovery. Furthermore, the same group recently presented at the European College of Sport Science Congress that protein (in the form of casein) ingestion prior to sleep represents an effective dietary strategy to augment muscle mass gain during prolonged resistance type exercise training in healthy people (Snijders et al., 2014).

Amount of Protein (Casein)

The appropriate provision of 20 g of high quality (casein) protein was an effective contributor to improved overnight muscle recovery (Res et al., 2012) highlighting the potential advantage to selection of specific protein characteristics (i.e., slow-release casein protein) and targeted timing of ingestion (i.e., before sleep). Based on this research, this nighttime product reflects a similar dose per serving suggestion (i.e., 1 scoop=20 g of protein as slow (micellar casein) protein).

Tart Cherry and Anthocyanins

Tart cherry at correct level reduces exercise-induced inflammation and reduces muscle soreness.

Nonsteroidal anti-inflammatory drugs (NSAIDS) like ibuprofen are commonly used by athletes of all levels in an effort to alleviate pain, muscle soreness, stiffness, and overall inflammation that occurs as a result of intense exercise or competition (Ciocca, 2005). NSAIDS can have serious side effects including cardiovascular complications and gastrointestinal distress. Phytonutrients with distinct recovery can be potent recovery aids following physical performance without documented side effects of NSAIDs.

Like pomegranate ellagitannins, tart cherry anthocyanin research has focused on reducing inflammation. Similar results of improvement of recovery have been seen with anthocyanin-rich cherry juice (Connolly et al., 2006; Howatson et al., 2010). Connolly et al. (2006) reported that subjects who supplemented with cherry juice for 8-days prior to a muscle-damaging exercise regimen had significantly less strength loss than the placebo up to 96 hours after exercise. Similarly, Howatson et al. (2010) found benefits to tart cherry juice in marathon runners. Since these studies, a novel anthocyanin-rich tart cherry powder has been investigated for recovery properties in both resistance and endurance based exercise. Levers et al. (2014) and Galvan et al. (2014) presented at the International Society of Sports Nutrition that a 480 mg dose of the tart cherry powder resulted in exercise recovery benefits and reduction of muscle soreness after intense modes of exercise. Based on this research, this nighttime product reflects a similar dose per serving suggestion (i.e., 1 scoop=480 mg of anthocyanin-rich tart cherry powder).

While not wishing to be bound by any particular theory, it is believed that the nighttime product addresses various problems associated with exercise. Non-limiting examples include: (1) access and portability to effective level and form of protein to improve post-exercise overnight recovery—addressed by slow-release casein protein, >1.8 g leucine; (2) balance of muscle protein synthesis (MPS) and muscle protein breakdown (MPB) directed towards net MPS enabling muscle recovery/synthesis vs. net MPB resulting in limited adaptations to exercise/or promoting muscle breakdown—addressed by slow-release casein protein, >1.8 g leucine; (3) muscle inflammation from exercise and ensuing muscle soreness/delayed onset muscle soreness (DOMS) resulting in decline in exercise performance, strength recovery, and overall muscle recovery, and related psychological discomfort—addressed by tart cherry, anthocyanins; and (4) alternative measure to reduce muscle soreness without the side effects of NSAIDS provided—addressed by tart cherry, anthocyanins.

The nighttime product supports overnight muscle recovery, improves overnight adaptation to exercise, promotes lean muscle synthesis, reduces muscle breakdown, reduces exercise-induced inflammation, combats exercise-induced muscle soreness, and reduces exercise-induced oxidative stress. Also, the nighttime product contains slow release micellar casein protein.

Example 8: Nighttime Formula

Another non-limiting example of the various compositions described herein is a post-exercise formula shown in Table 14. One serving of this post-exercise formula may be combined with 8 oz. water for drinking. In addition to the listed ingredients, this post-exercise formula may further include an excipient to increase its bulk size.

TABLE 14

Nighttime Formula

| Item Description | % in formula | gram/serving |
|---|---|---|
| Casein | 81.168% | 22.727 |
| Sugar (e.g., glucose, fructose, galactose, maltose, lactose, and sucrose (for example, cane sugar and beet sugar)) | 13.868% | 3.883 |
| Natural Vanilla Flavor | 1.786% | 0.500 |
| Xanthan gum | 0.250% | 0.070 |
| Sodium Chloride | 0.714% | 0.200 |
| Stevia | 0.321% | 0.090 |
| Tart Cherry | 1.714% | 0.480 |
| curcumin C3 complex | 0.179% | 0.050 |
| TOTAL | 100.00% | 28.000 |

Example 9: Test Group Survey Data and Analysis

Survey feedback and/or changes in weight loss and/or body composition (e.g., body fat) are included in a test group survey data and analysis (FIGS. 2-33).

Background and Objectives

Preliminary results through a family and friends test group are obtained, where participants would follow one of three Beachbody fitness programs (Body Beast, 21 Day Fix Extreme, or INSANITY) for a month, while taking the products described herein. A total of 30 test group participants were recruited and required to complete a baseline survey, which captured their initial perceptions before they started the test group, a recurring survey twice per week to record their perceptions throughout the test group, and a claims survey to help develop claims for the products described herein. This survey analysis trends the aggregate of all survey responses from the baseline survey, if applicable, the recurring surveys, and the claims test survey. In these results, all trends are directional by nature.

Key Summary of Findings

Overall, test group participants felt an improvement on all key attributes as the test group progressed. Strong and gradual increases are noted in Table 15 below.

TABLE 15

| Key Summary of Findings | |
|---|---|
| Pre-Exercise Results | |
| Strong increases | Energy Level |
| | Hydrating |
| | Strength |
| Gradual increases | Motivation |
| During-Exercise Results | |
| Strong increases | Workout Performance |
| | Energy Level |

TABLE 15-continued

Key Summary of Findings

| | |
|---|---|
| Gradual increases | Pushing self |
| | Hydration |
| | Focus |
| | Cramping Reduction |
| Post-Exercise Results | |
| Strong increases | Replenishment |
| | Energy Level |
| | Recovery |
| | Muscle Definition |
| Gradual increases | Feeling |
| Nighttime Results | |
| Strong increases | Replenishment |
| | Muscle Soreness Reduction |
| | Muscle Stiffness Reduction |
| Gradual increases | Decreased Hunger |
| Day After Results | |
| Strong increases | Feeling |
| | Replenishment |
| | Energy Level |
| | Refreshed |
| | Muscle Soreness Reduction |
| | Muscle Stiffness Reduction |
| Gradual increases | Sleep Quality |
| | Decreased Hunger |
| | Muscle Definition |

Claim Survey Among the Respondents (n=27)

100% users agree that the products helped them perform better during intense exercise/workouts;

100% users agree that the products helped them last longer during intense exercise/workouts;

100% users agree that the pre-workout products helped them increase their energy level for intense exercise/workouts;

100% users agree that the products helped them delay muscle fatigue during intense exercise/workouts;

100% users agree that the products helped improve their stamina during intense exercise/workouts;

100% users agree that the products helped them recover faster from intense exercise/workouts;

100% users agree that the products helped them recover their strength faster after their intense exercise/workouts;

100% users agree that the products helped them get leaner faster;

100% users agree that the products helped their body adapt to intense exercise/workouts;

100% users agree that the nighttime products helped with overnight muscle recovery after intense exercise/workout days;

100% users agree that the products helped them achieve their fitness goals faster and easier;

100% users agree that the products were easy to use;

96% users agree that the products helped them increase strength to power through their intense exercise/workouts;

96% users agree that the products helped improve their muscle recovery from intense exercise so they could hit their next workouts harder the next day;

96% users agree that after intense exercise/workouts, the nighttime products helped them wake up feeling refreshed and ready to take on their next workout;

96% users agree that the during-exercise products taste great;

96% users agree that the post-exercise products taste great;

93% users agree that the during-exercise products helped them keep hydrated during intense exercise/workouts;

93% users agree that the products helped reduce muscle soreness after intense exercise/workouts;

93% users agree that the products helped reduce the onset of muscle soreness (DOMS) during intense exercise/workouts;

93% users agree that the nighttime products helped them feel less hungry before going to bed;

93% users agree that the products taste great;

93% users agree that the products are better than other sports/performance nutrition products on the market;

89% users agree that the products helped them improve focus during intense exercise/workouts;

89% users agree that the products helped them achieve their weight loss goals faster;

85% users agree that the products helped them improve reaction time during intense exercise/workouts;

85% users agree that the nighttime products helped them sleep better after intense exercise/workout days;

85% users agree that the pre-exercise products taste great;

81% users agree that the products helped reduce muscle burn during intense exercise/workouts;

81% users agree that the products helped reduce muscle cramps during intense exercise/workouts;

74% users agree that the nighttime products helped them feel less hungry upon waking up in the morning; and 67% users agree that the nighttime products taste great.

Survey Questions and Answers (1) Pre-Exercise

Q1. What time of day did you work out yesterday? Most of the test group participants work out in the morning (FIG. 2).

Figure 3:
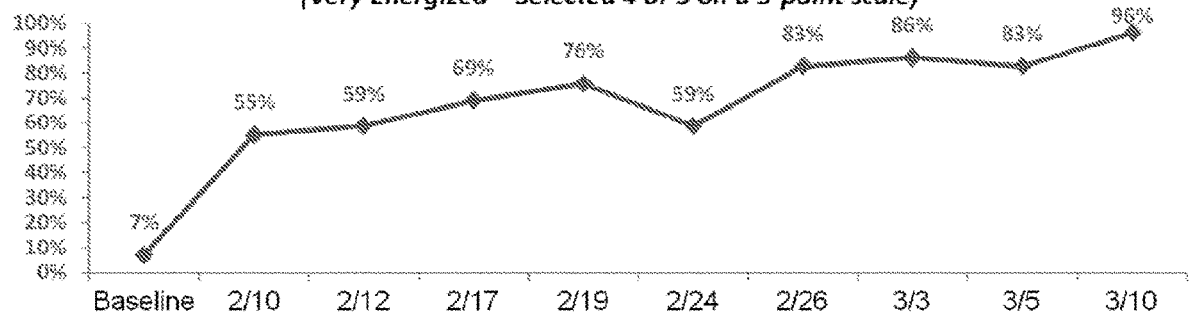

Q2a. Before your workout, how energized (or tired) did you feel? Test group participants felt more energized before they started working out as the test group progressed (FIG. 3).

Figure 4:
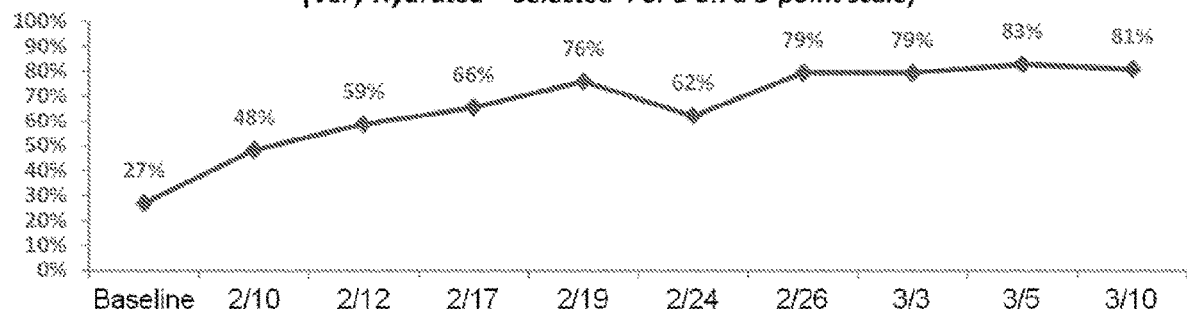

Q2b. Before your workout, how hydrated (or thirsty) did you feel? Test group participants felt more hydrated before they started working out as the test group progressed (FIG. 4).

Figure 5:
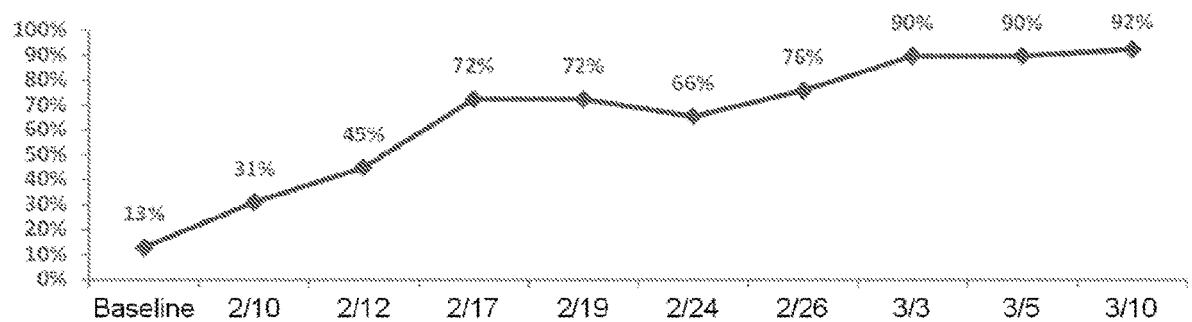

Q3. Before your workout, how strong (or weak) did you feel? Test group participants felt stronger before they started working out as the test group progressed (FIG. 5).

Figure 6:
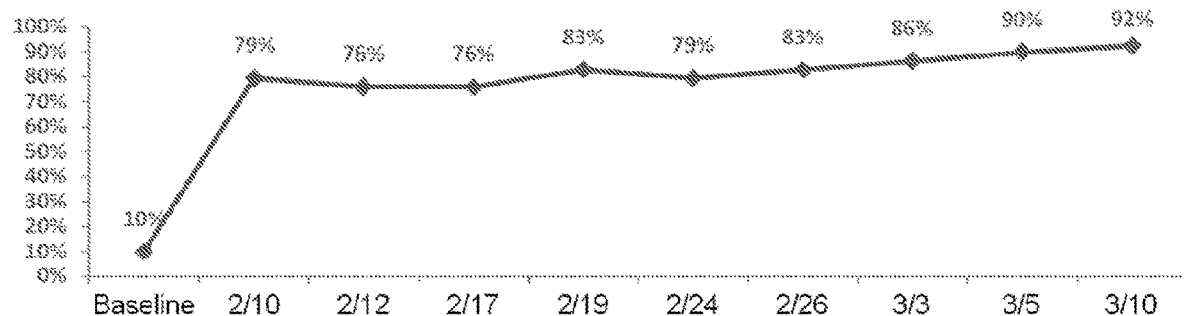

Q4. Before your workout, how ready and motivated did you feel? Test group participants felt more motivated before they started working out as the test group progressed (FIG. 6).

(2) During-Exercise

Figure 7:
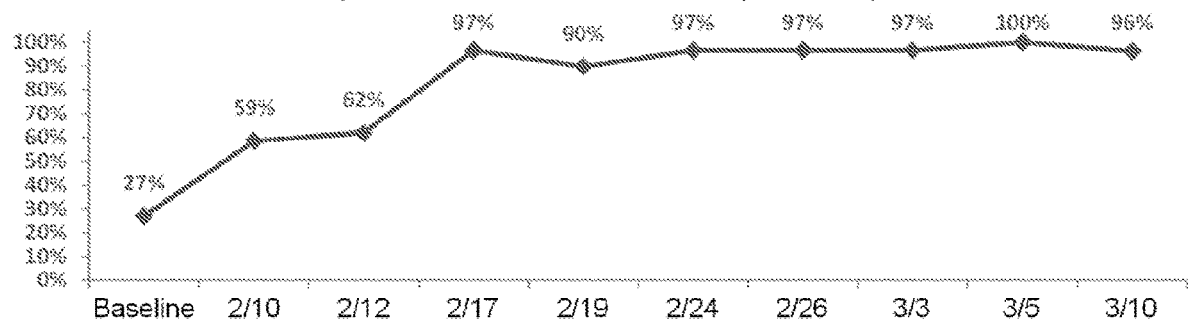

Q5. During your workout, how would you rate your workout performance? Test group participants rated their performance more positively during their workouts as the test group progressed (FIG. 7).

Figure 8:
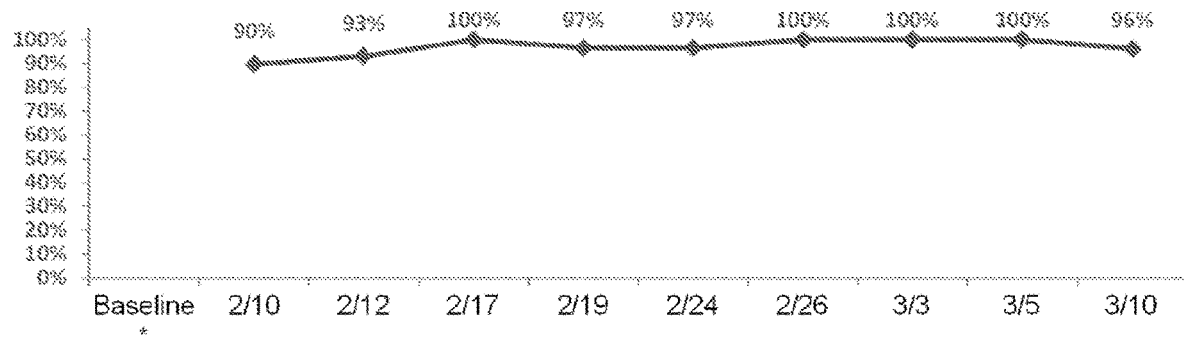

Q6. During your workout, how hard did you push yourself? Test group participants consistently pushed hard on themselves during their workouts (FIG. 8).

Figure 9:
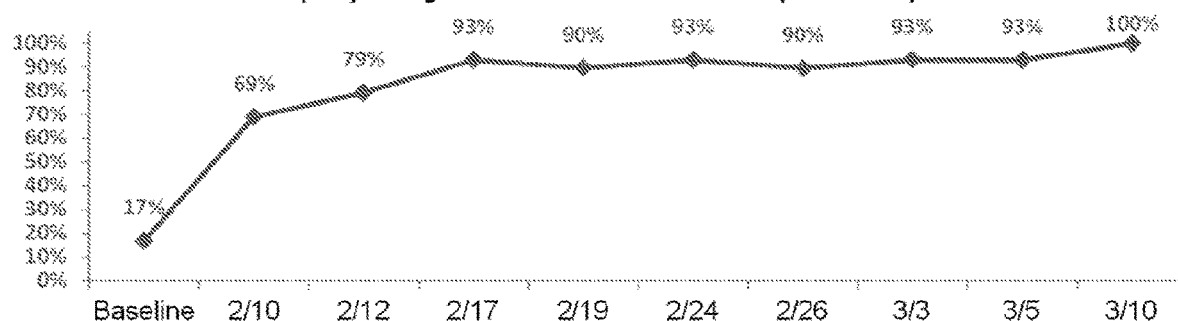

Q7. During your workout, how energized (or tired) did you feel? Test group participants felt more energized during their workouts as the test group progressed (FIG. 9).

Figure 10:
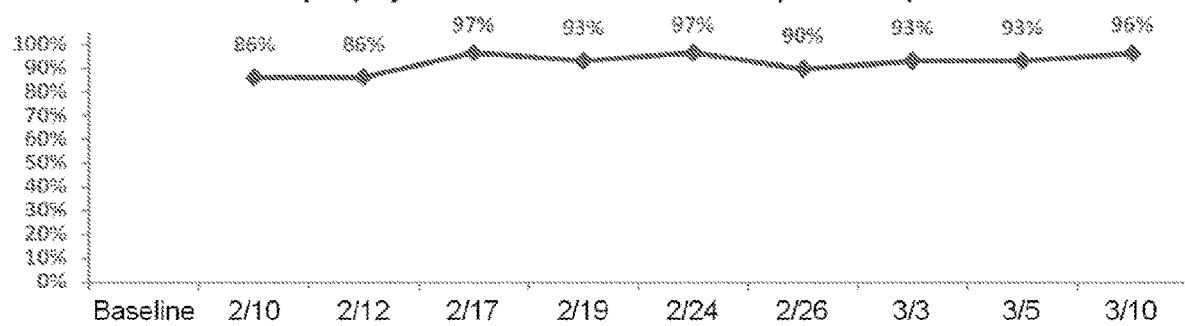

Q8. During your workout, how hydrated (or thirsty) did you feel? Test group participants consistently felt hydrated during their workouts (FIG. 10).

Figure 11:
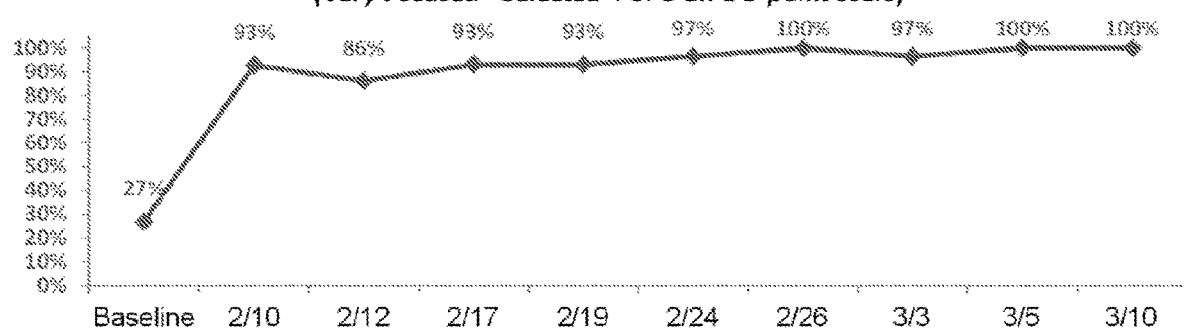

Q9. During your workout, how focused and concentrated did you feel? Test group participants consistently felt more focused during their workouts as the test group progressed (FIG. 11).

Figure 12:
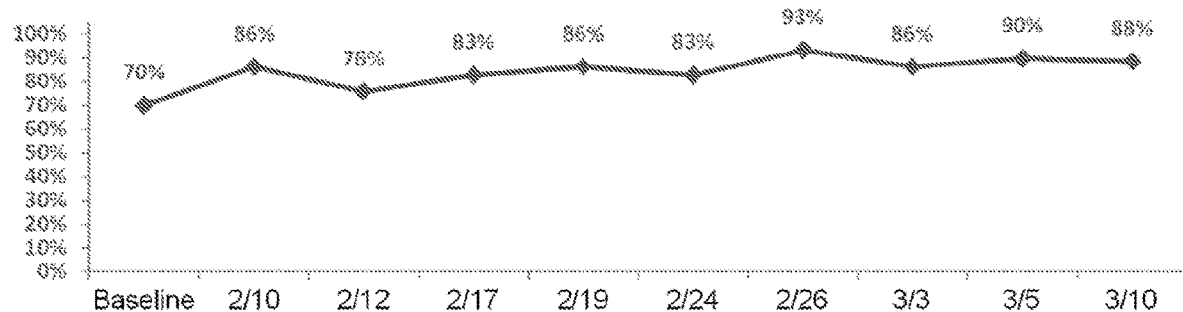

Q10. During your workout, how much did you cramp? Test group participants consistently felt less cramping during their workouts as the test group progressed (FIG. 12).

(3) Post-Exercise

Figure 13:
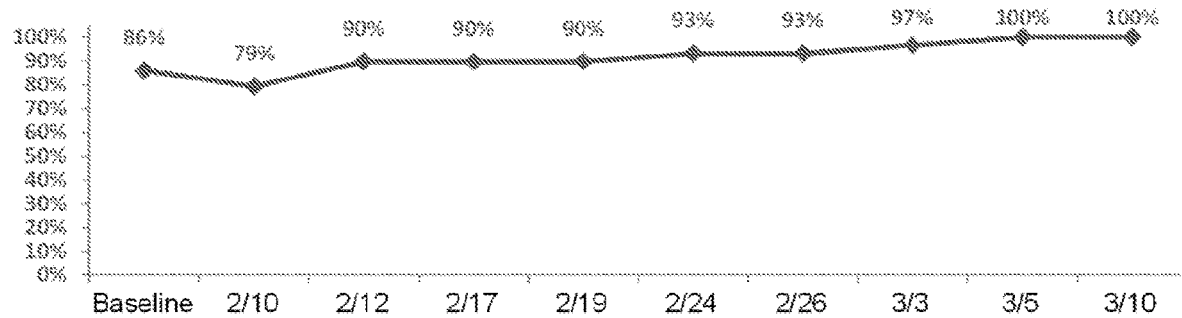

Q11. After your workout, how did you feel? Test group participants felt better overall after their workouts as the test group progressed (FIG. 13).

Figure 14:
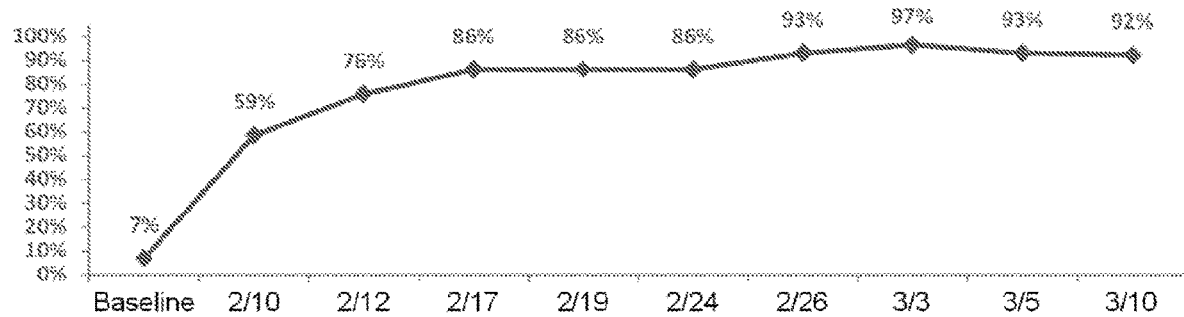

Q12. After your workout, how replenished (or depleted) did you feel? Test group participants felt more replenished after their workouts as the test group progressed (FIG. 14).

Figure 15:
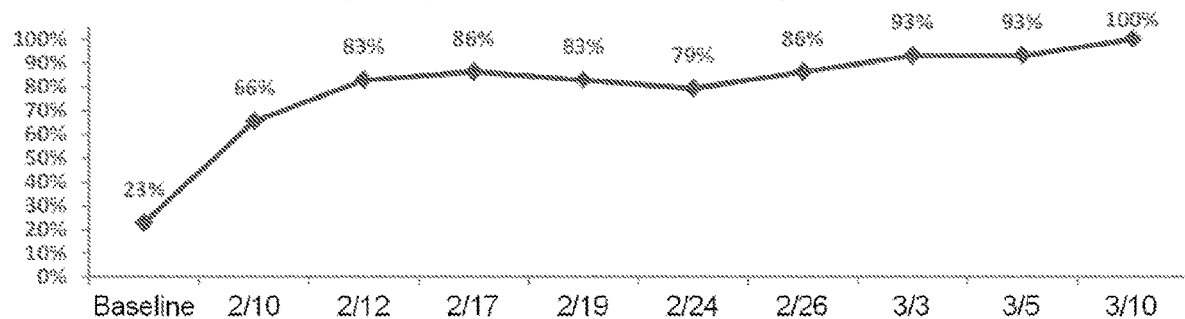

Q13. After your workout, how energized (or tired) did you feel? Test group participants felt more energized after their workouts as the test group progressed (FIG. 15).

Figure 16:
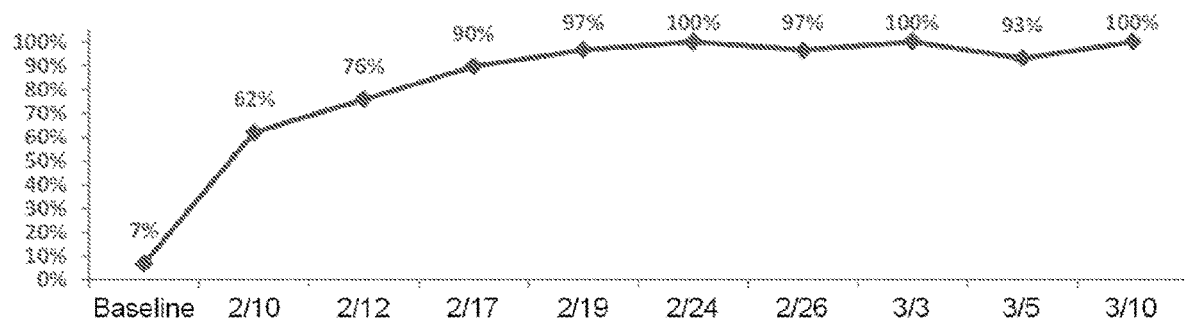

Q14. How quickly did you recover from your workout? Test group participants recovered quicker after their workouts as the test group progressed (FIG. 16).

Figure 17:
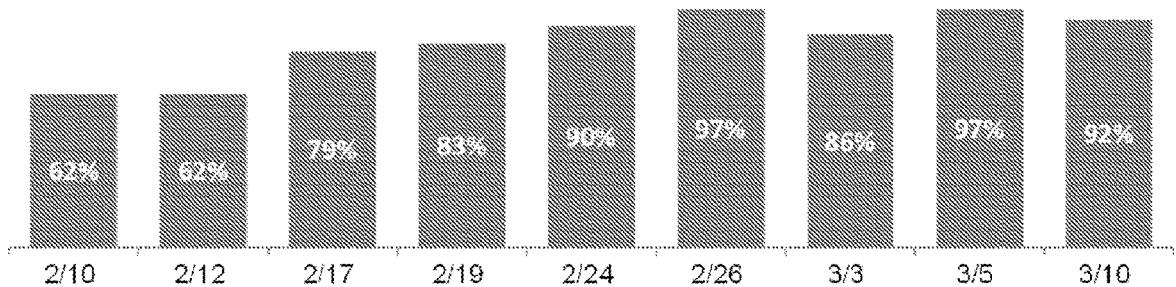

Q15. After your workout, did you see or feel a difference in your muscle definition? Test group participants felt an increased difference in their muscle definition after their workouts as the test group progressed (FIG. 17).

(4) Nighttime

Figure 18:
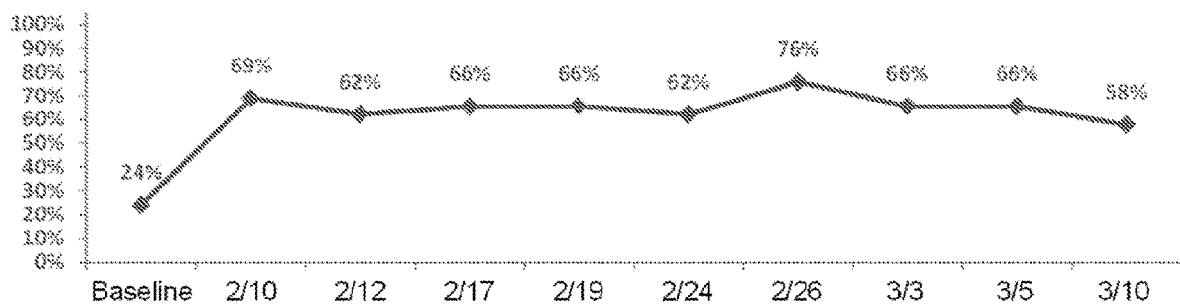

Q16. Last night, how hungry were you before you slept? Test group participants felt less hungry on nights after their workouts, but started feeling a bit hungry towards the end of the test group (FIG. 18).

Figure 19:
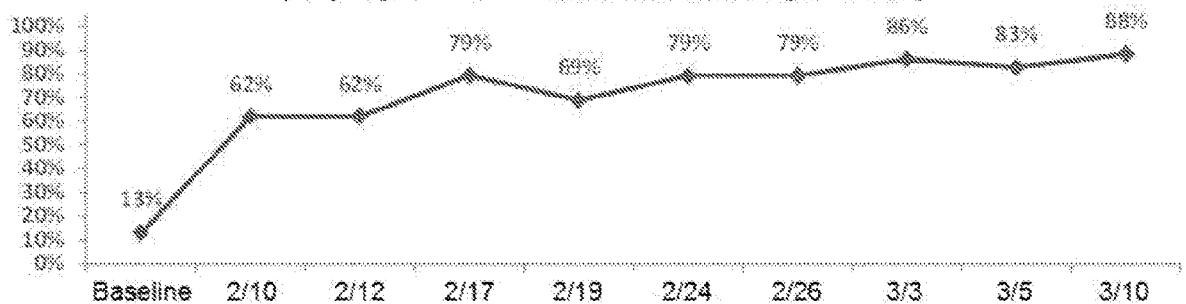

Q17. Last night, how replenished (or depleted) did you feel? Test group participants felt more replenished on nights after their workouts (FIG. 19).

Figure 20:
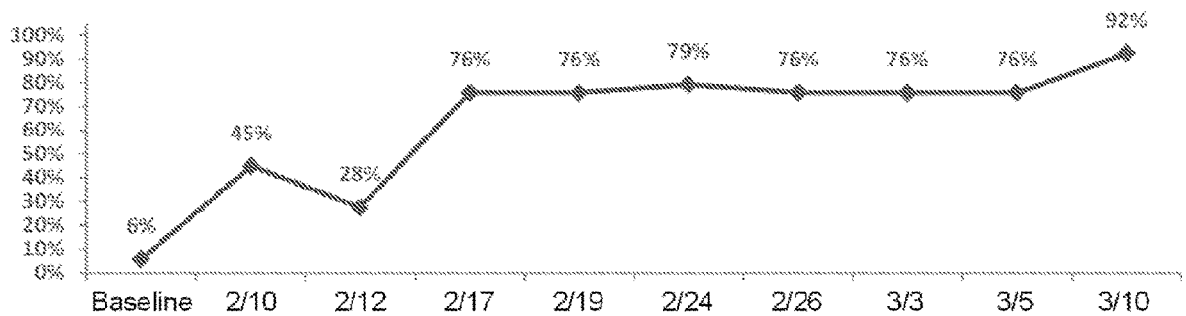

Q18. Last night, how sore did your muscles feel? Test group participants felt that their muscles were less sore during the nights after their workouts as the test group progressed (FIG. 20).

Figure 21:
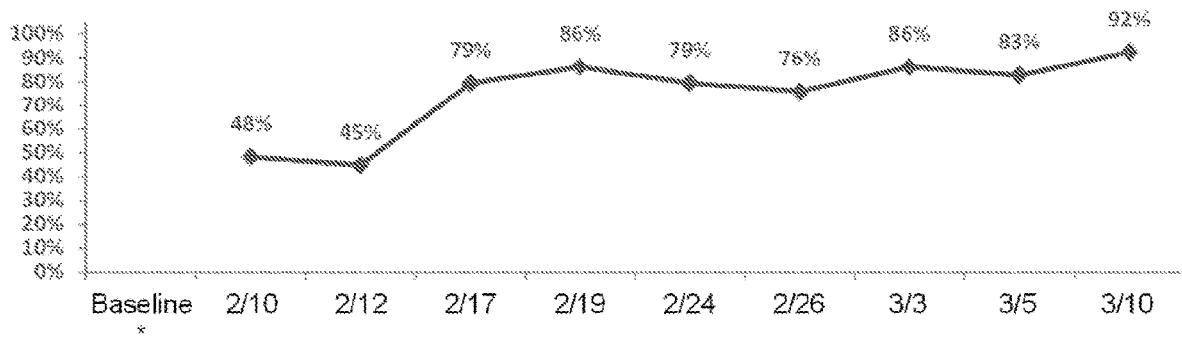

Q19. Last night, how stiff did your muscles feel? Test group participants felt that their muscles were less stiff during the nights after their workouts as the test group progressed (FIG. 21).

(5) Day after Working Out

Figure 22:
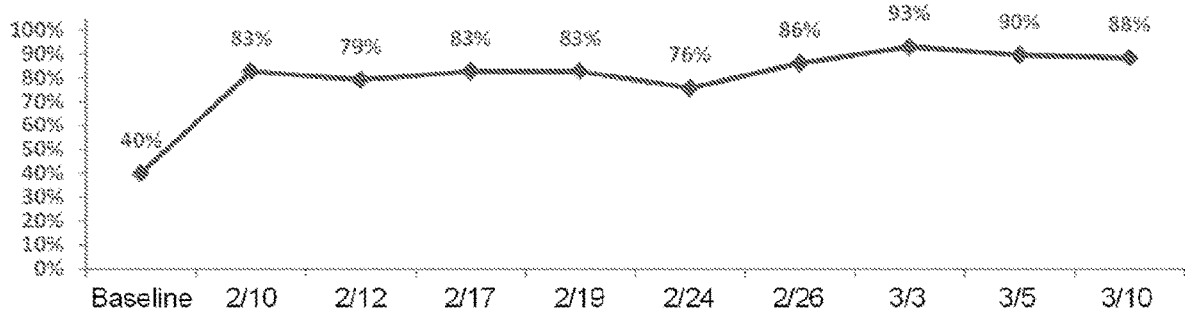

Q20. How well (or poorly) did you sleep? Test group participants felt that they consistently slept better in the morning after their workouts as the test group progressed (FIG. 22).

Figure 23:
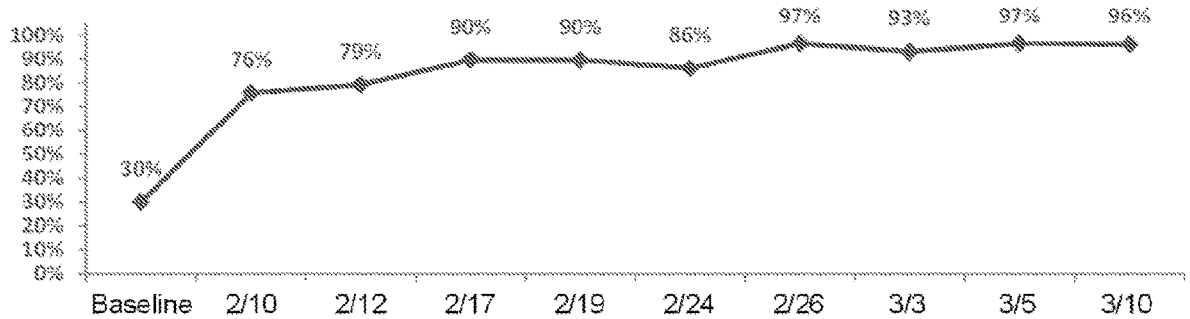

Q21. How do you feel physically? Test group participants felt physically better in the morning after their workouts as the test group progressed (FIG. 23).

Figure 24:
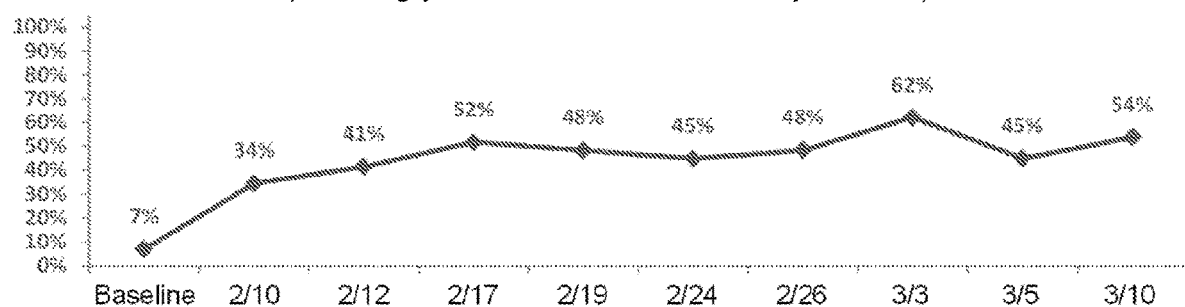

Q22. How hungry do you feel? Test group participants felt less hungry overall in the morning after their workouts as the test group progressed (FIG. 24).

Figure 25:
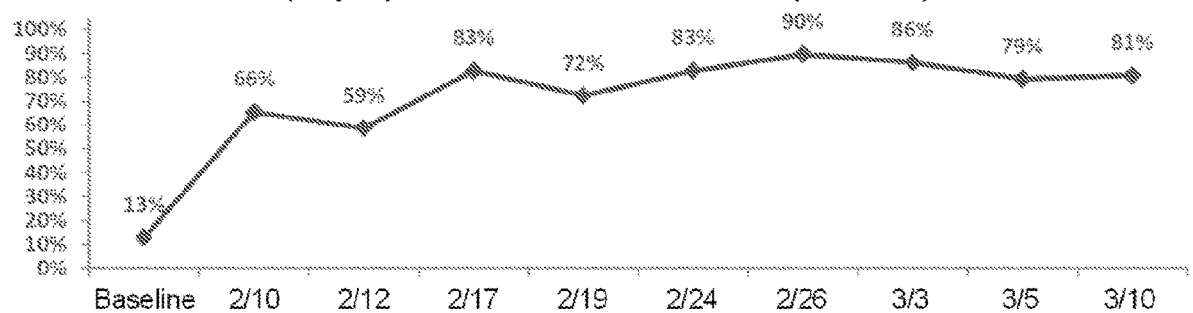

Q23. How replenished (or depleted) do you feel? Test group participants felt more replenished in the morning after their workouts as the test group progressed (FIG. 25).

Figure 26:
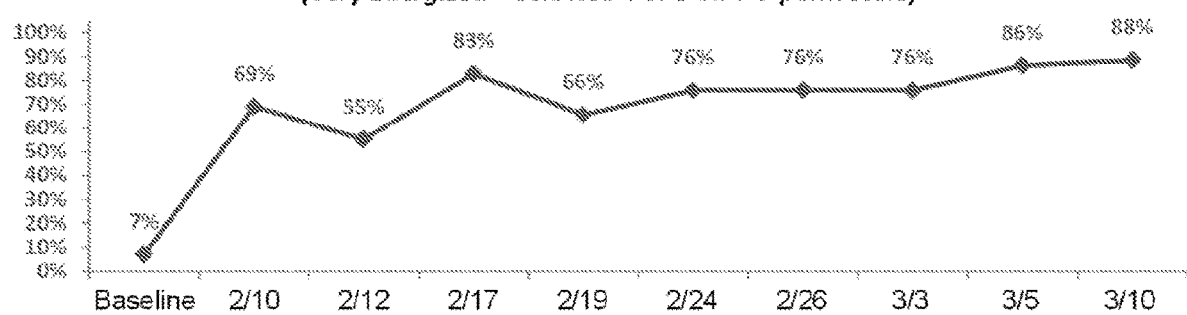

Q24. How energized (or tired) do you feel? Test group participants felt more energized in the morning after their workouts as the test group progressed (FIG. 26).

Figure 27:
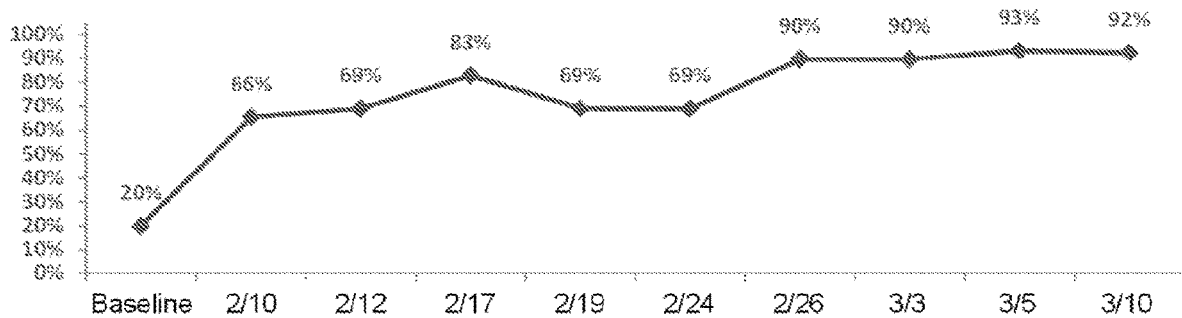

Q25. How refreshed do you feel? Test group participants felt more refreshed in the morning after their workouts as the test group progressed (FIG. 27).

Figure 28:
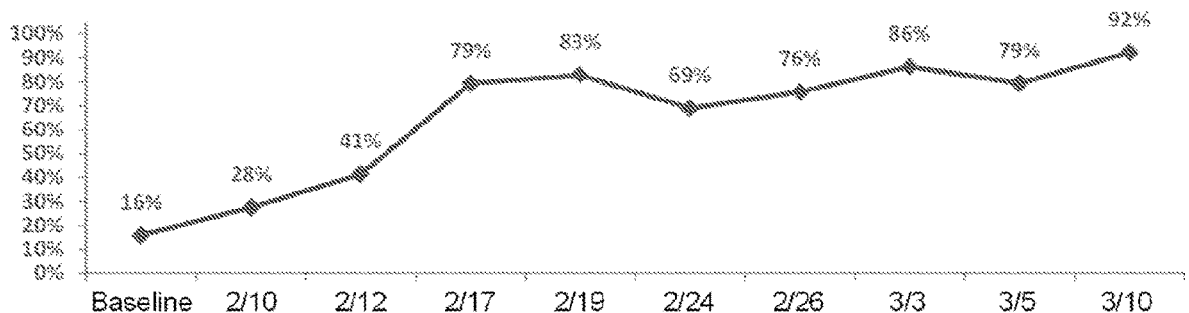

Q26. How sore are your muscles compared to 1-2 days ago? Test group participants felt the muscles were less sore compared to 1-2 days ago on the mornings after their workouts as the test group progressed (FIG. 28).

Figure 29:
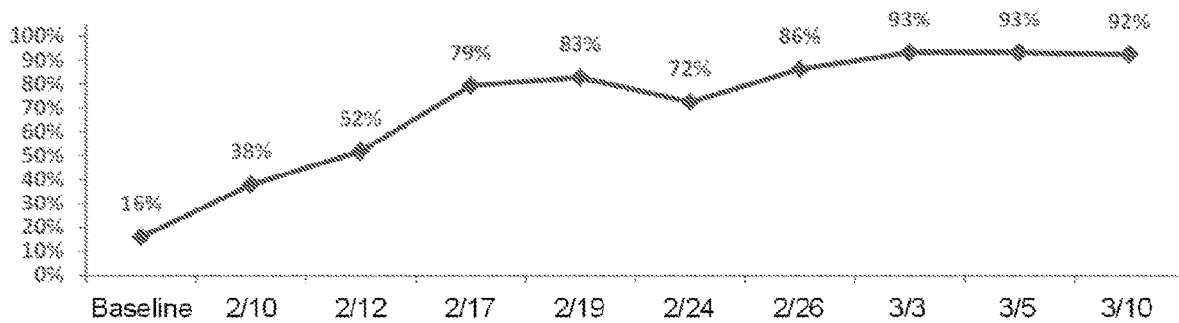

Q27. How stiff do your muscles feel? Test group participants felt the muscles were less stiff on the mornings after their workouts as the test group progressed (FIG. 29).

Figure 30:
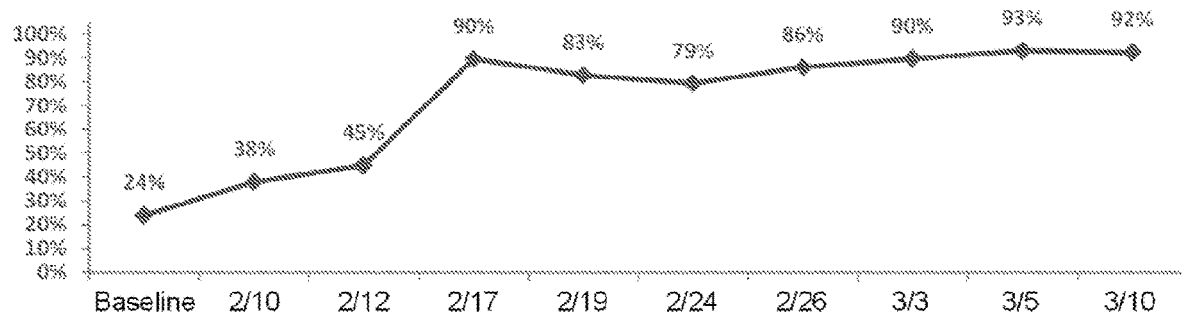

Q28. How stiff are your muscles compared to 1-2 days ago? Test group participants felt that their muscles were less stiff compared to 1-2 days ago in the morning after their workouts as the test group progressed (FIG. 30).

Figure 31:
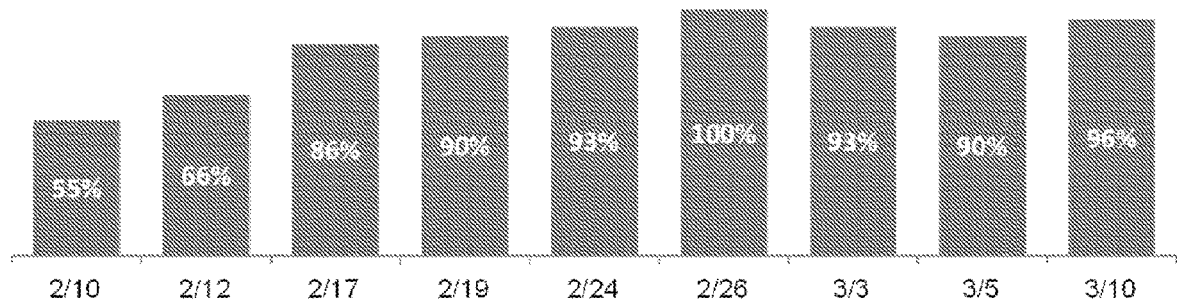

Q29. Do you see or feel a difference in your muscle definition? Test group participants felt an increased difference in their muscle definition in the morning after their workouts as the test group progressed (FIG. 31).

Figure 32:
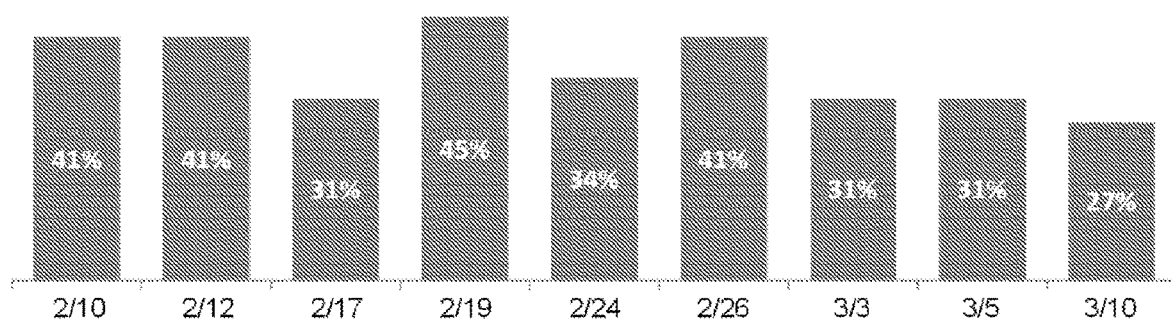

Q30. Did you consume any caffeinated drinks (e.g. tea, coffee, energy drinks, etc.) or energy chews yesterday? Less than half of test group consumed caffeine throughout the test group (FIG. 32).

Figure 33:
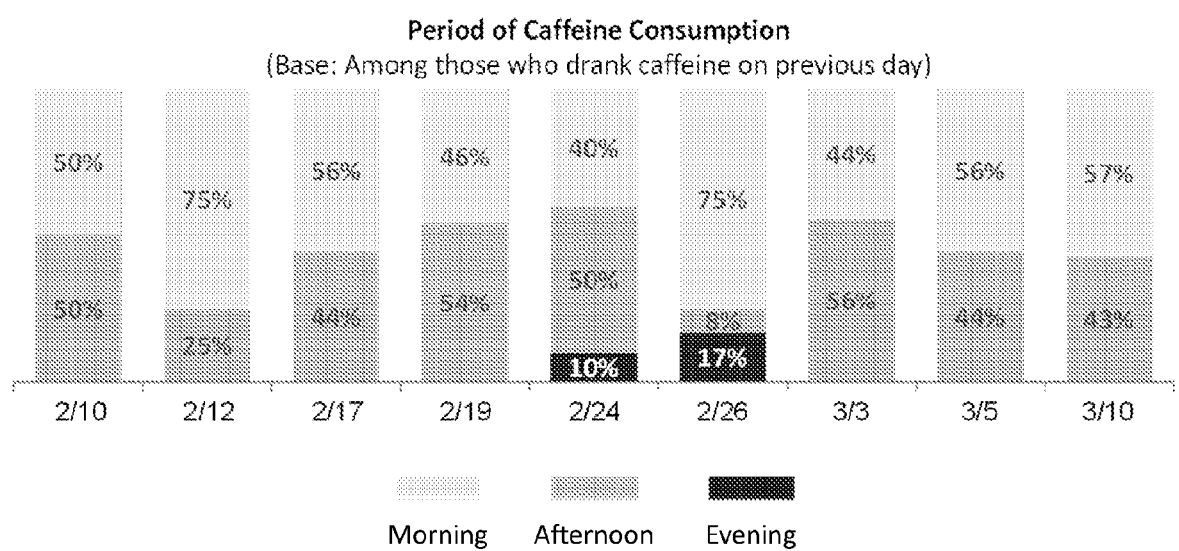

Q31. When did you consume caffeinated drinks (e.g. tea, coffee, energy drinks, etc.) or energy chews yesterday? Among those who consumed caffeine, did so mostly in the morning or afternoon (FIG. 33).

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

The invention claimed is:

1. A method for improving exercise performance and/or recovery in a subject, or controlling body weight and/or promoting weight loss in the subject, comprising:
   administering an effective amount of a composition to the subject, thereby improving exercise performance and/or recovery in the subject,
   wherein the composition comprises citric acid, beta alanine, quercetin, sodium citrate, stevia and/or stevia leaf extract, fruit flavor, green tea extract and/or natural caffeine, and potassium citrate.

2. The method of claim 1, further comprising:
   subjecting the subject to an exercise after administering the effective amount of the composition, thereby controlling body weight and/or for promoting weight loss in the subject.

3. The method of claim 1, wherein the composition further comprises sugar, sodium chloride, magnesium citrate, silicon oxide, and calcium citrate.

4. The method of claim 3, wherein the sugar is at about 30.3-31.9%, 31.9-33.4%, 33.4-34.9%, 34.9-36.4%, 36.4-37.9%, 37.9-39.4%, 39.4-41.0%, 41.0-42.5%, 42.5-44.0%, or 44.0-45.5%, or about 37.9% by weight or volume; the citric acid is at about 13.3-14.0%, 14.0-14.7%, 14.7-15.3%, 15.3-16.0%, 16.0-16.7%, 16.7-17.3%, 17.3-18.0%, 18.0-18.7%, 18.7-19.3%, or 19.3-20.0%, or about 16.7% by weight or volume; the beta alanine is at about 10.7-11.2%, 11.2-11.7%, 11.7-12.3%, 12.3-12.8%, 12.8-13.3%, 13.3-13.9%, 13.9-14.4%, 14.4-14.9%, 14.9-15.5%, or 15.5-16.0%, or about 13.3% by weight or volume; the quercetin is at about 6.70-7.04%, 7.04-7.37%, 7.37-7.71%, 7.71-8.04%, 8.04-8.38%, 8.38-8.71%, 8.71-9.05%, 9.05-9.38%, 9.38-9.72%, or 9.72-10.05%, or about 8.38% by weight or volume; the sodium citrate is at about 3.77-3.96%, 3.96-4.14%, 4.14-4.33%, 4.33-4.52%, 4.52-4.71%, 4.71-4.90%, 4.90-5.09%, 5.09-5.28%, 5.28-5.46%, or 5.46-5.65%, or about 4.71% by weight or volume; the stevia and/or stevia extract is at about 3.07-3.22%, 3.22-3.37%, 3.37-3.53%, 3.53-3.68%, 3.68-3.83%, 3.83-3.99%, 3.99-4.14%, 4.14-4.29%, 4.29-4.45%, or 4.45-4.60%, or about 3.83% by weight or volume; the fruit flavor is at about 2.67-2.80%, 2.80-2.93%, 2.93-3.07%, 3.07-3.20%, 3.20-3.33%, 3.33-3.47%, 3.47-3.60%, 3.60-3.73%, 3.73-3.87%, or 3.87-4.00%, or about 3.33% by weight or volume; the green tea extract and/or natural caffeine is at about 2.67-2.80%, 2.80-2.93%, 2.93-3.07%, 3.07-3.20%, 3.20-3.33%, 3.33-3.47%, 3.47-3.60%, 3.60-3.73%, 3.73-3.87%, or 3.87-4.00%, or about 3.33% by weight or volume; the sodium chloride is at about 1.71-1.79%, 1.79-1.88%, 1.88-1.97%, 1.97-2.05%, 2.05-2.14%, 2.14-2.22%, 2.22-2.31%, 2.31-2.39%, 2.39-2.48%, or 2.48-2.56%, or about 2.14% by weight or volume; the magnesium citrate is at about 1.67-1.75%, 1.75-1.83%, 1.83-1.92%, 1.92-2.00%, 2.00-2.08%, 2.08-2.17%, 2.17-2.25%, 2.25-2.33%, 2.33-2.42%, or 2.42-2.50%, or about 2.08% by weight or volume; the silicon dioxide is at about 1.60-1.68%, 1.68-1.76%, 1.76-1.84%, 1.84-1.92%, 1.92-2.00%, 2.00-2.08%, 2.08-2.16%, 2.16-2.24%, 2.24-2.32%, or 2.32-2.40%, or about 2.00% by weight or volume; the potassium citrate is at about 1.50-1.57%, 1.57-1.65%, 1.65-1.72%, 1.72-1.80%, 1.80-1.87%, 1.87-1.95%, 1.95-2.02%, 2.02-2.10%, 2.10-2.17%, or 2.17-2.25%, or about 1.87% by weight or volume; and the calcium citrate is at about 0.317-0.333%, 0.333-0.349%, 0.349-0.365%, 0.365-0.381%, 0.381-0.397%, 0.397-0.413%, 0.413-0.429%, 0.429-0.444%, 0.444-0.460%, or 0.460-0.476%, or about 0.397% by weight or volume; each relative to the weight or volume of the composition.

5. The method of claim 3, wherein the sugar is about 38% by weight or volume, the citric acid about 17% by weight or volume, the beta alanine about 13% by weight or volume, the quercetin about 8.4% by weight or volume, the sodium citrate about 4.7% by weight or volume, the stevia and/or stevia leaf extract is about 3.8% by weight or volume, the fruit flavor is about 3.3% by weight or volume, the green tea extract and/or natural caffeine is about 3.3% by weight or volume, the sodium chloride is about 2.1% by weight or volume, the magnesium citrate is about 2.1% by weight or volume, the silicon dioxide is about 2.0% by weight or volume, the potassium citrate is about 1.9% by weight or volume, and the calcium citrate is about 0.40% by weight or volume; each relative to the weight or volume of the composition.

6. The method of claim 1, wherein the composition further comprises dextrose.

7. The method of claim 6, wherein the citric acid is at about 8.4-8.8%, 8.8-9.3%, 9.3-9.7%, 9.7-10.1%, 10.1-10.5%, 10.5-10.9%, 10.9-11.4%, 11.4-11.8%, 11.8-12.2%, or 12.2-12.6%, or about 10.5% by weight or volume; the beta alanine is at about 13.5-14.1%, 14.1-14.8%, 14.8-15.5%, 15.5-16.2%, 16.2-16.8%, 16.8-17.5%, 17.5-18.2%, 18.2-18.9%, 18.9-19.5%, or 19.5-20.2%, or about 16.8% by weight or volume; the quercetin is at about 4.43-4.65%, 4.65-4.88%, 4.88-5.10%, 5.10-5.32%, 5.32-5.54%, 5.54-5.76%, 5.76-5.98%, 5.98-6.21%, 6.21-6.43%, or 6.43-6.65%, or about 5.54% by weight or volume; the sodium citrate is at about 8.4-8.8%, 8.8-9.3%, 9.3-9.7%, 9.7-10.1%, 10.1-10.5%, 10.5-10.9%, 10.9-11.4%, 11.4-11.8%, 11.8-12.2%, or 12.2-12.6%, or about 10.5% by weight or volume; the stevia and/or stevia extract is at about 1.94-2.03%, 2.03-2.13%, 2.13-2.23%, 2.23-2.32%, 2.32-2.42%, 2.42-2.52%, 2.52-2.61%, 2.61-2.71%, 2.71-2.81%, or 2.81-2.91%, or about 2.42% by weight or volume; the fruit flavor is at about 1.68-1.77%, 1.77-1.85%, 1.85-1.94%, 1.94-2.02%, 2.02-2.11%, 2.11-2.19%, 2.19-2.27%, 2.27-2.36%, 2.36-2.44%, or 2.44-2.53%, or about 2.11% by weight or volume; the green tea extract and/or natural caffeine is at about 1.68-1.77%, 1.77-1.85%, 1.85-1.94%, 1.94-2.02%, 2.02-2.11%, 2.11-2.19%, 2.19-2.27%, 2.27-2.36%, 2.36-2.44%, or 2.44-2.53%, or about 2.11% by weight or volume; the potassium citrate is at about 8.4-8.8%, 8.8-9.3%, 9.3-9.7%, 9.7-10.1%, 10.1-10.5%, 10.5-10.9%, 10.9-11.4%, 11.4-11.8%, 11.8-12.2%, or 12.2-12.6%, or about 10.5% by weight or volume; and the dextrose is at about 19.0-19.9%, 19.9-20.9%, 20.9-21.8%, 21.8-22.7%, 22.7-23.7%, 23.7-24.6%, 24.6-25.6%, 25.6-26.5%, 26.5-27.5%, or 27.5-28.4%, or about 23.7% by weight or volume; each relative to the weight or volume of the composition.

8. The method of claim 6, wherein the citric acid is about 11% by weight or volume, the beta alanine is about 17% by weight or volume, the quercetin is about 5.5% by weight or volume, the sodium citrate is about 11% by weight or volume, the stevia and/or stevia leaf extract is about 2.4% by weight or volume, the fruit flavor is about 2.1% by weight or volume, the green tea extract and/or natural caffeine is about 2.1% by weight or volume, the potassium citrate is about 11% by weight or volume, and the dextrose is about 24% by weight or volume; each relative to the weight or volume of the composition.

9. A method for improving exercise performance and/or recovery in a subject, or controlling body weight and/or promoting weight loss in the subject, comprising:
administering an effective amount of a composition to the subject, thereby improving exercise performance and/or recovery in the subject,
wherein the composition comprises sugar, dextrose, sodium citrate, citric acid, quercetin, magnesium citrate, potassium citrate, calcium citrate, and fruit flavor, and stevia and/or stevia leaf extract.

10. The method of claim 9, further comprising:
subjecting the subject to an exercise; and
wherein the administering of the effective amount of the composition to the subject is during the exercise, thereby controlling body weight and/or for promoting weight loss in the subject.

11. The method of claim 9, wherein the sugar is at about 31.4-32.9%, 32.9-34.5%, 34.5-36.1%, 36.1-37.6%, 37.6-39.2%, 39.2-40.8%, 40.8-42.3%, 42.3-43.9%, 43.9-45.5%, or 45.5-47.0%, or about 39.2% by weight or volume; the dextrose is at about 33.5-35.1%, 35.1-36.8%, 36.8-38.5%, 38.5-40.1%, 40.1-41.8%, 41.8-43.5%, 43.5-45.2%, 45.2-46.8%, 46.8-48.5%, or 48.5-50.2%, or about 41.8% by weight or volume; the sodium citrate is at about 6.97-7.32%, 7.32-7.67%, 7.67-8.02%, 8.02-8.36%, 8.36-8.71%, 8.71-9.06%, 9.06-9.41%, 9.41-9.76%, 9.76-10.11%, or 10.11-10.46%, or about 8.71% by weight or volume; the citric acid is at about 3.49-3.66%, 3.66-3.83%, 3.83-4.01%, 4.01-4.18%, 4.18-4.36%, 4.36-4.53%, 4.53-4.70%, 4.70-4.88%, 4.88-5.05%, or 5.05-5.23%, or about 4.36% by weight or volume; the quercetin is at about 1.74-1.83%, 1.83-1.92%, 1.92-2.00%, 2.00-2.09%, 2.09-2.18%, 2.18-2.27%, 2.27-2.35%, 2.35-2.44%, 2.44-2.53%, or 2.53-2.61%, or about 2.18% by weight or volume; the magnesium citrate is at about 0.87-0.91%, 0.91-0.96%, 0.96-1.00%, 1.00-1.05%, 1.05-1.09%, 1.09-1.13%, 1.13-1.18%, 1.18-1.22%, 1.22-1.26%, or 1.26-1.31%, or about 1.09% by weight or volume; the potassium citrate is at about 1.57-1.64%, 1.64-1.72%, 1.72-1.80%, 1.80-1.88%, 1.88-1.96%, 1.96-2.04%, 2.04-2.11%, 2.11-2.19%, 2.19-2.27%, or 2.27-2.35%, or about 1.96% by weight or volume; the calcium citrate is at about 0.332-0.349%, 0.349-0.365%, 0.365-0.382%, 0.382-0.398%, 0.398-0.415%, 0.415-0.431%, 0.431-0.448%, 0.448-0.465%, 0.465-0.481%, or 0.481-0.498%, or about 0.415% by weight or volume; the fruit flavor is at about 0.139-0.146%, 0.146-0.153%, 0.153-0.160%, 0.160-0.167%, 0.167-0.174%, 0.174-0.181%, 0.181-0.188%, 0.188-0.195%, 0.195-0.202%, or 0.202-0.209%, or about 0.174% by weight or volume; and the stevia and/or stevia leaf extract is at about 0.0697-0.0732%, 0.0732-0.0767%, 0.0767-0.0802%, 0.0802-0.0836%, 0.0836-0.0871%, 0.0871-0.0906%, 0.0906-0.0941%, 0.0941-0.0976%, 0.0976-0.1011%, or 0.1011-0.1046%, or about 0.0871% by weight or volume; each relative to the weight or volume of the composition.

12. The method of claim 9, wherein the sugar is about 39% by weight or volume, the dextrose is about 42% by weight or volume, the sodium citrate is about 8.7% by weight or volume, the citric acid is about 4.4% by weight or volume, the quercetin is about 2.2% by weight or volume, the magnesium citrate is about 1.1% by weight or volume, the potassium citrate is about 2.0% by weight or volume, the calcium citrate is about 0.41% by weight or volume, the fruit flavor is about 0.17% by weight or volume, and the stevia and/or stevia leaf extract is about 0.087% by weight or volume; each relative to the weight or volume of the composition.

13. The method of claim 9, wherein the composition further comprises silicon dioxide, and wherein the sugar is at about 41.5-43.6%, 43.6-45.7%, 45.7-47.7%, 47.7-49.8%, 49.8-51.9%, 51.9-54.0%, 54.0-56.0%, 56.0-58.1%, 58.1-60.2%, or 60.2-62.3%, or about 51.9% by weight or volume; the dextrose is at about 20.9-21.9%, 21.9-23.0%, 23.0-24.0%, 24.0-25.0%, 25.0-26.1%, 26.1-27.1%, 27.1-28.2%, 28.2-29.2%, 29.2-30.3%, or 30.3-31.3%, or about 26.1% by weight or volume; the sodium citrate is at about 6.96-7.30%, 7.30-7.65%, 7.65-8.00%, 8.00-8.35%, 8.35-8.70%, 8.70-9.04%, 9.04-9.39%, 9.39-9.74%, 9.74-10.09%, or 10.09-10.43%, or about 8.70% by weight or volume; the citric acid is at about 3.48-3.65%, 3.65-3.83%, 3.83-4.00%, 4.00-4.17%, 4.17-4.35%, 4.35-4.52%, 4.52-4.70%, 4.70-4.87%, 4.87-5.04%, or 5.04-5.22%, or about 4.35% by weight or volume; the quercetin is at about 1.75-1.84%, 1.84-1.92%, 1.92-2.01%, 2.01-2.10%, 2.10-2.18%, 2.18-2.27%, 2.27-2.36%, 2.36-2.45%, 2.45-2.53%, or 2.53-2.62%, or about 2.18% by weight or volume; the magnesium citrate is at about 1.74-1.83%, 1.83-1.91%, 1.91-2.00%, 2.00-2.09%, 2.09-2.17%, 2.17-2.26%, 2.26-2.35%, 2.35-2.43%, 2.43-

2.52%, or 2.52-2.61%, or about 2.17% by weight or volume; the silicon dioxide is at about 1.60-1.68%, 1.68-1.76%, 1.76-1.84%, 1.84-1.92%, 1.92-2.00%, 2.00-2.08%, 2.08-2.16%, 2.16-2.24%, 2.24-2.32%, or 2.32-2.40%, or about 2.00% by weight or volume; the potassium citrate is at about 1.56-1.64%, 1.64-1.72%, 1.72-1.80%, 1.80-1.88%, 1.88-1.95%, 1.95-2.03%, 2.03-2.11%, 2.11-2.19%, 2.19-2.27%, or 2.27-2.34%, or about 1.95% by weight or volume; the calcium citrate is at about 0.331-0.348%, 0.348-0.364%, 0.364-0.381%, 0.381-0.398%, 0.398-0.414%, 0.414-0.431%, 0.431-0.447%, 0.447-0.464%, 0.464-0.480%, or 0.480-0.497%, or about 0.414% by weight or volume; the fruit flavor is at about 0.139-0.146%, 0.146-0.153%, 0.153-0.160%, 0.160-0.167%, 0.167-0.174%, 0.174-0.181%, 0.181-0.188%, 0.188-0.195%, 0.195-0.202%, or 0.202-0.209%, or about 0.174% by weight or volume; and the stevia and/or stevia leaf extract is at about 0.0696-0.0730%, 0.0730-0.0765%, 0.0765-0.0800%, 0.0800-0.0835%, 0.0835-0.0870%, 0.0870-0.0904%, 0.0904-0.0939%, 0.0939-0.0974%, 0.0974-0.1009%, or 0.1009-0.1043%, or about 0.0870% by weight or volume; each relative to the weight or volume of the composition.

14. The method of claim 9, wherein the composition further comprises silicon dioxide, and wherein the sugar is about 52% by weight or volume, the dextrose is about 26% by weight or volume, the sodium citrate is about 8.7% by weight or volume, the citric acid is about 4.3% c by weight or volume, the quercetin is about 2.2% by weight or volume, the magnesium citrate is about 2.2% by weight or volume, the silicon dioxide is about 2.0% by weight or volume, the potassium citrate is about 2.0% by weight or volume, the calcium citrate is about 0.41% by weight or volume, the fruit flavor is about 0.17% by weight or volume, and the stevia and/or stevia leaf extract is about 0.087% by weight or volume; each relative to the weight or volume of the composition.

15. A method for improving exercise recovery in a subject, or controlling body weight and/or promoting lean muscle growth in the subject, comprising:
administering an effective amount of a composition to the subject, thereby improving exercise recovery in the subject,
wherein the composition comprises whey protein, pea protein, sugar, casein, cocoa powder, potassium citrate, pomegranate extract, sodium chloride, chocolate flavor, xanthan gum, stevia and/or stevia leaf extract, L-glutamine, and branched chain amino acid (BCAA).

16. The method of claim 15, further comprising:
subjecting the subject to an exercise; and
wherein the administering of the effective amount of the composition to the subject is after the exercise, thereby controlling body weight and/or for promoting lean muscle growth in the subject.

17. The method of claim 15, wherein the whey protein is at about 29.5-31.0%, 31.0-32.5%, 32.5-33.9%, 33.9-35.4%, 35.4-36.9%, 36.9-38.4%, 38.4-39.8%, 39.8-41.3%, 41.3-42.8%, or 42.8-44.3%, or about 36.9% by weight or volume; the pea protein is at about 16.9-17.7%, 17.7-18.6%, 18.6-19.4%, 19.4-20.3%, 20.3-21.1%, 21.1-22.0%, 22.0-22.8%, 22.8-23.7%, 23.7-24.5%, or 24.5-25.4%, or about 21.1% by weight or volume; the sugar is at about 13.9-14.6%, 14.6-15.3%, 15.3-16.0%, 16.0-16.7%, 16.7-17.4%, 17.4-18.1%, 18.1-18.8%, 18.8-19.5%, 19.5-20.2%, or 20.2-20.9%, or about 17.4% by weight or volume; the casein is at about 7.86-8.25%, 8.25-8.65%, 8.65-9.04%, 9.04-9.43%, 9.43-9.83%, 9.83-10.22%, 10.22-10.61%, 10.61-11.01%, 11.01-11.40%, or 11.40-11.79%, or about 9.83% by weight or volume; the cocoa powder is at about 5.63-5.92%, 5.92-6.20%, 6.20-6.48%, 6.48-6.76%, 6.76-7.04%, 7.04-7.32%, 7.32-7.61%, 7.61-7.89%, 7.89-8.17%, or 8.17-8.45%, or about 7.04% by weight or volume; the potassium citrate is at about 1.52-1.60%, 1.60-1.67%, 1.67-1.75%, 1.75-1.82%, 1.82-1.90%, 1.90-1.98%, 1.98-2.05%, 2.05-2.13%, 2.13-2.20%, or 2.20-2.28%, or about 1.90% by weight or volume; the pomegranate extract is at about 1.46-1.54%, 1.54-1.61%, 1.61-1.68%, 1.68-1.76%, 1.76-1.83%, 1.83-1.90%, 1.90-1.98%, 1.98-2.05%, 2.05-2.12%, or 2.12-2.20%, or about 1.83% by weight or volume; the sodium chloride is at about 1.13-1.18%, 1.18-1.24%, 1.24-1.30%, 1.30-1.35%, 1.35-1.41%, 1.41-1.46%, 1.46-1.52%, 1.52-1.58%, 1.58-1.63%, or 1.63-1.69%, or about 1.41% by weight or volume; the chocolate flavor is at about 0.90-0.95%, 0.95-0.99%, 0.99-1.04%, 1.04-1.08%, 1.08-1.13%, 1.13-1.17%, 1.17-1.22%, 1.22-1.26%, 1.26-1.31%, or 1.31-1.35%, or about 1.13% by weight or volume; the xanthan gum is at about 0.451-0.473%, 0.473-0.496%, 0.496-0.518%, 0.518-0.541%, 0.541-0.563%, 0.563-0.586%, 0.586-0.608%, 0.608-0.631%, 0.631-0.654%, or 0.654-0.676%, or about 0.563% by weight or volume; the stevia and/or stevia leaf extract is at about 0.270-0.284%, 0.284-0.297%, 0.297-0.311%, 0.311-0.325%, 0.325-0.338%, 0.338-0.352%, 0.352-0.365%, 0.365-0.379%, 0.379-0.392%, or 0.392-0.406%, or about 0.338% by weight or volume; the L-glutamine is at about 0.225-0.237%, 0.237-0.248%, 0.248-0.259%, 0.259-0.270%, 0.270-0.282%, 0.282-0.293%, 0.293-0.304%, 0.304-0.315%, 0.315-0.327%, or 0.327-0.338%, or about 0.282% by weight or volume; and the BCAA is at about 0.225-0.237%, 0.237-0.248%, 0.248-0.259%, 0.259-0.270%, 0.270-0.282%, 0.282-0.293%, 0.293-0.304%, 0.304-0.315%, 0.315-0.327%, or 0.327-0.338%, or about 0.282% by weight or volume; each relative to the weight or volume of the composition.

18. The method of claim 15, wherein the whey protein is about 37% by weight or volume, the pea protein is about 21% by weight or volume, the sugar is about 17% by weight or volume, the casein is about 10% by weight or volume, the cocoa powder is about 7.0% by weight or volume, the potassium citrate is about 1.9% by weight or volume, the pomegranate extract is about 1.8% by weight or volume, the sodium chloride is about 1.4% by weight or volume, the chocolate flavor is about 1.1% by weight or volume, the xanthan gum is about 0.56% by weight or volume, the stevia and/or stevia leaf extract is about 0.34% by weight or volume, the L-glutamine is about 0.28% by weight or volume, and the BCAA is about 0.28% by weight or volume; each relative to the weight or volume of the composition.

19. The method of claim 15, wherein the whey protein is at about 32.5-34.1%, 34.1-35.8%, 35.8-37.4%, 37.4-39.0%, 39.0-40.7%, 40.7-42.3%, 42.3-43.9%, 43.9-45.5%, 45.5-47.2%, or 47.2-48.8%, or about 40.7% by weight or volume; the pea protein is at about 14.6-15.4%, 15.4-16.1%, 16.1-16.8%, 16.8-17.6%, 17.6-18.3%, 18.3-19.0%, 19.0-19.8%, 19.8-20.5%, 20.5-21.2%, or 21.2-22.0%, or about 18.3% by weight or volume; the sugar is at about 11.7-12.3%, 12.3-12.8%, 12.8-13.4%, 13.4-14.0%, 14.0-14.6%, 14.6-15.2%, 15.2-15.8%, 15.8-16.3%, 16.3-16.9%, or 16.9-17.5%, or about 14.6% by weight or volume; the casein is at about 6.65-6.98%, 6.98-7.32%, 7.32-7.65%, 7.65-7.98%, 7.98-8.31%, 8.31-8.65%, 8.65-8.98%, 8.98-9.31%, 9.31-9.65%, or 9.65-9.98%, or about 8.31% by weight or volume; the cocoa powder is at about 8.8-9.2%, 9.2-9.7%, 9.7-10.1%, 10.1-10.5%, 10.5-11.0%, 11.0-11.4%, 11.4-11.9%, 11.9-12.3%, 12.3-12.7%, or 12.7-13.2%, or about 11.0% by weight or volume; the potassium citrate is at about 1.95-

2.05%, 2.05-2.15%, 2.15-2.24%, 2.24-2.34%, 2.34-2.44%, 2.44-2.54%, 2.54-2.63%, 2.63-2.73%, 2.73-2.83%, or 2.83-2.93%, or about 2.44% by weight or volume; the pomegranate extract is at about 1.27-1.33%, 1.33-1.40%, 1.40-1.46%, 1.46-1.52%, 1.52-1.59%, 1.59-1.65%, 1.65-1.71%, 1.71-1.78%, 1.78-1.84%, or 1.84-1.90%, or about 1.59% by weight or volume; the sodium chloride is at about 0.98-1.02%, 1.02-1.07%, 1.07-1.12%, 1.12-1.17%, 1.17-1.22%, 1.22-1.27%, 1.27-1.32%, 1.32-1.37%, 1.37-1.41%, or 1.41-1.46%, or about 1.22% by weight or volume; the chocolate flavor is at about 0.780-0.820%, 0.820-0.859%, 0.859-0.898%, 0.898-0.937%, 0.937-0.976%, 0.976-1.015%, 1.015-1.054%, 1.054-1.093%, 1.093-1.132%, or 1.132-1.171%, or about 0.976% by weight or volume; the xanthan gum is at about 0.195-0.205%, 0.205-0.215%, 0.215-0.224%, 0.224-0.234%, 0.234-0.244%, 0.244-0.254%, 0.254-0.263%, 0.263-0.273%, 0.273-0.283%, or 0.283-0.293%, or about 0.244% by weight or volume; the stevia and/or stevia leaf extract is at about 0.176-0.184%, 0.184-0.193%, 0.193-0.202%, 0.202-0.211%, 0.211-0.220%, 0.220-0.228%, 0.228-0.237%, 0.237-0.246%, 0.246-0.255%, or 0.255-0.263%, or about 0.220% by weight or volume; the L-glutamine is at about 0.195-0.205%, 0.205-0.215%, 0.215-0.224%, 0.224-0.234%, 0.234-0.244%, 0.244-0.254%, 0.254-0.263%, 0.263-0.273%, 0.273-0.283%, or 0.283-0.293%, or about 0.244% by weight or volume; and the BCAA is at about 0.195-0.205%, 0.205-0.215%, 0.215-0.224%, 0.224-0.234%, 0.234-0.244%, 0.244-0.254%, 0.254-0.263%, 0.263-0.273%, 0.273-0.283%, or 0.283-0.293%, or about 0.244% by weight or volume; each relative to the weight or volume of the composition.

20. The method of claim 15, wherein the whey protein is about 41% by weight or volume, the pea protein is about 18% by weight or volume, the sugar is about 15% by weight or volume, the casein is about 8.3% by weight or volume, the cocoa powder is about 11% by weight or volume, the potassium citrate is about 2.4% by weight or volume, the pomegranate extract is about 1.6%, the sodium chloride is about 1.2%, the chocolate flavor is about 0.98%, the xanthan gum is about 0.24%, the stevia and/or stevia leaf extract is about 0.22%, the L-glutamine is about 0.24%, and the BCAA is about 0.24%; each relative to the weight or volume of the composition.

21. A method for improving exercise recovery in a subject, or controlling body weight and/or promoting lean muscle growth in the subject, comprising:
    administering an effective amount of a composition to the subject, thereby improving exercise recovery in the subject,
    wherein the composition comprises casein, sugar, vanilla flavor, tart cherry extract, sodium chloride, branched chain amino acid (BCAA), L-glutamine, stevia and/or stevia leaf extract, and xanthan gum.

22. The method of claim 21, further comprising:
    subjecting the subject to an exercise; and
    wherein the administering of the effective amount of the composition to the subject is after the exercise and before sleep, thereby controlling body weight and/or for promoting lean muscle growth in the subject.

23. The method of claim 21, wherein the casein is at about 65.3-68.5%, 68.5-71.8%, 71.8-75.1%, 75.1-78.3%, 78.3-81.6%, 81.6-84.9%, 84.9-88.1%, 88.1-91.4%, 91.4-94.7%, or 94.7-97.9%, or about 81.6% by weight or volume; the sugar is at about 10.4-10.9%, 10.9-11.4%, 11.4-12.0%, 12.0-12.5%, 12.5-13.0%, 13.0-13.5%, 13.5-14.0%, 14.0-14.6%, 14.6-15.1%, or 15.1-15.6%, or about 13.0% by weight or volume; the vanilla flavor is at about 1.40-1.47%, 1.47-1.54%, 1.54-1.61%, 1.61-1.68%, 1.68-1.75%, 1.75-1.82%, 1.82-1.89%, 1.89-1.96%, 1.96-2.04%, or 2.04-2.11%, or about 1.75% by weight or volume; the tart cherry extract is at about 1.35-1.41%, 1.41-1.48%, 1.48-1.55%, 1.55-1.62%, 1.62-1.68%, 1.68-1.75%, 1.75-1.82%, 1.82-1.89%, 1.89-1.95%, or 1.95-2.02%, or about 1.68% by weight or volume; the sodium chloride is at about 0.561-0.589%, 0.589-0.618%, 0.618-0.646%, 0.646-0.674%, 0.674-0.702%, 0.702-0.730%, 0.730-0.758%, 0.758-0.786%, 0.786-0.814%, or 0.814-0.842%, or about 0.702% by weight or volume; the BCAA is at about 0.281-0.295%, 0.295-0.309%, 0.309-0.323%, 0.323-0.337%, 0.337-0.351%, 0.351-0.365%, 0.365-0.379%, 0.379-0.393%, 0.393-0.407%, or 0.407-0.421%, or about 0.351% by weight or volume; the L-glutamine is at about 0.281-0.295%, 0.295-0.309%, 0.309-0.323%, 0.323-0.337%, 0.337-0.351%, 0.351-0.365%, 0.365-0.379%, 0.379-0.393%, 0.393-0.407%, or 0.407-0.421%, or about 0.351% by weight or volume; the stevia and/or stevia leaf extract is at about 0.253-0.265%, 0.265-0.278%, 0.278-0.291%, 0.291-0.303%, 0.303-0.316%, 0.316-0.328%, 0.328-0.341%, 0.341-0.354%, 0.354-0.366%, or 0.366-0.379%, or about 0.316% by weight or volume; and the xanthan gum is at about 0.196-0.206%, 0.206-0.216%, 0.216-0.226%, 0.226-0.236%, 0.236-0.246%, 0.246-0.255%, 0.255-0.265%, 0.265-0.275%, 0.275-0.285%, or 0.285-0.295%, or about 0.246% by weight or volume; each relative to the weight or volume of the composition.

24. The method of claim 21, wherein the casein is about 82% by weight or volume, the sugar is about 13% by weight or volume, the vanilla flavor is about 1.8% by weight or volume, the tart cherry extract is about 1.7% by weight or volume, the sodium chloride is about 0.70% by weight or volume, the BCAA is about 0.35% by weight or volume, the L-glutamine is about 0.35% by weight or volume, the stevia and/or stevia leaf extract is about 0.32% by weight or volume, and the xanthan gum is about 0.25% by weight or volume; each relative to the weight or volume of the composition.

25. The method of claim 21, wherein the casein is at about 64.9-68.2%, 68.2-71.4%, 71.4-74.7%, 74.7-77.9%, 77.9-81.2%, 81.2-84.4%, 84.4-87.7%, 87.7-90.9%, 90.9-94.2%, or 94.2-97.4%, or about 81.2% by weight or volume; the sugar is at about 11.1-11.6%, 11.6-12.2%, 12.2-12.8%, 12.8-13.3%, 13.3-13.9%, 13.9-14.4%, 14.4-15.0%, 15.0-15.5%, 15.5-16.1%, or 16.1-16.6%, or about 13.9% by weight or volume; the vanilla flavor is at about 1.43-1.50%, 1.50-1.57%, 1.57-1.64%, 1.64-1.71%, 1.71-1.79%, 1.79-1.86%, 1.86-1.93%, 1.93-2.00%, 2.00-2.07%, or 2.07-2.14%, or about 1.79% by weight or volume; the tart cherry extract is at about 1.37-1.44%, 1.44-1.51%, 1.51-1.58%, 1.58-1.65%, 1.65-1.71%, 1.71-1.78%, 1.78-1.85%, 1.85-1.92%, 1.92-1.99%, or 1.99-2.06%, or about 1.71% by weight or volume; the sodium chloride is at about 0.571-0.600%, 0.600-0.629%, 0.629-0.657%, 0.657-0.686%, 0.686-0.714%, 0.714-0.743%, 0.743-0.771%, 0.771-0.800%, 0.800-0.829%, or 0.829-0.857%, or about 0.714% by weight or volume; the stevia and/or stevia leaf extract is at about 0.257-0.270%, 0.270-0.283%, 0.283-0.296%, 0.296-0.309%, 0.309-0.321%, 0.321-0.334%, 0.334-0.347%, 0.347-0.360%, 0.360-0.373%, or 0.373-0.386%, or about 0.321% by weight or volume; and the xanthan gum is at about 0.200-0.210%, 0.210-0.220%, 0.220-0.230%, 0.230-0.240%, 0.240-0.250%, 0.250-0.260%, 0.260-0.270%, 0.270-0.280%, 0.280-0.290%, or 0.290-0.300%, or about 0.250% by weight or volume; each relative to the weight or volume of the composition.

26. The method of claim 21, wherein the casein is about 81% by weight or volume, the sugar is about 14% by weight or volume, the vanilla flavor is about 1.8% by weight or volume, the tart cherry extract is about 1.7% by weight or volume, the sodium chloride is about 0.71% by weight or volume, the stevia and/or stevia leaf extract is about 0.32% by weight or volume, and the xanthan gum is about 0.25% by weight or volume; each relative to the weight or volume of the composition.

* * * * *